(12) United States Patent
Harn et al.

(10) Patent No.: US 11,524,072 B2
(45) Date of Patent: Dec. 13, 2022

(54) VACCINE DELIVERY METHOD

(71) Applicant: UNIVERSITY OF GEORGIA RESEARCH FOUNDATION, INC., Athens, GA (US)

(72) Inventors: Donald A. Harn, Athens, GA (US); Rafaella Queiroz, Minas Gerais (BR); Lisa Shollenberger, Norfolk, VA (US); Emily-Joy Farah Samli, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/061,696

(22) Filed: Oct. 2, 2020

(65) Prior Publication Data

US 2021/0015916 A1 Jan. 21, 2021

Related U.S. Application Data

(63) Continuation of application No. 15/411,083, filed on Jan. 20, 2017, now abandoned, which is a
(Continued)

(51) Int. Cl.
| | |
|---|---|
| *A61K 39/39* | (2006.01) |
| *A61K 39/00* | (2006.01) |
| *A61K 39/104* | (2006.01) |
| *A61K 39/12* | (2006.01) |
| *A61K 9/00* | (2006.01) |
| *A61K 9/06* | (2006.01) |
| *A61K 39/02* | (2006.01) |
| *A61K 39/145* | (2006.01) |
| *A61K 39/29* | (2006.01) |
| *A61K 47/42* | (2017.01) |
| *A61K 39/012* | (2006.01) |
| *A61K 39/108* | (2006.01) |

(Continued)

(52) U.S. Cl.
CPC ............ *A61K 39/39* (2013.01); *A61K 9/0019* (2013.01); *A61K 9/06* (2013.01); *A61K 39/00* (2013.01); *A61K 39/0003* (2013.01); *A61K 39/012* (2013.01); *A61K 39/0208* (2013.01); *A61K 39/0258* (2013.01); *A61K 39/0275* (2013.01); *A61K 39/04* (2013.01); *A61K 39/05* (2013.01); *A61K 39/08* (2013.01); *A61K 39/085* (2013.01); *A61K 39/092* (2013.01); *A61K 39/099* (2013.01); *A61K 39/102* (2013.01); *A61K 39/104* (2013.01); *A61K 39/1045* (2013.01); *A61K 39/12* (2013.01); *A61K 39/145* (2013.01); *A61K 39/15* (2013.01); *A61K 39/155* (2013.01); *A61K 39/17* (2013.01); *A61K 39/215* (2013.01); *A61K 39/255* (2013.01); *A61K 39/265* (2013.01); *A61K 39/29* (2013.01); *A61K 39/292* (2013.01); *A61K 47/42* (2013.01); *A61K 2039/5252* (2013.01); *A61K 2039/53* (2013.01); *A61K 2039/54* (2013.01); *A61K 2039/545* (2013.01); *A61K 2039/552* (2013.01); *A61K 2039/55505* (2013.01); *A61K 2039/55516* (2013.01); *A61K 2039/55555* (2013.01); *A61K 2039/55561* (2013.01); *A61K 2039/55566* (2013.01); *A61K 2039/575* (2013.01); *C12N 2710/16334* (2013.01); *C12N 2710/16734* (2013.01); *C12N 2710/24034* (2013.01); *C12N 2720/10034* (2013.01); *C12N 2720/12334* (2013.01); *C12N 2730/10134* (2013.01); *C12N 2750/10034* (2013.01); *C12N 2750/14334* (2013.01); *C12N 2760/16134* (2013.01); *C12N 2760/16171* (2013.01); *C12N 2760/18034* (2013.01); *C12N 2760/18134* (2013.01); *C12N 2770/10034* (2013.01); *C12N 2770/20034* (2013.01); *C12N 2770/24334* (2013.01); *C12N 2770/32334* (2013.01); *Y02A 50/30* (2018.01)

(58) Field of Classification Search
CPC ........ A61K 39/39; A61K 39/00; A61K 39/12; A61K 39/145; A61K 9/0019; A61K 9/06
See application file for complete search history.

(56) References Cited

U.S. PATENT DOCUMENTS

| | | |
|---|---|---|
| 5,670,483 A | 9/1997 | Zhang et al. |
| 6,540,999 B1 | 4/2003 | Harn et al. |

(Continued)

FOREIGN PATENT DOCUMENTS

| | | |
|---|---|---|
| WO | WO 01/98206 A1 | 12/2001 |
| WO | WO 2007/052056 A1 | 5/2007 |

(Continued)

OTHER PUBLICATIONS

Koutsopoulos et al. 2009 (Controlled release of functional proteins through designer self-assembling peptide nanofiber hydrogel scaffold; PNAS 106(12): 4623-4628). (Year: 2009).*

(Continued)

*Primary Examiner* — Mary Maille Lyons
(74) *Attorney, Agent, or Firm* — Mueting Raasch Group

(57) ABSTRACT

A vaccine delivery method is presented that includes a composition including as one component a slurry matrix that is a liquid at room temperature and a gel at physiological pH, physiological salt concentrations and/or physiological temperatures and as a second component one or more antigens. Also included are methods of inducing an immune response in a subject and vaccinating a subject by administering such compositions.

10 Claims, 34 Drawing Sheets

Specification includes a Sequence Listing.

Related U.S. Application Data continuation of application No. 13/793,329, filed on Mar. 11, 2013, now Pat. No. 9,566,338, which is a continuation-in-part of application No. PCT/US2012/034012, filed on Apr. 18, 2012.

(60) Provisional application No. 61/476,431, filed on Apr. 18, 2011.

(51) Int. Cl.

| | | |
|---|---|---|
| *A61K 39/112* | (2006.01) | |
| *A61K 39/04* | (2006.01) | |
| *A61K 39/05* | (2006.01) | |
| *A61K 39/08* | (2006.01) | |
| *A61K 39/085* | (2006.01) | |
| *A61K 39/09* | (2006.01) | |
| *A61K 39/102* | (2006.01) | |
| *A61K 39/15* | (2006.01) | |
| *A61K 39/155* | (2006.01) | |
| *A61K 39/17* | (2006.01) | |
| *A61K 39/215* | (2006.01) | |
| *A61K 39/255* | (2006.01) | |
| *A61K 39/265* | (2006.01) | |

(56) References Cited

U.S. PATENT DOCUMENTS

| | | |
|---|---|---|
| 6,548,630 B1 | 4/2003 | Zhang et al. |
| 6,841,543 B1 | 1/2005 | Harn et al. |
| 7,799,755 B2 | 9/2010 | Harn et al. |
| 2002/0142945 A1 | 10/2002 | Harn et al. |
| 2004/0047866 A1 | 3/2004 | Harn et al. |
| 2004/0185057 A1 | 9/2004 | Kirkby et al. |
| 2004/0258702 A1 | 12/2004 | Blonder et al. |
| 2005/0053667 A1* | 3/2005 | Irvine ............. A61P 31/04 424/490 |
| 2005/0084534 A1 | 4/2005 | Ni et al. |
| 2005/0181973 A1 | 8/2005 | Genove |
| 2005/0214227 A1 | 9/2005 | Prestrelski et al. |
| 2006/0040893 A1 | 2/2006 | Harn et al. |
| 2007/0149477 A1 | 6/2007 | Harn et al. |
| 2008/0057061 A1 | 3/2008 | Harn et al. |
| 2009/0136991 A1 | 5/2009 | Jones et al. |
| 2013/0195910 A1 | 8/2013 | Harn et al. |
| 2017/0202958 A1 | 7/2017 | Harn et al. |

FOREIGN PATENT DOCUMENTS

| | | |
|---|---|---|
| WO | WO 2010/138192 A2 | 12/2010 |
| WO | WO 2010/138193 A2 | 12/2010 |
| WO | WO 2010/138193 A3 | 12/2010 |
| WO | WO 2012/145355 A1 | 10/2012 |

OTHER PUBLICATIONS

Guo et al. 2010 (Protection against multiple influenza A virus subtypes by intranasal administration of recombinant nucleoprotein; Arch Virol 155: 1765-1775). (Year: 2010).*
International Preliminary Report on Patentability (Form PCT/IB/373) dated Oct. 22, 2013, in connection with International Patent Application No. PCT/US2012/034012, filed Apr. 18, 2012.
International Search Report (Form PCT/ISA/210) dated Aug. 24, 2012, in connection with International Patent Application No. PCT/US2012/034012, filed Apr. 18, 2012.
Written Opinion of the International Searching Authority (Form PCT/ISA/237) dated Aug. 24, 2012, in connection with International Patent Application No. PCT/US2012/034012, filed Apr. 18, 2012.
Partial Supplementary European Search Report, dated Dec. 5, 2014 by the European Patent Office for PCT/2012034012).
Japanese Patent Application No. 2014-506498, filed Oct. 17, 2013; Report of Pretrial Reexamination dated Sep. 26, 2016 [English language translation included]. 8 pages.
Abu-Yousif et al., PuraMatrix encapsulation of cancer cells, Dec. 17, 2009, *J. Vis. Exp.* 34:e1692.
Allen et al., Type I collagen, fibrin and PuraMatrix matrices provide permissive environments for human endothelial and mesenchymal progenitor cells to form neovascular networks, Apr. 2011, *J. Tissue Eng. Regen. Med.* 5(4):e74-86 (published online Jan. 10, 2011).
Anderson et al., Physicochemical characterization and biological activity of synthetic TLR4 agonist formulations, Jan. 2010, *Colloids and Surfaces B: Biointerfaces* 75(1):123-32 (published online Aug. 20, 2009).
Attributes & Comparison. Product information [online]; [retrieved Apr. 2, 2012]. Retrieved from the internet: <URL: http://www.puramatrix.com/pr05.html>; 1 pg.
Balakrishnan et al., 2001, "Biopolymer-based hydrogels for cartilage tissue engineering." *Chemical Reviews* 111(8):4453-4474.
Bao et al., Effects of inoculation site and Matrigel on growth and metastasis of human breast cancer cells, Aug. 1994, *Br. J. Cancer* 70(2):228-32.
BD Extracellular Matrix Proteins—ECM Types—Matrigel™ Matrix. Product Information [online]. BD Biosciences, San Jose, CA & Franklin Lakes, NJ [retrieved Apr. 2, 2012]. Retrieved from the internet: <URL: http://www.bdbiosciences.com/cellculture/ecm/ecmtypes/index.jsp>; 6pgs.
BD™ PuraMatrix™ Peptide Hydrogel (Catalog No. 354250, SPC-354250-G, rev. 2.0). Guidelines for Use [online]. BD Biosciences, Bedford, MA, Copyright Date 2004 [retrieved on Mar. 11, 2014]. Retrieved from the Internet: <URL: http://puramatrix.com/protocol_pdfs/PuraMatrix_Guidelines.pdf>; 16 pgs.
BD™ PuraMatrix™ Peptide Hydrogel. Brochure [online]. BD Biosciences, Bedford, MA, Copyright Date 2004 [retrieved on Mar. 12, 2014]. Retrieved from the Internet: <URL: http://www.puramatrix.com/protocol_pdfs/BDPuraMatrix_Brochure.pdf>; 4 pgs.
Bhardwaj et al. "TLR Agonists: Are They Good Adjuvants?" Cancer J, 2010; 16(4):382-391.
Brewer et al., In interleukin-4-deficient mice, alum not only generates T helper 1 responses equivalent to freund's complete adjuvant, but continues to induce T helper 2 cytokine production, Sep. 1996, *Eur. J. Immunol.* 26(9):2062-66.
Browning et al., 2014, "Determination of the in vivo degradation mechanism of PEGDA hydrogels." *J Biomed Mater Res Part A.* 102A:4244-4251.
Cao et al., Interferon-inducible protein 10 induction and inhibition of angiogenesis in vivo by the antitumor agent 5,6-dimethylxanthenone-4-acetic acid (DMXAA), Feb. 2001, *Cancer Res.* 61(4):1517-21.
Centers for Disease Control and Prevention, Melioidosis, Jan. 26, 2012 [retrieved on Mar. 12, 2014]. Retrieved from the Internet: <URL: http://www.cdc.gov/melioidosis/>; 1 pg.
Chesson et al., Antigenic peptide nanofibers elicit adjuvant-free CD8+ T cell responses, Feb. 26, 2014, *Vaccine* 32(10):1174-80 (published online Dec. 2, 2013).
Chong et al., 2009, "A paradigm for peptide vaccine delivery using viral epitopes encapsulated in degradable polymer hydrogel capsules." *Biomaterials* 30(28):5178-5186.
Code of Federal Regulations, Title 21, 184.1588—Food and Drugs, Chapter I—Food and Drugs Administration Department of Health and Human Services, Subchapter B—Food for Human Consumption (Continued), Part 184—Direct Food Substances Affirmed as GRAS: Pectins. Obtained online Mar. 29, 2017 from accessdata.fda.gov/scripts/cdrh/cfdocs/cfcfr/CFRSearch.cfm?fr=184.1588. 1 page.
Coeshott et al., 2004, "Pluronic® F127-based systemic vaccine delivery systems." *Vaccine* 22(19):2396-2405.
Cohen et al., 2013, "Novel HIV vaccine strategies: overview and perspective." *Therapeutic Advances in Vaccines* 1(3):99-112.
Coler et al., A synthetic adjuvant to enhance and expand immune responses to influenza vaccines, Oct. 27, 2010, *PLOS One* 5(10):e13677.
Coler et al., Development and characterization of synthetic glucopyranosyl lipid adjuvant system as a vaccine adjuvant, Jan. 26, 2011, *PLOS One* 6(1):e16333.

(56) References Cited

OTHER PUBLICATIONS

Curley et al., Fabrication of micropatterned hydrogels for neural culture systems using dynamic mask projection photolithography, Feb. 11, 2011, *J. Vis. Exp.*, 48:e2636.
Da'Dara et al., DNA-based vaccines protect against zoonotic schistosomiasis in water buffalo, Jul. 2008, *Vaccine*, 26(29-30):3617-25.
Da'Dara et al., Elimination of helminth infection restores HIV-1C vaccine-specific T cell responses independent of helminth-induced IL-10, Feb. 2010, *Vaccine* 28(5):1310-17 (published online Nov. 24, 2009).
Dai et al., DNA vaccination by electroporation and boosting with recombinant proteins enhances the efficacy of DNA vaccines for *Schistosomiasis japonica*, Dec. 2009, *Clin. Vaccine Immunol.* 16(12):1796-1803 (published online Oct. 7, 2009).
Davis et al., CpG DNA is a potent enhancer of specific immunity in mice immunized with recombinant hepatitis B surface antigen, Jan. 1998, *J. Immunol.* 160(2):870-76.
Floyd, Vaccinations for the Swine Herd, Jul. 1996, Alabama Cooperative Extension System, ANR-902 [retrieved on Mar. 11, 2014]. Retrieved from the Internet:<URL: http://www.aces.edu/pubs/docs/A/ANR-0902/ANR-0902.pdf>; 6 pgs.
Garulli et al., 2014, "Exploring mucosal immunization with a recombinant influenza virus carrying an HIV-polyepitope in mice with pre-existing immunity to influenza." *Vaccine* 32(21):2501-2506.
Gelain et al., Slow and sustained release of active cytokines from self-assembling peptide scaffolds, Aug. 3, 2010, *J. Control. Release* 145(3):231-39 (published online May 4, 2010).
Grant, The basement-membrane-like matrix of the mouse EHS tumor: II. Immunohistochemical quantitation of six of its components, Dec. 1985, *Am. J. Anat*. 174(4):387-98.
Grenfell et al., New vaccination delivery regimen drives enhanced vaccine-specific immune responses, May 13, 2011, $98^{th}$ Annual Meeting of the American Association of Immunologists, San Francisco, CA.
Grenfell et al., New approaches with different types of circulating cathodic antigen for the diagnosis of patients with low *Schistosoma mansoni* load, Feb. 28, 2013, *PLOS Negl. Trop. Dis*. 7(2):e2054.
Grenfell et al., Newly established monoclonal antibody diagnostic assays for Schistosoma mansoni direct detection in areas of low endemicity, Jan. 31, 2014, *PLOS One* 9(1):e87777.
Grenfell et al., 2015, Vaccine Self-assembling Immune Matrix is a new delivery platform that enhances immune responses to rHBsAg in mice. *Clinical and Vaccine Immunology*. Accepted Manuscript Posted Online Jan. 21, 2015. 27 pages.
Hall, How to Vaccinate, Oklahoma Cooperative Extension Service, Division of Agricultural Sciences and Natural Resources, Publication No. 350 [retrieved on Mar. 11, 2014]. Retrieved from the Internet:<URL: http://dasnr22.dasnr.okstate.edu/docushare/dsweb/Get/Document-1587>; 4 pgs.
Hansen et al., 2013, "Immune clearance of highly pathogenic SIV infection." *Nature* 502(7469):100-104.
Harn, Donald A., The Effect of Helminth Infection on HIV-1 Vaccines, Grant Abstract, Grant No. AI071883 [online]. National Institute of Allergy and Infectious Diseases, project dates Jun. 19, 2009 to May 30, 2011 [retrieved on Mar. 11, 2014]. Retrieved from the Internet:<URL: http://projectreporter.nih.gov/project_info_description.cfm?aid=7877043&icde=19607263>; 2 pgs.
Henriksson et al., 2011, "Investigation of different cell types and gel carriers for cell-based intervertebral disc therapy, in vitro and in vivo studies." *Journal of Tissue Engineering and Regenerative Medicine* 6:738-747.
Hess et al., A Guide to Aerosol Delivery Devices for Respiratory Therapists, May 2007 [retrieved on Mar. 11, 2014]. Retrieved from the Internet:<URL: http://hallowell.com/media/aerosol_delivery_guide.pdf>; 48 pgs.
Holmes et al., Extensive neurite outgrowth and active synapse formation on self-assembling peptide scaffolds, Jun. 2000, *Proceedings of the National Academy of Sciences of the USA* 97(12):6728-33.
Holmgren et al., A DNA vaccine targeting angiomotin inhibits angiogenesis and suppresses tumor growth, Jun. 2006, *Proceedings of the National Academy of Sciences of the USA* 103(24):9208-13.
Holyoake, Pig Vaccination Programs, Sep. 2009, Industry and Investment NSW, PrimeFact 944 [retrieved on Mar. 11, 2014]. Retrieved from the Internet:<URL: http://www.dpi.nsw.gov.au/_data/assets/pdf_file/0009/301500/Pig-vaccination-programs.pdf>; 2 pgs.
Horii et al., 2007, "Biological designer self-assembling peptide nanofiber scaffolds significantly enhance osteoblast proliferation, differentiation and 3-D migration." *PloS ONE* 2(2):e190. 9 pages.
Ingavle et al., 2014, "The bioactivity of agarose-PEGDA interpenetrating network hydrogels with covalently immobilized RGD peptides and physically entrapped aggrecan." *Biomaterials* 35(11):3558-3570.
Introduction. Product information [online]. 3DM Inc., Cambridge, MA [retrieved Apr. 2, 2012]. Retrieved from the internet: <URL: http://www.puramatrix.com/pr01.html>; 2 pgs.
Iwai et al., 2012, "A preliminary study of the dental implant therapy—initial osteogenesis of human mesenchymal stem (HMS0014) cells on titanium discs with different surface modifications." *Okajimas folia anatomica Japonica* 88(4):133-140.
Jorquera et al., 2013, "Nanoparticle vaccines encompassing the respiratory syncytial virus (RSV) G protein CX3C chemokine motif induce robust immunity protecting from challenge and disease." *PloS ONE* 8(9):e74905. 13 pages.
Jose et al., 2014, "Enhanced trophic factor secretion by mesenchymal stem/stromal cells with glycine-histidine-lysine (GHK)-modified alginate hydrogels." *Acta Biomaterialia* 10:1955-1964.
Kibler et al., 2011, "Improved NYVAC-based vaccine vectors." *PloS ONE* 6(11):e25674. 13 pages.
Kisiday et al., 2002, "Self-assembling peptide hydrogel fosters chondrocyte extracellular matrix production and cell division: implications for cartilage tissue repair." *Proc Natl Acad Sci USA* 99(15):9996-10001.
Kleinman et al., Matrigel: basement membrane matrix with biological activity, Oct. 2005, *Semin. Cancer Biol*. 15(5):378-86.
Kochenderfer et al., Vaccination regimens incorporating CpG-containing oligodeoxynucleotides and IL-2 generate antigen-specific antitumor immunity from T-cell populations undergoing homeostatic peripheral expansion after BMT, Jul. 2007, *Blood* 110(1):450-60 (published online Mar. 19, 2007).
Kossaczka et al., 1997 "Synthesis and Immunological Properties of Vi and Di-O-Acetyl Pectin Protein Conjugates with Adipic Acid Dihydrazide as the Linker" *Infection and Immunity* 65(6):2088-93.
Koutsopoulos et al., 2009, "Controlled release of functional proteins through designer self-assembling peptide nanofiber hydrogel scaffold." *Proc Natl Acad Sci USA* 106(12):4623-4628.
Kumar et al., Use of a recombinant *Burkholderia* Intracellular Motility A Protein for immunodiagnosis of glanders, Sep. 2011, *Clin. Vaccine Immunol*. 18(9):1456-61 (published online Jul. 13, 2011).
Le et al., A thermo-sensitive polymeric gel containing a gadolinium (Gd) compound encapsulated into liposomes significantly extended the retention of the Gd in tumors, Apr. 2008, *Drug Dev. Ind. Pharm*. 34(4):413-418.
Lee et al., 2011, "Dissolving microneedle patch for transdermal delivery of human growth hormone." *Small* (*Weinheim an der Bergstrasse, Germany*) 7(4):531-539.
Li et al., The therapeutic efficacy of angiostatin against weakly- and highly-immunogenic 3LL tumors, Nov.-Dec. 2002, In Vivo 16(6):577-82.
Lincoln, Cattle Vaccines and Their Use, 2009, Beef Cattle Handbook, Publication BCH-3015 [retrieved on Mar. 11, 2014]. Retrieved from the Internet: <URL: http://www.iowabeefcenter.org/Beef%20Cattle%20Handbook/Vaccines_Cattle.pdf>; 4 pgs.
Liu et al., In vivo studies on angiogenic activity of two designer self-assembling peptide scaffold hydrogels in the chicken embryo chorioallantoic membrane, Apr. 2012, *Nanoscale* 4(8):2720-27 (published online Mar. 5, 2012).
Lu et al., In vitro and in vivo degradation of porous poly(DL-lactic-co-glycolic acid) foams, Sep. 2000, *Biomaterials* 21(18):1837-45.

(56) References Cited

OTHER PUBLICATIONS

Mangsbo et al., CpG therapy is superior to BCG in an orthotopic bladder cancer model and generates CD4+ T-cell immunity, Jan. 1, 2008, *J. Immunother.* 31(1):34-42.
Marabelle et al., Depleting tumor-specific Tregs at a single site eradicates disseminated tumors, Jun. 3, 2013, *J. Clin. Invest.* 123(6):2447-63.
Maudlin, Small Flock Vaccination, Aug. 8, 2005, The Poultry Site [retrieved on Mar. 12, 2014]. Retrieved from the Internet: <URL: http://www.thepoultrysite.com/articles/377/small-flock-vaccination>; 4 pgs.
Ming et al., Immunization of aged pigs with attenuated pseudorabies virus vaccine combined with CpG oligodeoxynucleotide restores defective Th1 immune responses, Jun. 13, 2013, *PLOS One* 8(6):e65536.
Moingeon, Adjuvants for allergy vaccines, Oct. 2012, *Hum. Vaccin. Immunother.* 8(10):1492-98 (published online Oct. 1, 2012).
Mooney et al., Long-term engraftment of hepatocytes transplanted on biodegradable polymer sponges, Dec. 1997, *J. Biomed. Mater. Res.* 37(3):413-20.
Nagai et al., 2006, "Slow release of molecules in self-assembling peptide nanofiber scaffold." *J Control Release* 115(1):18-25.
National Center for Biotechnology Information, National Library of Medicine, National Institutes of Health, GenBank Locus AAC34263, Accession No. AAC34263, "H5 hemagglutinin, partial [Influenza A virus (A/HongKong/156/97(H5N1))]" [online]. Sep. 3, 1998, Bethesda, MD [retrieved on Apr. 8, 2014]. Retrieved from the Internet: <URL: http://www.ncbi.nlm.nih.gov/protein/AAC34263>; 1 pg.
National Center for Biotechnology Information, National Library of Medicine, National Institutes of Health, GenBank Locus ABO21709, Accession No. ABO21709, "hemagglutinin [Influenza A virus (A/Puerto Rico/8/1934(H1N1))]," [online]. May 1, 2008, Bethesda, MD [retrieved on Mar. 11, 2014]. Retrieved from the Internet: <URL: http://www.ncbi.nlm.nih.gov/protein/ABO21709>; 1 pg.
National Center for Biotechnology Information, National Library of Medicine, National Institutes of Health, GenBank Locus AFM72832, Accession No. AFM72832, "hemagglutinin [Influenza A virus (A/Califomia/07/2009(H1N1))]," [online]. Jun. 20, 2012, Bethesda, MD [retrieved on Mar. 11, 2014]. Retrieved from the Internet: <URL: http://www.ncbi.nlm.nih.gov/protein/392357062>; 2 pgs.
Nazar et al., "Thermosensitive hydrogels for nasal drug delivery: the formulation and characterization of systems based on N-trimethyl chitosan chloride" European Journal of Pharmaceutics and Biopharmaceutics, 2011; 7:225-232.
Nishimura et al., Controlled release of insulin from self-assembling nanofiber hydrogel, PuraMatrix™: application for the subcutaneous injection in rats, Jan. 23, 2012, *E. J. Pharm. Sci*. 45(1-2):1-7 (published online Oct. 28, 2011).
Okada et al., "Anti-tumor activity of chemokine is affected by both kinds of tumors and the activation state of the host's immune system: implications for chemokine-based cancer immunotherapy" Biochem Biophys Res Comm, 2004; 31(7):68-76.
Ortinau et al., Effect of 3D-scaffold formation on differentiation and survival in human neural progenitor cells, Nov. 11, 2010, *Biomed. Eng. Online* 9:70.
Overview. Product information [online]. 3DM Inc., Cambridge, MA [retrieved Apr. 2, 2012]. Retrieved from the internet: <URL: http://www.puramatrix.com/tc01.html>; 2 pgs.
Oxenius et al., CpG-containing oligonucleotides are efficient adjuvants for induction of protective antiviral immune responses with T-cell peptide vaccines, May 1999, *J. Virol*. 73(5):4120-26.
Palmer et al., Aerosol delivery of virulent *Mycobacterium bovis* to cattle, 2002, *Tuberculosis* (*Edinb*.) 82(6):275-82.
Paterson, Yvonne J., Immunogenicity of HIV Proteins Delivered by Live Vector, Grant Abstract, Grant No. AI036657 [online]. National Institute of Allergy and Infectious Diseases, project dates Sep. 1, 1995 to Aug. 31, 2006 [retrieved on Mar. 11, 2014]. Retrieved from the Internet:<URL: http://projectreporter.nih.gov/project_info_description.cfm?aid=6840619&icde=19607489>; 2 pgs.
Peine et al., Efficient delivery of the toll-like receptor agonists polyinosinic:polycytidylic acid and CpG to macrophages by acetalated dextran microparticles, Aug. 5, 2013, *Mol. Pharm*. 10(8):2849-59 (published online Jun. 14, 2013).
Pollock et al., Interleukin-18 plays a role in both the alum-induced T helper 2 response and the T helper 1 response induced by alum-adsorbed interleukin-12, Feb. 2003, *Immunology* 108(2):137-43.
Powell et al., Beef Cattle Herd Health Vaccination Schedule, 2003, Arkansas Cooperative Extension Service, Little Rock, AR, Fact Sheet # FSA3009. Retrieved from the Internet:<URL: http://www.uaex.edu/publications/pdf/FSA-3009.pdf>; 2 pgs.
PuraMatrix™ Peptide Hydrogel. Product information [online]. BD Biosciences, San Jose, CA & Franklin Lakes, NJ [retrieved Apr. 13, 2011]. Retrieved from the internet: <URL: http://www.bdbiosciences.com/ptProduct.jsp?prodID=554005>; 3 pgs.
Queiroz et al., New vaccination delivery regimen drives enhanced, vaccine-specific immune responses, Abstract No. 155.13, Immunology 2011, $98^{th}$ Annual Meeting of the American Association of Immunologists, San Francisco, CA, May 13-17, 2011, available online at J. Immunol. 186(1_MeetingAbstracts):155.13 (first published online at the IMMUNOLOGY 2011 website on Apr. 18, 2011).
Queiroz et al., New vaccination delivery regimen drives enhanced vaccine-specific immune responses, Abstract No. 278, $60^{th}$ Annual Meeting American Society of Tropical Medicine and Hygiene, Philadelphia, PA, Dec. 4-8, 2011, published in Am. J. Trop. Med. Hyg. 85(6 Supp.):85.
Rerks-Ngarm et al., 2009, "Vaccination with ALVAC and AIDSVAX to prevent HIV-1 infection in Thailand." *N Engl J Med* 361(23):2209-2220.
Romieu-Mourez et al., Cytokine modulation of TLR expression and activation in mesenchymal stromal cells leads to a proinflammatory phenotype, Jun. 15, 2009, *J. Immunol*. 182(12):7963-73.
Rudra et al., A self-assembling peptide acting as an immune adjuvant, Jan. 2010, *PNAS* 107(2):622-627 (published online Dec. 22, 2009).
Rudra et al., 2012, "Self-assembled peptide nanofibers raising durable antibody responses against a malaria epitope". *Biomaterials* 33(27):6476-6484.
Sacks, 2014, "Vaccines against tropical parasitic diseases: a persisting answer to a persisting problem." *Nat Immunol* 15(5):403-405.
Schirmbeck et al., Adjuvants that enhance priming of cytotoxic T cells to a Kb-restricted epitope processed from exogenous but not endogenous hepatitis B surface antigen, Jul. 1999, *Int. Immunol*. 11(7):1093-1102.
Segers et al., 2007 "Local delivery of proteins and the use of self-assembling peptides" *Drug Discovery Today* 12(13/14):561-568.
Sexton et al., 2009, "A protective vaccine delivery system for in vivo T cell stimulation using nanoengineered polymer hydrogel capsules." *ACS Nano* 3(11):3391-3400.
Shakenraad et al., Biocompatibility of poly (DL-lactic acid/glycine) copolymers, 1991, *Clin. Mater*. 7(3):253-69.
Shollenberger et al., Successful vaccination of immune suppressed recipients using Listeria vector HIV-1 vaccines in helminth infected mice, Apr. 2013, *Vaccine* 31(16):2050-2056 (published online Mar. 5, 2013).
Siddiqui et al., "Schistosomiasis vaccines" Human Vaccines, 2011; 7(11):1192-7.
Slutter et al., "Dual role of CpG as immune modulator and physical crosslinker in ovalbumin loaded N-trimethyl chitosan(TMC) nanoparticles for nasal vaccination" Journal of Controlled Release, 2010; 148: 117-121.
Szu et al., 1994 "Synthesis and Some Immunologic Properties of an O-Acetyl Pectin [Poly(11->4)-C-D-GalpA]-Protein Conjugate as a Vaccine for Typhoid Fever" *Infection and Immunity* 62(12):5545-9.
Taniguchi et al., Reactivation of immune responses against *Mycobacterium tuberculosis* by boosting with the CpG oligomer in aged mice primarily vaccinated with *Mycobacterium bovis* BCG, Jun. 22, 2013, *Immun. Aging* 10(1):25.
Thornhoff et al., Compatibility of human fetal neural stem cells with hydrogel biomaterials in vitro, Jan. 2008, *Brain Res*. 1187:42-51 (published online Oct. 26, 2007).

(56) References Cited

OTHER PUBLICATIONS

Vaccines. Product List [online]. Merck Animal Health, Summit, NJ [retrieved on Apr. 4, 2012]. Retrieved from the Internet: <URL: http://www.merck-animal-health.com/species/pigs/vaccines.aspx>; 3 pgs.

Vitelli-Avelar et al., Strategy to assess the overall cytokine profile of circulating leukocytes and its association with distinct clinical forms of human Chagas disease, Nov. 2008, *Scand. J. Immunol.* 68(5):516-25 (published online Sep. 18, 2008).

Wang et al., Enhanced type I immune response to a hepatitis B DNA vaccine by formulation with calcium- or aluminum phosphate, Jan. 2000, *Vaccine* 18(13):1227-35.

Wang et al. "Novel Delivery Systems for Nasal Administration of Anthrax Vaccine" Dissertation from University of North Carolina, Chapel Hill. 2010.

Wang et al., In vitro and in vivo evaluations of human papillomavirus type 16 (HPV16)-derived peptide-loaded dendritic cells (DCs) with a CpG oligodeoxynucleotide (CpG-ODN) adjuvant as tumor vaccines for immunotherapy of cervical cancer, Jan. 2014, *Arch. Gynecol. Obstet.* 289(1):155-62 (published online Aug. 3, 2013).

Wickramasekara et al., Proteomics analyses of the opportunistic pathogen Burkholderia vietnamiensis using protein fractionations and mass spectrometry, 2011, *J. Biomed. Biotechnol.* 2011:701928 (published online Dec. 1, 2011).

Williams et al., Mathematical modelling of schistosomiasis japonica: comparison of control strategies in the People's Republic of China, May 2002, *Acta Trop.* 82(2):253-62.

Winckelmann et al., Administration of a Toll-like receptor 9 agonist decreases the proviral reservoir in virologically suppressed HIV-infected patients, Apr. 23, 2013, *PLOS One* 8(4):e62074.

Xia et al., CpG oligodeoxynucleotide as immune adjuvant enhances photodynamic therapy response in murine metastatic breast cancer, Aug. 7, 2013, *J. Biophotonics*, doi: 10.1002/jbio.201300072.

Xin et al., Systemic treatment with CpG-B after sublethal rickettsial infection induces mouse death through indoleamine 2,3-dioxygenase (IDO), Mar. 28, 2012, *PLOS One* 7(3):e34062.

Yang et al., A 3D model of ovarian cancer cell lines on peptide nanofiber scaffold to explore the cell-scaffold interaction and chemotherapeutic resistance of anticancer drugs, Feb. 1, 2011, *Int. J. Nanomedicine* 5:303-10.

Yen et al., PGE2-induced metalloproteinase-9 is essential for dendritic cell migration, Jan. 2008, *Blood*, 111(1):260-70 (published online Oct. 9, 2007).

Yokoi et al., Dynamic reassembly of peptide RADA16 nanofiber scaffold, Jun. 2005, *Proceedings of the National Academy of Sciences of the USA* 102(24):8414-9 (published online Jun. 2005).

Zhang et al., 2014, "Preparation of novel biodegradable pHEMA hydrogel for a tissue engineering scaffold by microwave-assisted polymerization." *Asian Pacific journal of Tropical Medicine* 7(2):136-140.

Zhou et al., Cellular immune response to an engineered cell-based tumor vaccine at the vaccination site, Feb. 2007, *Cell. Immunol.* 245(2):91-102.

Zustiak et al., 2013, "Hydrolytically degradable poly(ethylene glycol) hydrogel scaffolds as a cell delivery vehicle: Characterization of PC12 cell response." *Biotechnology Progress* 29(5):1255-1264.

\* cited by examiner

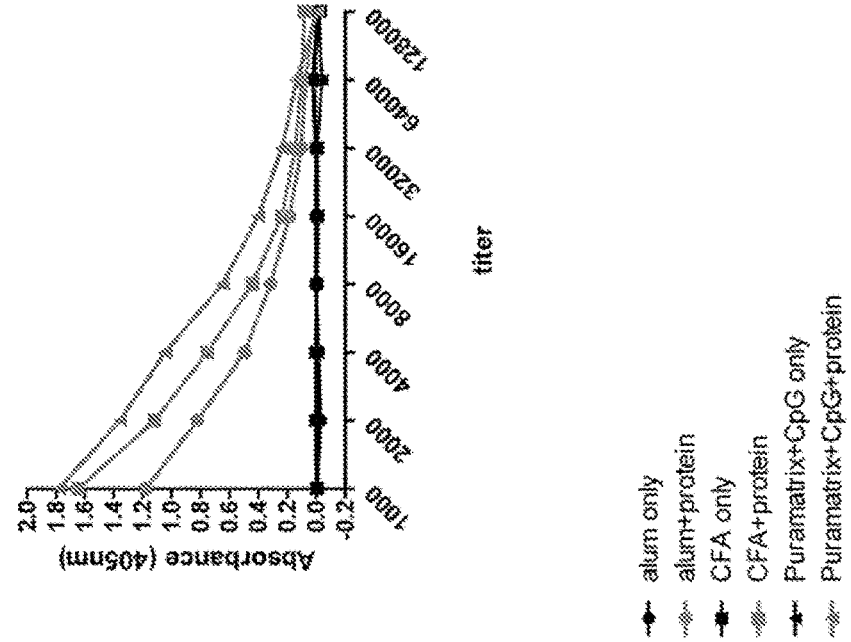
*Figure 21A*
*Figure 21B*
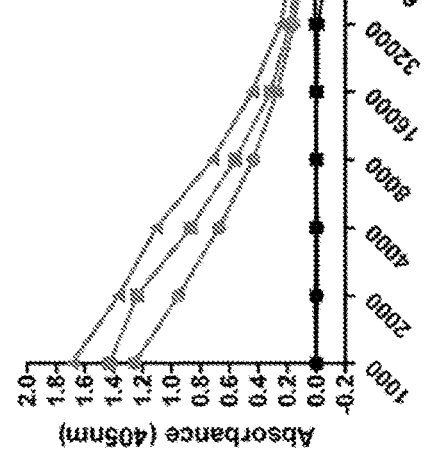
*Figure 21C*
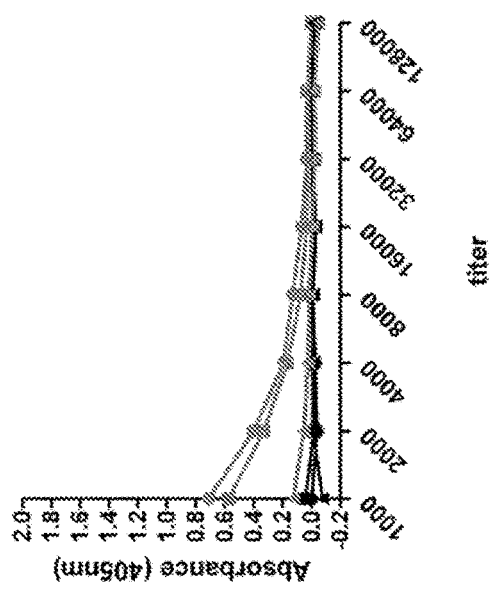

VACCINE DELIVERY METHOD

CONTINUING APPLICATION DATA

This application is a continuation application of U.S. patent application Ser. No. 15/411,083, filed Jan. 20, 2017, which is a continuation application of U.S. patent application Ser. No. 13/793,329, filed Mar. 11, 2013, which is a continuation-in-part of International Application No. PCT/US2012/034012, filed Apr. 18, 2012, which claims the benefit of U.S. Provisional Application Ser. No. 61/476,431, filed Apr. 18, 2011, all of which are incorporated by reference herein in their entireties.

GOVERNMENT FUNDING

This invention was made with government support under AI071883 and AI036657 awarded by the National Institutes of Health. The Government has certain rights in the invention.

SEQUENCE LISTING

This application contains a Sequence Listing electronically submitted via EFS-Web to the United States Patent and Trademark Office as an ASCII text filed entitled "23501840121 SequenceListing_ST25.txt" having a size of 17 kilobytes and created on Dec. 29, 2016. The information contained in the Sequence Listing is incorporated by reference herein.

BACKGROUND

Vaccines remain the single greatest public health asset for combating infectious diseases. The goal of vaccine delivery is to present vaccine antigens in a manner that enhances antigen presenting cell activation, uptake of antigen and processing. An additional goal is to reduce the number of vaccinations required to induce an effective, vaccine-specific response, especially if a single effective dose of a vaccine is available. Current, conventional vaccine delivery methods use alum. Aluminum salts, such as alum, were first licensed for use as adjuvants in human vaccines in the 1920's. There is a need for improved delivery modes and adjuvants that are safe for use in vaccine formulations.

SUMMARY OF THE INVENTION

The present invention includes a composition including as one component a slurry matrix that is a liquid at room temperature and a gel at physiological salt concentrations and/or physiological temperatures and as another component one or more antigens. In some aspects of the composition, the slurry matrix is a peptide hydrogel. In some aspects, the peptide hydrogel includes PURAMATRIX, or a derivative thereof. In some aspects, the peptide hydrogel includes the peptide scaffold RADARADARADARADA (SEQ ID NO:2), or a derivative thereof. In some aspects of the composition, the slurry matrix includes MATRIGEL, or a derivative thereof.

In some aspects of the composition, the composition further includes one of more adjuvants. In some aspects, an adjuvant includes a Toll-Like Receptor (TLR) agonist and/or a cytokine. In some aspects, a TLR agonist includes a TLR4 agonist. In some aspects, a TLR agonist includes a TLR9 agonist. In some aspects, a TLR9 agonist includes a CpG oligodeoxynucleotide (ODN).

In some aspects of the composition, the composition further includes a Toll-Like Receptor (TLR) agonist and/or a cytokine. In some aspects, a TLR agonist includes a TLR4 agonist. In some aspects, a TLR agonist includes a TLR9 agonist. In some aspects, a TLR9 agonist includes a CpG oligodeoxynucleotide (ODN).

In some aspects of the composition, the antigen includes a hepatitis antigen, an influenza antigen, a schistosomiasis antigen, and/or a burkolderia antigen, or an antigenic fragment thereof.

The present invention includes a method of producing an immune response in a subject, the method including administering a composition as described herein to the subject.

The present invention includes a method of immunizing a subject, the method including administering a composition as described herein to the subject.

The present invention includes a method of delivering one or more immunogenic antigens to a subject, the method including administering a composition as described herein to the subject.

The present invention includes a method of delivering one or more therapeutic antigens to a subject, the method including administering a composition as described herein to the subject.

In some aspects of the methods of the present invention, the subject is a domestic livestock or a companion animal. In some aspects of the methods of the present invention, the subject is poultry. In some aspects of the methods of the present invention, the subject is human.

In some aspects of the methods of the present invention, administration of the composition includes subcutaneous (sc) injection, intramuscular (im), intradermal, mucosal, intraperitoneal (ip), and aerosol delivery.

In some aspects of the methods of the present invention, administration of the composition includes administration as a primary and/or booster vaccination.

In some aspects of the methods of the present invention, administration of the composition includes administration as a booster vaccination after a primary vaccination with a polypeptide vaccine or a plasmid DNA vaccine.

The present invention includes a method of producing an anti-schistosome immune response in a bovoid, the method including administering a composition including as one component a slurry matrix that is a liquid at room temperature and is a gel at physiological conditions and as another component one or more schistosome antigens to the bovoid.

The present invention includes a method of producing an anti-schistosome immune response in a bovoid, the method including administering a composition as described herein to the bovoid, wherein one or more antigen includes a schistosome antigen.

The present invention includes a method of schistosomiasis vaccination in a bovoid, the method including administering a composition including as one component a slurry matrix that is a liquid at room temperature and is a gel at physiological conditions and as another component one or more schistosome antigens.

The present invention includes a method of schistosomiasis vaccination in a bovoid, the method including administering a composition as described herein to the bovoid, wherein one or more antigen includes a schistosome antigen.

In some aspects of the methods, the composition further includes one or more adjuvants. In some aspects, an adjuvant includes a Toll-Like Receptor (TLR) agonist and/or a cytokine. In some aspects, a TLR agonist includes a TLR4 and/or a TLR9 agonist. In some aspects, a TLR9 agonist includes a CpG oligodeoxynucleotide (ODN). In some aspects, a CpG ODN includes bovine CpG. In some aspects, the adjuvant includes the cytokine IL-12.

In some aspects of the methods, the composition further includes a Toll-Like Receptor (TLR) agonist and/or a cytokine. In some aspects, a TLR agonist includes a TLR4 and/or a TLR9 agonist. In some aspects, a TLR9 agonist includes a CpG oligodeoxynucleotide (ODN). In some aspects of the methods, a CpG ODN includes bovine CpG.

In some aspects of the methods, the schistosome antigen includes a *Schistosoma japonicum* antigen, or an antigenic fragment thereof.

In some aspects of the methods, the schistosome antigen includes is a SjCTPI polypeptide, a SjCTPI-Hsp70 polypeptide, a SjC23 polypeptide, and/or a SjC23-Hsp70 polypeptide, or an antigenic fragment thereof.

In some aspects of the methods, administration of the composition includes administration as a primary and/or a booster vaccination.

In some aspects of the methods, administration of the composition includes administration as booster vaccination after a primary vaccination with a SjCTPI-Hsp70 plasmid DNA vaccine.

In some aspects of the methods, the method further includes administration of one or more anti-schistosome chemotherapeutic agents.

In some aspects of the methods, the method demonstrates at least 45% efficacy in the prevention of infection with a schistosome parasite.

The present invention includes methods of making the composition described herein.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 14A presents TNF and IFN gamma. FIG. 14B presents IL-5 and IL-4. Each axis displays the proportion of each cytokine balance category. The values of each axis can be joined to form the central polygon area which represents the general cytokine balance. Increasing or decreasing central polygon areas reflect higher or lower contribution of inflammatory or regulatory cytokine balance in each group.

FIG. 16A presents data from 14 days, FIG. 16B presents data from 21 days, FIG. 16C presents data from 28 days, and FIG. 16D presents data from 35 days. Statistical significance at $P \leq 0.05$ are represented by superscript letters 'a', 'b' and 'c' for comparisons with rHepBag, rHepBag in ALHYDROGEL® and rHepBag in Freund, respectively.

FIG. 17A presents data from 14 days, FIG. 17B presents data from 21 days, FIG. 17C presents data from 28 days, and FIG. 17D presents data from 35 days.

FIG. 18A shows titers in C57BL/6 mice. FIG. 18B shows titers in Balb/c mice. Sera were collected four weeks post-last vaccination (4wplv).

FIG. 19A and FIG. 19B represent results from two independent experiments. Sera were collected four weeks post-last vaccination (4wplv).

FIG. 20A shows results from an independent experiment with lethal challenge at 30 $LD_{50}$. FIG. 20B shows results from an independent experiment with lethal challenge at 1000 $LD_{50}$.

FIGS. 21A to 21C show increased anti-burkholderia IgG titers in mice immunized with a cocktail of three recombinant burkholderia protein antigens with three different adjuvants (alum, CFA, or PURAMATRIX® gel). FIG. 21A shows anti-burkholderia protein 4-9 IgG titers in immunized mice. FIG. 21B shows anti-burkholderia protein 22-11 IgG titers in immunized mice. FIG. 21C shows anti-burkholderia protein 42 IgG titers in immunized mice.

FIG. 23A shows a schematic of a standard method including a prime vaccination and a boost vaccination. Baseline corrected anti-NP endpoint titers at 6 weeks post vaccination are shown for both C57BL/6 (FIG. 23B) and BALB/C (FIG. 23C) strains of mice; *p<0.05, **p<0.01 using a 1-way ANOVA with Tukey's multiple comparison test.

FIG. 24A shows a schematic of a new vaccination delivery system including only a single vaccination. FIG. 24B and FIG. 24C show anti-PR8 endpoint titers at 4 weeks post vaccination; p<0.01, *p<0.001, ****p<0.0001 using a 1-way ANOVA with Bartlett's test for equal variances and Bonferroni's multiple comparison test.

FIG. 25A shows baseline corrected, influenza-specific IgG, sera titers at 4 weeks post-last vaccination. FIG. 25B baseline corrected, influenza-specific IgG endpoint titers at 4 weeks post-last vaccination. p<0.01, *p<0.001, ****p<0.0001 using a 1-way ANOVA with Bartlett's test for equal variances and Bonferroni's multiple comparison test.

FIG. 26A shows anti-influenza IgE baseline corrected endpoint titers. FIG. 26B shows anti-influenza IgA baseline corrected endpoint titers. FIG. 26C shows anti-influenza IgM baseline corrected endpoint titers. FIG. 26D shows anti-influenza IgG baseline corrected endpoint titers. *p<0.05, **p<0.01, compared to new method (PR8+X+CpG) using nonparametric 1-way ANOVA with Kruskal-Wallis and Dunns multiple comparison post-test.

FIG. 27A shows anti-influenza IgG-λ-1 baseline corrected endpoint titers. FIG. 27B shows anti-influenza IgG-2a baseline corrected endpoint titers. FIG. 27C shows anti-influenza IgG-2b baseline corrected endpoint titers. FIG. 27D shows anti-influenza IgG-3 baseline corrected endpoint titers. *p<0.05, p<0.01, *p<0.001, compared to new method (PR8+X+CpG) using nonparametric 1-way ANOVA with Kruskal-Wallis and Dunns multiple comparison post-test.

FIG. 28A shows percent body weight after lethal challenge at 1,000 $LD_{50}$. FIG. 28B shows body score after lethal challenge at 1,000 $LD_{50}$. FIG. 28C shows percent survival after lethal challenge at 1,000 $LD_{50}$; *p<0.05, ***p<0.001, compared to naive using Log rank (Mantel-Cox) with Gehan-Breslow-Wilcoxon test.

FIG. 29A shows a schematic of a method including vaccination with whole inactivated virus, lethal challenge at 4 weeks post vaccination, and clearance assessments at 1, 2, 3, and 5 days post challenge. FIG. 29B shows enhanced kinetics of viral clearance of PR8 from the lungs at 1, 2, 3, and 5 days post challenge following homologous lethal challenge at 1,000 $LD_{50}$; p<0.01, **p<0.0001 compared to naive at the same time point using two-way ANOVA.

FIG. 30A shows baseline corrected, influenza-specific IgG sera titers in lung homogenates at 1 day post-challenge. FIG. 30B shows influenza-specific IgG whole lung endpoint titers in lung homogenates at 1 day post-challenge.

FIG. 31A shows baseline corrected, influenza-specific IgA sera titers in lung homogenates at 1 day post-challenge. FIG. 31B shows influenza-specific IgA whole lung endpoint titers in lung homogenates at 1 day post-challenge.

FIG. 32A shows baseline corrected, anti-HA IgG HI-(A/Ca/07/09) sera titers in lung homogenates at 4 weeks post-vaccination with PR8 WIV. FIG. 32B shows endpoint anti-HA IgG HI-(A/Ca/07/09) sera titers in lung homogenates at 4 weeks post-vaccination with PR8 WIV.

FIG. 33A shows baseline corrected, broadly reactive Anti-HA IgG H5-(A/HK/156/97) sera titers in lung homogenates at 4 weeks post-vaccination with PR8 WIV. FIG. 33B shows endpoint anti-HA IgG H5-(A/HK/156/97) sera titers in lung homogenates at 4 weeks post-vaccination with PR8 WIV.

Figure 1:
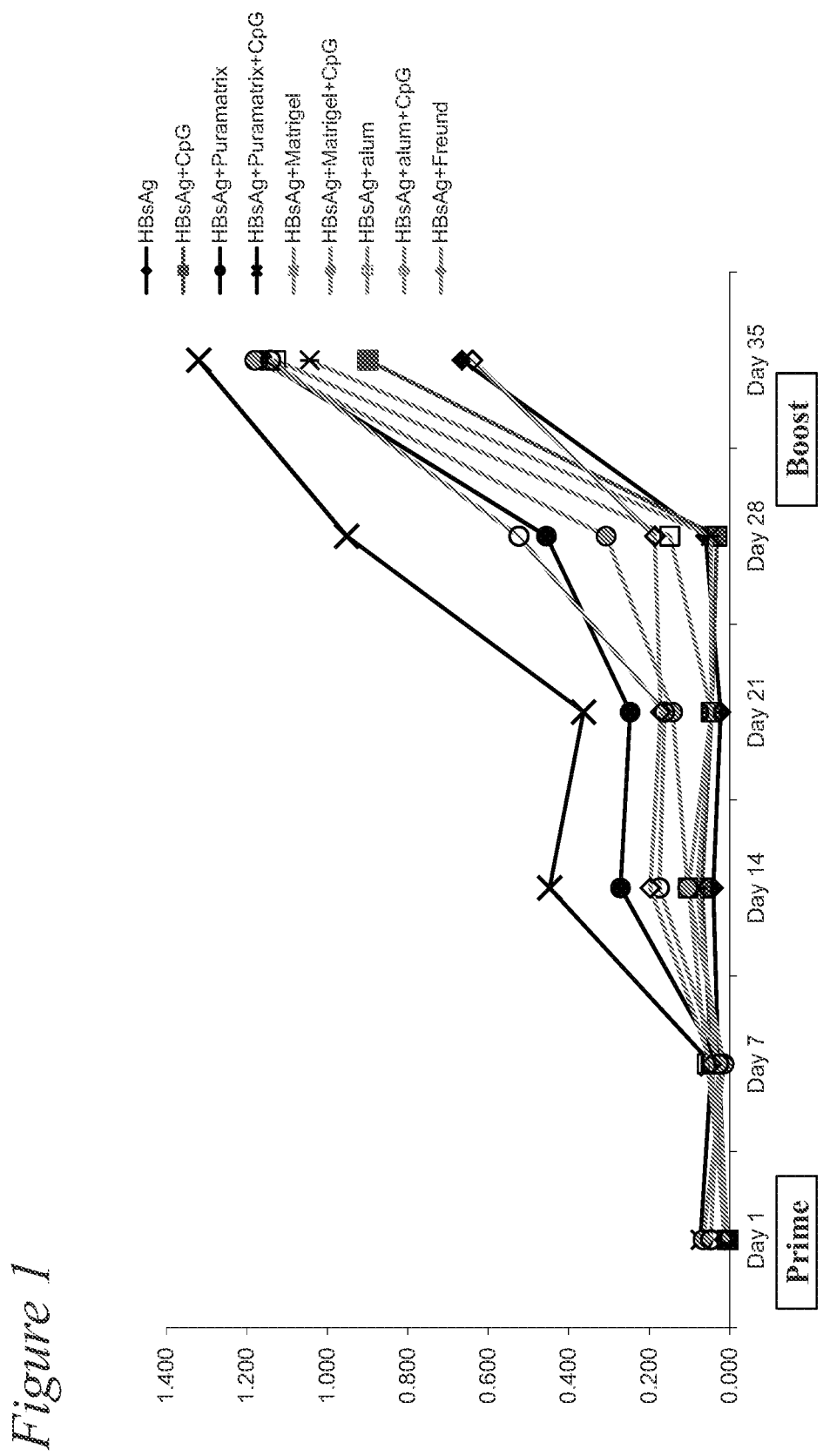
FIG. 1 shows the kinetics of IgA anti-HBsAg antibody titers. Data shown is pooled from two independent experiments for total n=10.

DETAILED DESCRIPTION OF ILLUSTRATIVE EMBODIMENTS OF THE INVENTION

The present invention provides compositions and methods that provide for improved vaccine delivery, providing for the improved focal and sustained delivery of antigen at the site of vaccine administration; enhancing antigen presenting cell activation and antigen uptake and processing. With the present invention, one or more immunogenic agents is administered in a composition including a slurry matrix component that is a liquid at room temperature, non-physiological pH, and/or low salt concentrations and a gel at physiological salt concentrations physiological pH, and/or physiological temperatures. Gelling may be induced by the physiological body temperature of a vertebrate, such as a mammal or bird. Such a temperature may be, for example, at least about 25° Celsius (C), at least about 30° Celsius, at least about 32° Celsius, at least about 35° Celsius, at least about 37° Celsius, at least about 39° Celsius, or at least about 40°. Gelling may be induced by the physiological salt concentrations. In some embodiments, gelling may in the presence of millimolar concentrations of salt, for example by a salt concentration of greater than about 0.05 molar (M). Gelling may be induced by the physiological pH of a vertebrate, such as a mammal or bird.

Thus, the vaccine composition gels or polymerizes after administration to a subject, localizing the vaccine antigens to a single site where innate antigen presenting cells can home and begin taking up vaccine antigens. Ideally, the slurry matrix is a biocompatible material will not induce undesirable reactions in the body as a result of contact with bodily fluids or tissue, such as tissue death, tumor formation, allergic reaction, foreign body reaction (rejection), inflammatory reaction, antibody response, or blood clotting, for example. A slurry matrix may also be referred to herein as a "biomedical polymer hydrogel," a "biomedical hydrogel," "biomedical polymer," a "polymer hydrogel," a "biocompatible polymer hydrogel," a "biocompatible hydrogel," a "biocompatible polymer," or a "hydrogel." As used herein, a "hydrogel" is a 3-dimensional network of cross-linked, hydrophilic macromolecules capable of being swelled and incorporating about 20 percent to about 95 percent water by weight. A hydrogel is a gel in which the liquid constituent is water. As used herein, a gel is a solid, jelly-like material that can have properties ranging from soft and weak to hard and tough. A gel is a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness). In this way gels are a dispersion of molecules of a liquid within a solid in which the solid is the continuous phase and the liquid is the discontinuous phase. Hydrogel is a network of polymer chains that are hydrophilic, sometimes found as a colloidal gel in which water is the dispersion medium. Hydrogels are highly absorbent (they can contain over 99.9% water) natural or synthetic polymers. Hydrogels also possess a degree of flexibility very similar to natural tissue, due to their significant water content.

Any of a wide variety of biomedical polymer hydrogels available for use in medical technologies may be used with the methods and compositions described herein.

In some embodiments, the slurry matrix is naturally occurring, such as for example, fibrin, collagen, elastin, agarose, methylcellulose, hyaluronan, and other naturally derived polymers. In some embodiments, the slurry matrix is MATRIGEL, or a derivative thereof. MATRIGEL is a basal membrane extract from mouse cells and includes laminin, collagen IV, entactin, nidogen, and proteoglycans. The invasion of tumor cells into MATRIGEL has been used to study the involvement of extracellular matrix receptors and matrix degrading enzymes in tumor progression and invasion and MATRIGEL has been used also as an in vitro and in vivo angiogenesis model (MATRIGEL plug assay) to study the activity of angiogenic and anti-angiogenic cytokines and other substances. MATRIGEL is commercially available as BD MATRIGEL™ Matrix. See the world wide web at bdbiosciences.com/cellculture/ecm/ecmtypes/index.jsp.

In some embodiments, a slurry matrix is synthetic, such as for example, a synthetic peptide hydrogel or a self-assembling peptide (sapeptide) scaffold. The sapeptide scaffolds are formed through the spontaneous assembly of ionic self-complementary beta-sheet oligopeptides under physiological conditions, producing a hydrogel material. These short peptides (typically about 8, about 12, about 16, about 24, or about 32 amino acid residues with internally-repeating sequences) self-assemble in aqueous salt solution into three-dimensional matrices. The peptides are characterized as being amphiphilic, having alternating hydrophobic and hydrophilic amino acid residues; greater than 12 amino acids, and preferably at least 16 amino acids; complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level. Examples include, but are not limited to, peptide family members, RAD16-I ((RADA)(4); SEQ ID NO:2), RAD16-II ((RARADADA)(2); SEQ ID NO:3), KFE-8 ((FKFE)(2); SEQ ID NO:4), or KLD-12 ((KLDL)(3); SEQ ID NO:5). See, for example, U.S. Pat. No. 5,670,483; Holmes et al., 2000, *Proc Natl Acad Sci USA;* 97(12):6728-33; Yokoi et al., 2005, *Proc Natl Acad Sci USA;* 102(24):8414-9; Liu et al., 2012, *Nanoscale;* 4(8):2720-7, and BD PURAMATRIX® Peptide Hydrogel, Guidelines for Use, Catalog Number 354250 (SPC-354250-G rev 2.0; BD Biosciences, Bedford, Mass.). In some aspects, a peptide hydrogel includes the peptide scaffold self-assembling building blocks of arginine-alanine-aspartate-alanine (RADA; SEQ ID NO:1). In some aspects, a peptide hydrogel includes RADARADARADARADA (SEQ ID NO:2), or a derivative thereof. In some aspects, the peptide hydrogel includes PURAMATRIX, or a derivative thereof. See, for example, U.S. Pat. No. 5,670,483; Holmes et al., 2000, *Proc Natl Acad Sci USA;* 97(12):6728-33; Yokoi et al., 2005, *Proc Natl Acad Sci USA;* 102(24):8414-9; Liu et al., 2012, Nanoscale; 4(8):2720-7, and BD PURAMATRIX® Peptide Hydrogel, Guidelines for Use, Catalog Number 354250 (SPC-354250-G rev 2.0; BD Biosciences, Bedford, Mass.), each of which are incorporated herein in their entireties.

In some embodiments, a biomedical polymer hydrogel may be a polyethylene glycol (PEG) hydrogel that polymerizes spontaneously in vivo.

In some embodiments, a slurry matrix, in addition to gelling at vertebrate or mammalian body temperature and/or physiological salt concentrations, is a bioresorbable synthetic polymer that degrades and dissolves with time. Such compounds are naturally degraded in the body by hydrolysis and absorbed as water-soluble monomers. Examples include, polylactic acid, polylactide (PLA), poly (L-lactic acid), poly-D-lactide, polyglycolic acid (PGA), polyglycolide and its copolymers (poly(lactic-co-glycolic acid) with lactic acid, homo- and copolymers of lactic acid and glycolic acid, poly (DL-lactic acid/glycine) copolymers, poly (DL-lacticco-glycolic acid) (PLGA), poly (DL-lacticco-glycolic acid) (PLGA), porous poly(DL-lactic-co-glycolic acid) foams, poly(amino acids) poly[ox(1-oxo-1,2-ethanediyl)] (($C_2H_2O_2$)$_n$; Biovek), poly(glycolide-co-caprolactone), poly (glycolide-co-trimethylene carbonate), polydioxanone (PDO, PDS), poly-p-dioxanone, caprolactone (also referred to as 2-oxepanone), epsilon-caprolactone, 6-hexanolactone, hexano-6-lactone, 1-oxa-2-oxocycloheptane polyglactin 910, polyanhydrides, and polyorthoester films formed from poly (D,L-lactic-co-glycolic acid, 88:12) (PLGA) or from a 50/50 (w/w) blend of PLGA and poly (L-lactic acid) (PLLA). See, for example, Schakenraad and Dijkstra, 1991, *Clin Mater;* 7(3):253-69; Mooney et al., 1997, *J Biomed Mater Res;* 37(3):413-20; and Lu et al., 2000, *Biomaterials;* 21(18):1837-45.

Compositions of the present invention include one or more antigenic agents (also referred to herein as an immunogen). An antigenic agent may be any of the great variety of agents that are administered to a subject to elicit an immune response in the subject. An antigenic agent may be an immunogen derived from a pathogen. The antigenic agent may be, for example, a peptide or protein antigen, a viral antigen or polypeptide, an inactivated virus, a recombinant virus, a bacterial or parasitic antigen, an inactivated bacteria or parasite, a whole cell, a genetically modified cell, a tumor associated antigen or tumor cell, a toxin, a lipid, a glycolipid, a glycoprotein, or a carbohydrate antigen. In some applications an antigen is not a living cell. In some embodiments, an antigenic agent is a soluble antigen.

A composition as described herein may include as an antigenic agent any of the great variety of immunogenic agents available as vaccine components. Such vaccines may include, but are not limited to, antigenic vaccines components directed against various infectious, viral, and parasitic diseases, toxins, and anti-tumor vaccine components. Anti-tumor vaccines include, but are not limited to, peptide vaccines, whole cell vaccines, genetically modified whole cell vaccines, lipid vaccines, glycolipid vaccines, glycoprotein vaccines, recombinant protein vaccines or vaccines based on expression of tumor associated antigens by recombinant viral vectors. In some embodiments, an antigenic agent is a soluble antigen.

As shown in Examples 8-11, the use of a composition as described herein in vaccination methods to deliver a vaccine antigen unexpectedly and surprisingly resulted in improved results, demonstrating significantly increased induction of specific antibodies, enhanced antibody titers, improved antibody isotype profiles, induction of a mixed Th1-Th2 response, increased protection from challenge, decreased morbidity following challenge, decreased mortality following challenge, and dramatically enhanced pathogen clearance.

An antigenic agent includes a bacterial or viral antigen from, for example, diptheria, *Streptococcus pneumoniae, Staphylococcus aureus, Bacillis anthracis* (such as, for example, PA), *Haemophilus influenzae, Kliebsiella pneumoniae, Escherichia coli, Psuedomonas aeruginosa, Moraxella catarrhalis, Coxiella burnetii, Mycoplasma pneumoniae, Legionella pneumophila, Chlamydophila pneumoniae, Yersinia pestis* and *Yersinia enterocolitica*, Hantavirus and other Bunyaviruses, Rhodococcus, Corynebacteria, adenovirus, parainfluenza, respiratory syncitial virus, coronavirus (SARS-CoV), varicella zoster virus, Herpes zoster, cytomegalovirus, cholera, enterotoxigenic *Escherichia coli*, enterohemorrhagic *Escherichia coli, Helicobacter pylori*, rotavirus, *Salmonella* spp., *Listeria*, Human immunodeficiency virus, Herpes virus, mumps, measles (paramyxovirus, Morbillivirus, Rubella), chicken pox, polio, sexually transmitted diseases (Chlamydia, gonorrhea, genital herpes, human papilloma virus, syphilis, bacterial vaginosis, Trichomoniasis, candidiasis, *Treponema pallidum*, tuberculosis (*Mycobacteria* spp.), rocky mountain spotted fever, Yellow fever, Dengue and other Flaviruses, Filoviruses such as Ebola and Marburg, babesia, viral hepatitis (Hepatitis A, B, C, E), *Clostridium botulinum, Francisella tularensis, Burkholderia pseudomallei* and *mallei, Brucella* species, Typhus Fever (*Rickettsia prowazecki*), Shigella species, *Cryptosporidium parvum*, Norwalk virus, Pathogenic Vibrios, Arenaviruses, *Campylobacter jejuni*, Caliciviruses, Microsporidia, Cyclospora spp., West Nile Virus, Lacrosse virus, California encephalitis virus, Venezuelan equine encephalitis, Eastern Equine encephalitis, Western Equine encephalitis, Japanese Encephalitis virus, Nipah Virus, Prions, Chikungunya virus, tickborne encephalitis viruses, tickborne hemorrhagic fevers viruses, influenza virus types A or B, seasonal and pandemic influenza vaccines.

An antigenic agent may be a toxin, such as, for example, ricin toxin from *Ricinus communis*, epsilon toxin from *Clostridium perfringens, Staphylococcus* enterotoxin B, aflatoxin from *Aspergillus flavus*, snake venoms, insect venoms, fish venoms, and plant toxins.

An antigenic agent may be an antigenic agent of a sexually transmitted disease (STD), such as for example, human immunodeficiency virus (HIV), herpes, and human papillomavirus (HPV).

An antigenic agent includes a parasite antigen from, for example, a malaria parasite or a schistosome parasite. Malaria antigens include, but are not limited to antigens from the plasmodium species *Plasmodium vivax, Plasmodium falciparum*, and *Plasmodium knowlesi, Plasmodium ovale*, and *Plasmodium malariae*. Schistosome parasites include, but are not limited to, *Schistosoma japonicum, Schistosoma mansoni*, and *Schistosoma haematobium*. A schistosome antigen may be a schistosome triose phosphate isomerase (CTPI) protein, or antigenic fragment or derivative thereof, including, but not limited to a *S. japonicum, S.*

*monsoni*, or *S. haematobium* CTPI protein, or antigenic fragment or derivative thereof. A schistosome antigen may be a schistosome tetraspin 23 kDa integral membrane protein (C23), or antigenic fragment or derivative thereof, including, but not limited to a *S. japonicum, S. monsoni*, or *S. haematobium* C23 protein, or antigenic fragment or derivative thereof. Such a schistosome antigen may be a chimeric polypeptide, fused to one or more additional antigenic determinants, such as for example, a heat shock protein, or antigenic fragment or derivative thereof, including, but not limited to, bovine heat shock protein 70 (Hsp70). Schistosome antigens include, for example, SjCTPI, SjCTPI-Hsp70, SjC23, and SjC23-Hsp70 polypeptides. Additional schistosome antigens include, for example, paramyosin, glutathione S-transferase, omega-1, fatty acid binding protein, molecules involved with binding to or transport of insulin, and sugars such as glucose, fatty acids, cholesterol, CAA, CCA.

Antigens may be from any of a variety of other parasites, including, but not limited to, kinetoplastid protozoa, such as for example, protozoa of the *Blastocrithidia, Crithidia, Endotrypanum, Herpetomonas, Leishmania, Leptomonas, Phytomonas, Trypanosoma*, and *Wallaceina* genera. In preferred embodiments, the protozoan is of the genus *Trypanosoma*, including, but not limited to, *T cruzi, T brucei, Tb. gambiense*, and *Tb. rhodesiense*. In some embodiments, the protozoan is of the genus *Leishmania*, including, for example, *Leishmania major*. Notable trypanosomal diseases include trypanosomiasis (African Sleeping Sickness and South American Chagas Disease, caused by species of *Trypanosoma*) and leishmaniasis (caused by species of *Leishmania*). In some embodiments, a viral antigen is, for example, toxoplasma, giardia, *Entamoeba* spp., schistosomiasis, onchocerchiasis, other filarial nematodes, gastroinstestinal nematodes such as ascaris, strongyloides, cestodes such as *Taenia* spp., and *Echinococcus* spp.

An antigenic agent includes a viral antigen from, for example, hepatitis, such as for example, hepatitis C, hepatitis B, or hepatitis A, influenza, for example, the M2, hemaglutinin, and/or neuraminidase proteins of an influenza virus, including, for example, influenza A (including, but not limited to, the H5N1 and H1N1 subtypes), influenza B, and influenza C, respiratory syncytial virus (RSV), rabies, papilloma virus, measles, rubella, varicella, rotavirus, polio, variscella zoster virus (VZV), and negative stranded RNA viruses, such as for example, a virus of the family Paramyxoviridae. Examples of a virus of the family Paramyxoviridae include, but are not limited to, human parainfluenza virus 1, human parainfluenza virus 2, human parainfluenza virus 3, human parainfluenza virus 4, parainfluenza virus 5, mumps virus, measles virus, human metapneumovirus, human respiratory syncytial virus, bovine respiratory syncytial virus rinderpest virus, canine distemper virus, phocine distemper virus, Newcastle disease virus, avian pneumovirus, Peste des Petits Ruminants virus (PPRV), Sendai virus, Menangle virus, Tupaia paramyxovirus, Tioman virus, Tuhokovirus 1, Tuhokovirus 2, Tuhokovirus 3, Hendravirus, Nipahvirus, Fer-de-Lance virus, Nariva virus, Salem virus, J virus, Mossman virus, and Beilong virus.

An antigenic agent may include one or more immunogens derived from pathogens infectious to poultry. Such immunogens may be derived from, for example, infectious bronchitis virus (IBV), Newcastle disease virus (NDV), Marek's disease (MDV), infectious bursal disease (IBD) virus, infectious laryngotracheitis (ILT), avian reovirus, cholera, fowl pox, mycoplasmosis, turkey and chicken Coryza, avian influenza, avian encephalomyelitis (AE), avian rhinotracheitis (ART), duck virus hepatitis, haemorrhagic enteritis, goose parvovirus, Paramyxovirus 3, chicken anaemia virus (CAV), *E. coli, Erysipelas, Reimerella, Mycoplasma gallisepticum, Pasteurella multocida, Salmonella enteritidis, Salmonella typhimurium*, coccidiosis, egg drop syndrome (EDS) virus, turkey rhinotracheitis virus (TRTV), and poxvirus.

An antigenic agent may include one or more immunogens derived from pathogens infectious to bovoids, including, but not limited to, domestic cattle, water buffalo, African buffalo, bison, and yaks. Such immunogens may be derived from, for example, bovine respiratory disease (BRD) vaccine, including, but not limited to BVDV types I and II, bovine herpes virus 1 (BHV-1) vaccine, including, but not limited to, subunit vaccines that would not result in latent virus, *Haemophilus somnus* vaccine, *Mannheimia haemolytica* vaccine, *Mycoplasma bovis* vaccine, bovine rotavirus vaccine, *Escherichia coli* K99 vaccine, bovine coronavirus (BCV) vaccine, *Clostridium chauvoei* (black leg) vaccine, *Clostridium septicum* vaccine, *Clostridium sordelli* (malignant edema) vaccine, *Clostridium novyi* (black disease) vaccine, *Clostridium perfringens* (enterotoxemia) vaccine, infectious bovine keratoconjunctivitis (pink eye) vaccine, including, but not limited to, *Moraxella bovis*, chlamydia, mycoplasma, acholeplasma, or infectious bovine rhinotracheitis (IBR) virus vaccines, mastitis vaccines, including, but not limited to, *Escherichia coli* J5 vaccine.

An antigenic agent may include one or more immunogens derived from pathogens infectious to swine, including, but are not limited to, porcine circovirus type 2 (PCV2), porcine reproductive and respiratory syndrome (PRRSV), respiratory mycoplasma, *Streptococcus suis*, porcine coronavirus, rotavirus, enterotoxigenic *Escherichia coli* (K88), *Actinobacillus pleuropneumonia* (APP), and swine influenza.

An antigenic agent may include one or more immunogens derived from the *Burkholderia* genus, a group of virtually ubiquitous gram-negative, motile, obligatory aerobic rod-shaped bacteria including both animal/human and plant pathogens as well as some environmentally important species. *Burkholderia* is best known for its pathogenic members. *Burkholderia mallei* is responsible for glanders, a disease that occurs mostly in horses and related animals. *Burkholderia pseudomallei* is the causative agent of melioidosis (also called Whitmore's disease), an infectious disease predominately of tropical climates that can infect humans or animals, especially in Southeast Asia and northern Australia. *Burkholderia cepacia* is an important pathogen of pulmonary infections in people with cystic fibrosis. Due to their antibiotic resistance and the high mortality rate from their associated diseases *Burkholderia mallei* and *Burkholderia pseudomallei* are considered to be potential biological warfare agents, targeting livestock and humans. Burkholderia antigens include, for example, any of three burkholderia recombinant proteins (the burkholderia 4-9 protein, the burkholderia 22-11 protein, and the burkholderia 42 protein). Such burkolderia antigens may be administered separately or as a cocktail of any two or three antigens.

An antigenic agent may be one or more of those currently used in the combination measles-mumps-rubella (MMR) and measles-mumps-rubella-varicella (MMRV) vaccines.

In some embodiments, the antigenic agent is a polynucleotide vaccine, that is, the antigenic agent is delivered as a vector construct, such as a plasmid, that results in the expression of a polypeptide antigen upon delivery to a subject. As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions. Any suitable vector or delivery vehicle may be utilized. Various vectors are publicly available. The vector may, for example, be in the form of a plasmid, cosmid, viral particle, or phage. A vector may be an expression vector. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to those of skill in the art.

A composition as described herein may be useful as a vaccine. The vaccine may be therapeutic, including, but not limited to, prophylactic or protective.

A composition of the present invention may include one or more compounds with adjuvant activity. Such an adjuvant stimulates the immune system and increases the response to a vaccine antigen, without having any specific antigenic effect in itself. An adjuvant acts to accelerate, prolong, or enhance antigen-specific immune responses when used in combination with specific vaccine antigens. Suitable compounds or compositions for this purpose include, but are not limited to, an aluminum based adjuvant, such as, for example, aluminum phosphate, aluminum hydroxide (also referred to as alum), aluminum hydroxyl-phosphate, and aluminum hydroxyl-phosphate-sulfate, and non-aluminum adjuvants, such as, for example, QS21, MF59, Lipid-A, neutral lipsomes, microparticles, a cytokine such as, for example, IL-12, plant oils, animal oils, oil-in-water or water-in-oil emulsion based on, for example a mineral oil, such as BAYOL F™ or MaARCOL 52™, Complete Freund's adjuvant, incomplete Freund's adjuvant, a vegetable oil such as, for example, vitamin E acetate, a saponin, squalene, a lipidated amino acid ("LAA"), and/or a TLR agonist.

In some embodiments, an adjuvant component is a toll-like receptor (TLR) ligand. TLRs in mammals were first identified in 1997. They constitute the first line of defense against many pathogens and play a crucial role in the function of the innate immune system. There are many known subclasses of Toll-like receptors, including, TLR1, TLR2, TLR3, TLR4, TLR5, TLR6, TLR7, TLR8, TLR9, TLR10, TLR11, TLR12, TLR13, TLR14, TLR15, and TLR16, and their ligands exhibit significant structural variation. A TLR agonist is a molecular ligand for one of the various Toll-like receptors (TLRs). Known TLRs include: TLR1 (TLR1 ligands include triacyl lipoproteins); TLR2 (TLR2 ligands include lipoproteins, gram positive peptidoglycan, lipoteichoic acids, fungi, and viral glycoproteins); TLR3 (TLR3 ligands include double-stranded RNA, as found in certain viruses, and poly I:C); TLR4 (TLR4 ligands include lipopolysaccharide and viral glycoproteins); TLR5 (TLR5 ligands include flagellin); TLR6 (TLR6 ligands include diacyl lipoproteins); TLR7 (TLR7 ligands include small synthetic immune modifiers (such as imiquimod, R-848, loxoribine, and bropirimine) and single-stranded RNA); TLR8 (TLR8 ligands include small synthetic compounds and single-stranded RNA); and TLR9 (TLR9 ligands include unmethylated CpG DNA motifs). Some TLR ligands are described herein, but it should be understood that such listings do not limit the invention in any way. TLR ligands are widely available commercially.

Preferred TLR agonists include TLR2 agonists, TLR4 agonists, TLR7 agonists, TLR8 agonists, and TLR9 agonists. TLR2 is involved in the recognition of a wide array of microbial molecules from Gram-positive and Gram-negative bacteria, as well as mycoplasma and yeast. TLR2 ligands include lipoglycans, lipopolysaccharides, lipoteichoic acids and peptidoglycans.

TLR4 recognizes Gram-negative lipopolysaccharide (LPS) and lipid A, its toxic moiety. TLR4 agonists include, but are not limited to, lipopolysaccharide (LPS), viral glycoproteins, monophosphoryl lipid A (MPL) (Anderson et al., 2010, *Colloids Surf B Biointerfaces;* 75(1):123-32), Glucopyranosyl Lipid Adjuvant-Stable Emulsion (GLA-SE) (Coler et al., 2010, *PLoS One;* 5(10):e13677), and the synthetic hexaacylated lipid A derivative, denoted as glucopyranosyl lipid adjuvant (GLA) (Coler et al., 2011, *PLoS One;* 6(1):e16333).

TLR9 is activated by unmethylated CpG-containing sequences, including those found in bacterial DNA or synthetic oligonucleotides (ODNs). Such unmethylated CpG containing sequences are present at high frequency in bacterial DNA, but are rare in mammalian DNA. Thus, unmethylated CpG sequences distinguish microbial DNA from mammalian DNA. A TLR9 agonist may be a preparation of microbial DNA, including, but not limited to, *E. coli* DNA, endotoxin free *E. coli* DNA, or endotoxin-free bacterial DNA from *E. coli* K12. A TLR9 agonist may be a synthetic oligonucleotide containing unmethylated CpG motifs, also referred to herein as "a CpG-oligodeoxynucleotide," "CpGODNs," "ODN," or "CpG." CpG ODNs are short, single stranded, DNA molecules that contain a cytosine ("C" nucleotide) followed by a guanine ("G" nucleotide). The "p" typically refers to the phosphodiester backbone of DNA. A TLR9 agonist of the present invention may include any of the at least three types of stimulatory ODNs have been described, type A, type B, and type C. CpG-oligodeoxynucleotides may be produced by standard methods for chemical synthesis of polynucleotides or purchased commercially. For example, CPG ODNs can be purchased through InvitroGen (San Diego, Calif.).

The compositions as described herein may include one or more cytokines. Cytokines may include, but are not limited to, IL-1α, IL-1β, IL-2, IL-3, IL-4, IL-6, IL-8, IL-9, IL-10, IL-12, IL-13, IL-15, IL-18, IL-19, IL-20, IFN-α, IFN-β, IFN-γ, tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), and or Flt-3 ligand. In some applications, one or more cytokines may serve as an adjuvant.

The present invention also includes methods of inducing an immune response in a subject by administering a composition as described herein to the subject. The immune response may or may not confer protective immunity. An immune response may include, for example, a humoral response and/or a cell mediated immune response. A humoral immune response may include an IgG (including IgG1, IgG2 (including IgG2a and/or IgG2b), IgG3, and/or IgG4), IgM, IgA, IgD, IgE, and/or IgY response. A cellular immune response may include T cell activation and/or cytokine production. The determination of a humoral or cellular immune response may be determined by any of a variety of methods known in the immunological arts, including, but not limited to, any of those described herein. The induction of an immune response may include the priming and/or the stimulation of the immune system to a future challenge with an infectious agent, providing immunity to future infections. The induction of such an immune response may serve as a protective response, generally resulting in a reduction of the symptoms. The immune response may enhance an innate and/or adaptive immune response. The immune response may demonstrate higher concentrations of antibodies with a single, primary immunization. The immune response may show altered immunoglobulin ratios and/or altered induction of inflammatory cytokines, type I interferons, and/or chemokines, compared to immunization without the slurry matrix. Such alteration may be an increase or a decrease. For example, a higher ratio of one isotype of immunoglobulin compared to another immunoglobulin isotype (for example, any one of IgM, IgA, IgD, IgG, or IgE compared to any one of IgM, IgA, IgD, IgG, or IgE) or a higher ratio of one IgG subclass compared to another IgG subclass (for example, any one of IgG1, IgG2a, IgG2b, IgG3, or IgG4 compared to any one of IgG1, IgG2a, IgG2b, IgG3, or IgG4) may be obtained.

The present invention also includes methods of vaccinating a subject by administering a composition as described herein to the subject. Such vaccination may result in a reduction or mitigation of the symptoms of future infection and may prevent a future infection. The compositions described herein may have therapeutic and/or prophylactic applications as immunogenic compositions in preventing and/or ameliorating infection, such that resistance to new infection will be enhanced and/or the clinical severity of the disease reduced. Such protection may be demonstrated by either a reduction or lack of the symptoms associated with RSS, including, but not limited to, any of those described herein. Any of a wide variety of available assays may be used to determine the effectiveness of the vaccination method of the present invention, including, but not limited to, any of those described herein.

In some applications, an immunologically effective amount of at least one immunogen is employed in such amount to cause a substantial reduction in the course of the normal infection. Immunogenicity and effectiveness may be assayed in any of a variety of known experimental systems, including, but not limited to, any of those described herein.

The compositions and methods described herein may be administered to a subject for the treatment and/or prevention of viral diseases, infectious diseases, including, but not limited to bacterial, fungal and parasitic infections, cancer, and other diseases in which the administration of one or more immunogens is therapeutically desired. With the methods of the present disclosure, the efficacy of the administration of one or more agents may be assessed by any of a variety of parameters known in the art, including, but not limited to, any of those described herein. This includes, for example, determinations of an increase in the delayed type hypersensitivity reaction to tumor antigen, determinations of a delay in the time to relapse of the post-treatment malignancy, determinations of an increase in relapse-free survival time, determinations of an increase in post-treatment survival, determination of tumor size, determination of the number of reactive T cells that are activated upon exposure to the vaccinating antigens by a number of methods including ELISPOT, FACS analysis, cytokine release, or T cell proliferation assays.

For example, the compositions and methods described herein may be administered to a patient for the treatment of cancer. Antitumor vaccines include, but are not limited to, peptide vaccines, whole cell vaccines, genetically modified whole cell vaccines, recombinant protein vaccines or vaccines based on expression of tumor associated antigens by recombinant viral vectors. Cancers to be treated include, but are not limited to, melanoma, basal cell carcinoma, colorectal cancer, pancreatic cancer, breast cancer, prostate cancer, lung cancer (including small-cell lung carcinoma and non-small-cell carcinoma), leukemia, lymphoma, sarcoma, ovarian cancer, Kaposi's sarcoma, Hodgkin's Disease, Non-Hodgkin's Lymphoma, multiple myeloma, neuroblastoma, rhabdomyosarcoma, primary thrombocytosis, primary macroglobulinemia, small-cell lung tumors, primary brain tumors, stomach cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, glioblastoma, adrenal cortical cancer, liver cancer, stomach cancer, oral cancer, cancer of the upper and lower airways, and head and neck. In some aspects, the cancer is a primary cancer. In some aspects, the cancer is metastatic. As used herein, "tumor" refers to all types of cancers, neoplasms, or malignant tumors found in mammals.

The efficacy of treatment of a cancer may be assessed by any of various parameters well known in the art. This includes, but is not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, determinations of tumor infiltrations by immune system cells, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation.

As used herein, unless the context makes clear otherwise, "treatment," and similar word such as "treated," "treating," etc., is an approach for obtaining beneficial or desired results, including and preferably clinical results. A treatment may include therapeutic and/or prophylactic treatments. Desirable effects of treatment include preventing occurrence or recurrence of disease, alleviation of symptoms, diminishment of one or more direct or indirect pathological consequences of the disease, decreasing the rate of disease progression, amelioration or palliation of the disease state, and remission or improved prognosis. In some applications, a composition as described may demonstrate an improvement in one or more desired results of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

As used herein, an "effective amount" or a "therapeutically effective amount" of a substance is that amount sufficient to affect a desired biological effect, such as beneficial results, including clinical results. Therapeutically effective concentrations and amounts may be determined for each application herein empirically by testing the compounds in known in vitro and in vivo systems, including any of those described herein. Dosages for humans or other animals may then be extrapolated therefrom. With the methods of the present invention, the efficacy of the administration of one or more interventions may be assessed by any of a variety of parameters well known in the art.

In some embodiments, an "effective amount" is an amount that results in a reduction of at least one pathological parameter. Thus, for example, an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not receiving treatment.

The present invention also includes methods of making and using the vaccine compositions described herein. The compositions of the present disclosure may be formulated in pharmaceutical preparations in a variety of forms adapted to the chosen route of administration. In some embodiments, the compositions of the present disclosure may be lyophilized.

Any of a variety of modes of administration may be used. For example, administration may be intravenous, topical, oral, intranasal, subcutaneous, intraperitoneal, intramuscular, intratumor, intradermal, mucosal, intrarectal, intravaginal, inhalation, or aerosol.

For aerosol or inhalation delivery, any of a variety of delivery modes may be used. For example, an inhaler (including, but not limited to, metered dose inhalers and dry powder inhalers), a nebulizer (including, but not limited to, air jet and ultrasonic nebulizers), or other aerosol delivery devise used in the treatment of respiratory illness and diseases may be used (see, for example, Hess et al., 2007, "A Guide to Aerosol Delivery Devices for Respiratory Therapists"). In some embodiments, a commercially available aerosol delivery system used for aerosol delivery to domestic animals and livestock may be used. See, for example, Palmer et al., 2002, *Tuberculosis (Edinb)*; 82(6):275-82. In some embodiments, delivery to domestic animals and livestock may be by aerosol spray. Such delivery may target delivery to the mucosal surfaces of the nasal passages and/or the lungs. Any of a variety of particle sizes may be delivered. Particle size may be heterodisperse (also termed polydisperse), meaning that there is a mix of sizes in the aerosol. Or, particle size may be monodisperse, with particles of a fairly uniform single particle size. Particle size plays an important role in lung deposition. As particle size increases above 3 μm, there is a shift in aerosol deposition from the lung periphery to the conducting airways. Oropharyngeal deposition also increases as particle sizes increase above 6 μm. Exhaled loss is high with very small particles of 1 μm or less. Thus, particle sizes of about 1-5 μm may be best for reaching the lung periphery, while particles of about 5-10 μm deposit preferentially in the conducting airways. (see Hess et al., 2007, "A Guide to Aerosol Delivery Devices for Respiratory Therapists"). For example, particles size may be selected to target the nose, to target oropharyngeal regions, to the conducting airways, to target the upper and central airways, to target the lower airways, to target the lung periphery, or a combination thereof.

For example, particles may be greater than about 10 μm in diameter, greater than about 6 μm in diameter, greater than about 5 μm in diameter, greater than about 3 μm in diameter, greater than about 2 μm in diameter or greater than about 1 μm in diameter. Particles may about 10 μm in diameter, about 6 μm in diameter, about 5 μm in diameter, about 3 μm in diameter, about 2 μm in diameter, about 1 μm in diameter, or any range thereof; for example, about 1 μm to about 10 μm in diameter, about 1 μm to about 6 μm in diameter, about 1 μm to about 5 μm in diameter, about 1 μm to about 3 μm in diameter, about 3 μm to about 5 μm in diameter, about 3 μm to about 6 μm in diameter, about 3 μm to about 10 μm in diameter, about 5 μm to about 6 μm in diameter, about 5 μm to about 10 μm in diameter, or about 6 μm to about 10 μm in diameter. Particles may be less than about 10 μm in diameter, less than about 6 μm in diameter, less than about 5 μm in diameter, less than about 3 μm in diameter, less than about 2 μm in diameter or less than about 1 μm in diameter. Particles may be about 10 μm or less in diameter, about 6 μm or less in diameter, about 5 μm or less in diameter, about 3 μm or less in diameter, about 2 μm or less in diameter or about 1 μm or less in diameter.

For aerosol delivery, a composition as described herein may be delivered in a lyophilized, dry, or a liquid state via an aerosolization devise. Once inhaled and encountering physiological pH in the airways and other mucosal sites, the materials would polymerize delivery the vaccine antigen(s), adjuvants, and additional components to the upper and lower airways.

For oral delivery, a composition as described herein may be administered, for example, in a capsule, in a liquid drink, or encapsulated in any form of digestible foods or materials. Encountering physiological pH in the gut, materials will form biopolymers and deliver the vaccine antigen(s), adjuvants, and additional components to the mucosal immune system.

For vaginal delivery a composition as described herein may be administered as a spray, wash or douche, or incorporated into a vaginal sponge or vaginal suppository. For intrarectal delivery a composition as described herein may be administered as a spray, wash, or douche, or incorporated into a sponge or rectal suppository. Encountering physiological pH in the vagina or rectum, materials will form biopolymers and deliver the vaccine antigen(s), adjuvants, and additional components to the mucosal immune system.

A vaccine composition as described herein may take the form of a patch or other vehicle for transdermal delivery. A vaccine composition as described herein may take the form of an implant. Such an implant may be implanted within the tumor. Delivery may be accomplished by any of a variety of available technologies, including, for example, injection, infusion, instillation, topical application, mucosal application, aerosol delivery, inhalation delivery delivery by a needle, and/or delivery by a catheter. Delivery may be by the use of a delivery device or tool, such as a needle, parch, catheter, or inhalation/aerosol devise. Such delivery devices are included in the present invention.

A composition of the present invention may be administered with one or more additional therapeutic interventions. Additional therapeutic treatments include, but are not limited to, surgical resection, radiation therapy, chemotherapy, hormone therapy, anti-tumor vaccines, antibody based therapies, whole body irradiation, bone marrow transplantation, peripheral blood stem cell transplantation, the administration of cytokines, antibiotics, antimicrobial agents, antiviral agents, such as AZT, ddI or ddC, the administration of chemotherapeutic agents, such as, for example, cyclophosphamide, methotrexate, 5-fluorouracil, doxorubicin, vincristine, ifosfamide, cisplatin, gemcitabine, busulfan, ara-C, adriamycin, mitomycin, cytoxan, methotrexate, and combinations thereof. Such administration may take place before, during, and/or after the administration of a vaccine composition as described.

As used herein, the term "subject" includes, but is not limited to, humans and non-human vertebrates. In some embodiments, a subject is a mammal, particularly a human. A subject may be an "individual," "patient," or "host." A subject may include, for example, a human, a higher primate, a non-human primate, domestic livestock and domestic pets (such as dogs, cats, cattle, horses, pigs, sheep, goats, mules, donkeys, mink, and poultry), laboratory animals (such as for example, mice, rats, hamsters, guinea pigs, and rabbits), and wild life. In some embodiments, a vaccine composition, as described herein is administered to a bovine, including, but not limited to, domestic cattle, water buffalo, African buffalo, bison, and yaks.

The vaccine compositions described herein may be administered to poultry, including, for example, chickens, turkeys, guinea fowl, partridges, and water fowl, such as, for example, ducks and geese. Chickens include, but are not limited to, hens, roosters, broilers, roasters, breeder, the offspring of breeder hens, and layers. The vaccine of the present invention may be administered to poultry before or after hatching. Poultry may receive a vaccine at a variety of ages. For example, broilers may be vaccinated in ovo, at one-day-old, in ovo, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Such laying stock or reproduction stock may be boosted at about 16, at about 17, at about 18, at about 19, or at about 20 weeks of age. The offspring of such laying stock or reproduction stock may demonstrate an antibody titer to the administered immunogen(s), which may prevent or mitigate the symptoms of an infection in the offspring.

The compositions of the present invention may be formulated according to methods known and used in the art. A vaccine composition of the present invention may include salts, buffers, preservatives, or other substances designed to improve or stabilize the composition. A vaccine composition may include a pharmaceutically acceptable excipient or carrier. As used herein, the term "pharmaceutically acceptable carrier" refers to a substance suitable for administration to a human or other vertebrate animal. For administration, a composition as described herein may be suitably buffered if necessary and the composition rendered isotonic with sufficient saline or glucose. In this connection, sterile aqueous media that can be employed will be known to those of skill in the art. Moreover, for human administration, preparations should meet sterility, pyrogenicity, and general safety and purity standards as required by the FDA. Such preparation may be pyrogen-free, may be sterile, and/or endotoxin-free.

A composition of the present invention may also contain one or more stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization. Such a composition may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water, aqueous buffer (such as buffered saline), alcohols, and polyols (such as glycerol).

Any of a wide variety of modulating agents may be included in the methods and compositions described herein. As used herein, a "modulating agent" is an agent that has a therapeutic effect on living tissue. Modulatory agents include, for example, therapeutic agents which are effective to prevent and/or overcome disease and/or promote recovery.

A composition of the present invention may be lyophilized.

The vaccine of the present invention may be administered to a subject by any of many different routes. For example, the vaccine may be administered intravenously, intraperitonealy, subcutaneously, intranasally, orally, transdermally, intradermally, intramuscularly, intravaginally, intrarectally, and via aerosol for inhalation delivery. Suitable dosing regimes may be determined by taking into account factors well known in the art including, for example, the age, weight, sex, and medical condition of the subject; the route of administration; the desired effect; and the particular conjugate and formulation employed. The vaccine may be administered as either a single does or multiple doses. When administered in a multi-dose vaccination format, the timing of the doses may follow schedules known in the art. For example, after an initial administration, one or more booster doses may subsequently me administered to maintain antibody titers and/or immunologic memory.

The methods of the present invention may include in vitro, ex vivo, or in vivo methods. As used herein "in vitro" is in cell culture and "in vivo" is within the body of a subject. With the present invention, an isolated immunogen or agent may be delivered. As used herein, "isolated" refers to material that has been either removed from its natural environment, produced using recombinant techniques, or chemically or enzymatically synthesized, and thus is altered "by the hand of man" from its natural state.

The present invention includes kits employing one or more of the compositions described herein. Such kits may provide for the administration of an immunogen to a subject in order to elicit an immune response. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The description exemplifies illustrative embodiments. In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein. All headings are for the convenience of the reader and should not be used to limit the meaning of the text that follows the heading, unless so specified.

EXAMPLES

Example 1

New Vaccination Delivery Regimen Drives Enhanced, Vaccine-Specific Immune Responses To enhance vaccine delivery over that seen when conventional delivery methods are used, this example focused on providing antigen, plus or minus CpG adjuvant, along with a component which is in liquid state at room temperature, but that forms a gel-depot under physiological conditions, after injection at 35° C. This allows for the antigen and adjuvant to be delivered in a concentrated form, enhancing antigen presenting cell activity, and leading to pro-inflammatory, vaccine-specific responses. Recombinant hepatitis B antigen (rHepBag) was used as the antigen for vaccination, and the delivery method evaluated along with seven different vaccine delivery schemes for the ability to induce Hepatitis B specific antibodies and cytokines. Mice were vaccinated with rHepBag in two different types of gel slurries (PURAMATRIX, also referred to herein as "P1," and MATRIGEL, also referred to herein as "P2"), or with rHepBag in ALHYDROGEL (aluminum salt) or rHepBAg mixed with Complete Freund's adjuvant (CFA). Gel slurries and ALHYDROGEL were mixed +/− with the murine CpG ODN 1826.

Results showed that mice vaccinated with either gel slurry plus ODN had significantly higher TNF production 24 to 48 hours after primary inoculation, while P1 was significantly superior to ALHYDROGEL at 24 hours. Adjuvant P2 presented a promising Th2 inhibition after 48 hours with the reduction of IL-4, IL-5 and IL-10 levels coincident with increased antigen-specific IgG2a production in serum.

The analysis of vaccine-specific antibodies showed that P1 drove high vaccine-specific IgA, IgM and IgG titers 14 days post-prime with or without using ODN and the high IgA and IgG titers was maintained for 35 days. As both of the gel slurry systems tested in this study was superior to the conventional adjuvants, this new gel slurry vaccine delivery system will have broad utility for enhancing responses to numerous current vaccines that are currently marginally functional. The use of this new vaccine delivery system will be further investigated in the development of vaccines for any of a wide variety of infectious diseases, from parasitic to viral infection.

Material and Methods

Vaccines and Route of Administration. The experimental vaccine used in this study was produced from a recombinant Hepatitis B antigen, namely, rHepBag (Fitzgerald Industries, Inc. Massachusetts, USA). 90 6- to 8-week-old female BALB/c mice were evenly divided into 9 groups and respectively received a prime subcutaneous injection (sc) on the back and, a boost 4 weeks later, of 0.1 ml solution containing 5 µg of rHepBag, 0.1 ml of 50 µg ODN 1826 (InvivoGen, Inc. California, USA) with 5 µg of rHepBag, 0.4 ml solution of PURAMATRIX (P1) and 5 µg of rHepBag with or without ODN 1826, 0.4 ml of MATRIGEL (P2) and 5 µg of rHepBag with or without ODN 1826, 0.1 ml solution of 250 µg alum (Thermo Fisher Scientific, Inc. Pennsylvania, USA) and 5 µg of rHepBag with or without ODN 1826 and, 0.1 ml of Complete Freund's Adjuvant (Sigma-Aldrich Co. Missouri, USA) with 5 µg of rHepBag (1:2). To prepare one dose of the slurry, 5 ug of rHBsAg antigen, with or without prior mixing with 50 ug CpG, was brought to a final volume of 400 ul with MATRIGEL or PURAMATRIX and mixed thoroughly before subcutaneous injection. Amounts were scaled up depending on the number of doses needed. MATRIGEL and PURAMATRIX were purchased from BD (Franklin Lakes, N.J.).

Cytokines and antibody evaluation. Splenocytes were isolated one week after boost for cytokines evaluation. Single cell suspensions ($1.5 \times 10^6$/ml) were prepared and suspended in 1640 medium (RPMI 1640 Thermo Scientific Hyclone, Utah, USA) with penicillin-streptomycin (final concentrations of 100 U/ml and 100 µg/ml respectively) (Sigma-Aldrich. St. Louis, Mo., USA). 0.5 ml of the single cell suspension was added to 48-well plates (Sigma-Aldrich. St. Louis, Mo., USA) with 0.5 ml of media, 0.5 ml of 1 µg/ml of Concanavalin A (ConA) or 0.5 ml of 5 µg/ml of rHepBag and cultured at 37° C. with 5% CO2. The levels of TNF were quantified after 24 and 48 hours culture, IL-4 and IL-5 after 48 hours, IL-4 and IL-10 after 72 hours, each in triplicate. The percentages of cytokine-positive mice were further transformed using a two-step platform that consisted of (1) to calculate the global median for each cytokine considering the whole range of values obtained for each group; and (2) to establish for each group the concept of 'low' and 'high'-cytokine producers using the global median percentage of cytokine-positive cells as the cut-off edge to segregate the individuals into two categories named as 'low' and 'high'-cytokine producers. It is important to highlight that the overall cytokine profile for each group was constructed by giving the same weight to all cytokines and producing cell populations.

IFN gamma ELISpot was also performed with $3 \times 10^5$ and $1.5 \times 10^5$ splenocytes after 24 hours of culture, as described by the manufacturer (BD Biosciences (San Francisco, Calif., USA) using 1 µg/ml of ConA as positive control. The spot-forming unit (SFU) value was expressed as mean of the triplicate cultures minus the mean value of its individual background.

Blood samples from mice were collected weekly from 1 to 6 weeks, including the day prior to the primary immunization. Sera collected from these bleeds were used in ULISA assays for the detection and quantification of antibodies.

Synthetic Peptides for T-cell analysis for flow cytometry. Synthetic peptides were synthesized by Biosynthesis, Inc., and were selected based on relevant literature. The S 228-39 peptide (IPQSLDSWWTSL; SEQ ID NO:6) is $H2-L^d$-restricted and the dominant epitope in Balb/c mice. The splenocytes from five mice per group were individually stimulated with 5 µM peptide and 40 U/ml IL-2 for flow cytometry.

Statistical analyses. For antibody evaluation, comparisons were analyzed by Mann-Whitney or Student's t test using GraphPad PRISM software, version 4.0 (GraphPad Software, California, USA), after Kolmogorov-Smirnov normality test. A difference was considered as statistically significant when a P-value was <0.05. Chi squared-test was used for comparisons of 'low' and 'high'-cytokine producers frequencies among groups and significance considered at P≤0.05. Comparison of radar graphs axes and polygon areas were considered significant for ratios two times lower in magnitude. Data analysis for the results presented in the radar chart format was performed by comparing the central polygon areas among cytokine-producers categories intra and inter groups. Significant differences were considered for ratios indicating axes and polygon areas two times lower or higher in size.

Results

Initial results showed mice vaccinated with either gel slurry plus CpGs had significantly higher vaccine-specific IgG2a 14 days after the prime, and IgA, IgM at 28 days post inoculation than mice vaccinated with alum or CFA. One gel slurry delivery drove significantly higher vaccine-specific IgG titers 14 days post-prime than the other delivery methods did post-boost, suggesting that the boost was unnecessary. Recall assays showed upregulated IL-10 and IL-4 from splenocytes of mice vaccinated with ALHYDROGEL or CFA compared to cells from gel-slurry+CpG vaccinated mice. CpG use reduced levels of IL-5 to background in all groups compared to elevated levels in CFA. No differences in levels of IFN or TNF were seen.

FIG. 1 shows the kinetics of IgA anti-HBsAg antibody titers. Data shown is pooled from two independent experiments for total n=10.

Figure 2:
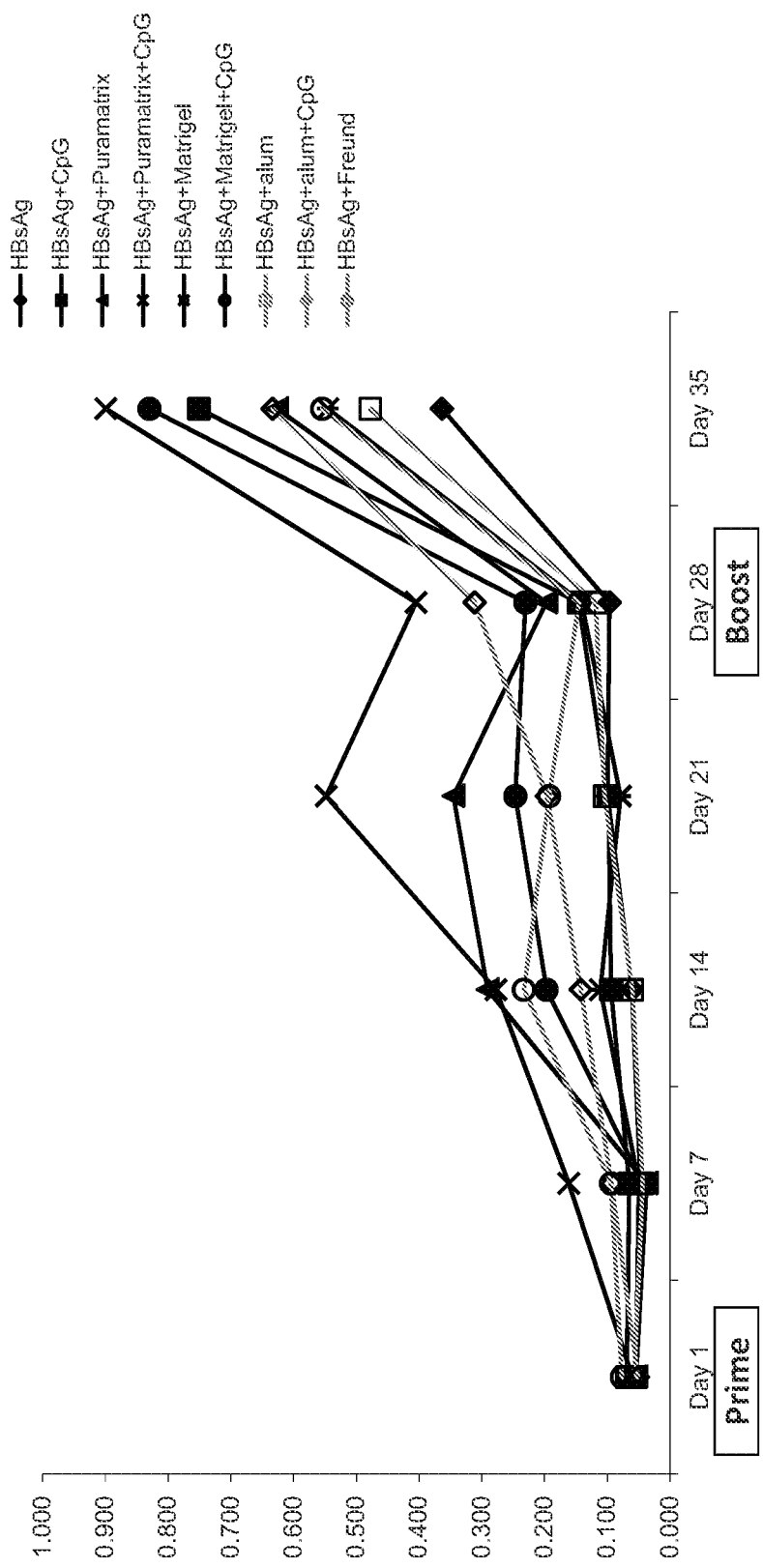
FIG. 2 shows the kinetics of IgM anti-HBsAg antibody titers. Data shown is pooled from two independent experiments for total n=10.

FIG. 2 shows the kinetics of IgM anti-HBsAg antibody titers. Data shown is pooled from two independent experiments for total n=10.

Figure 3:
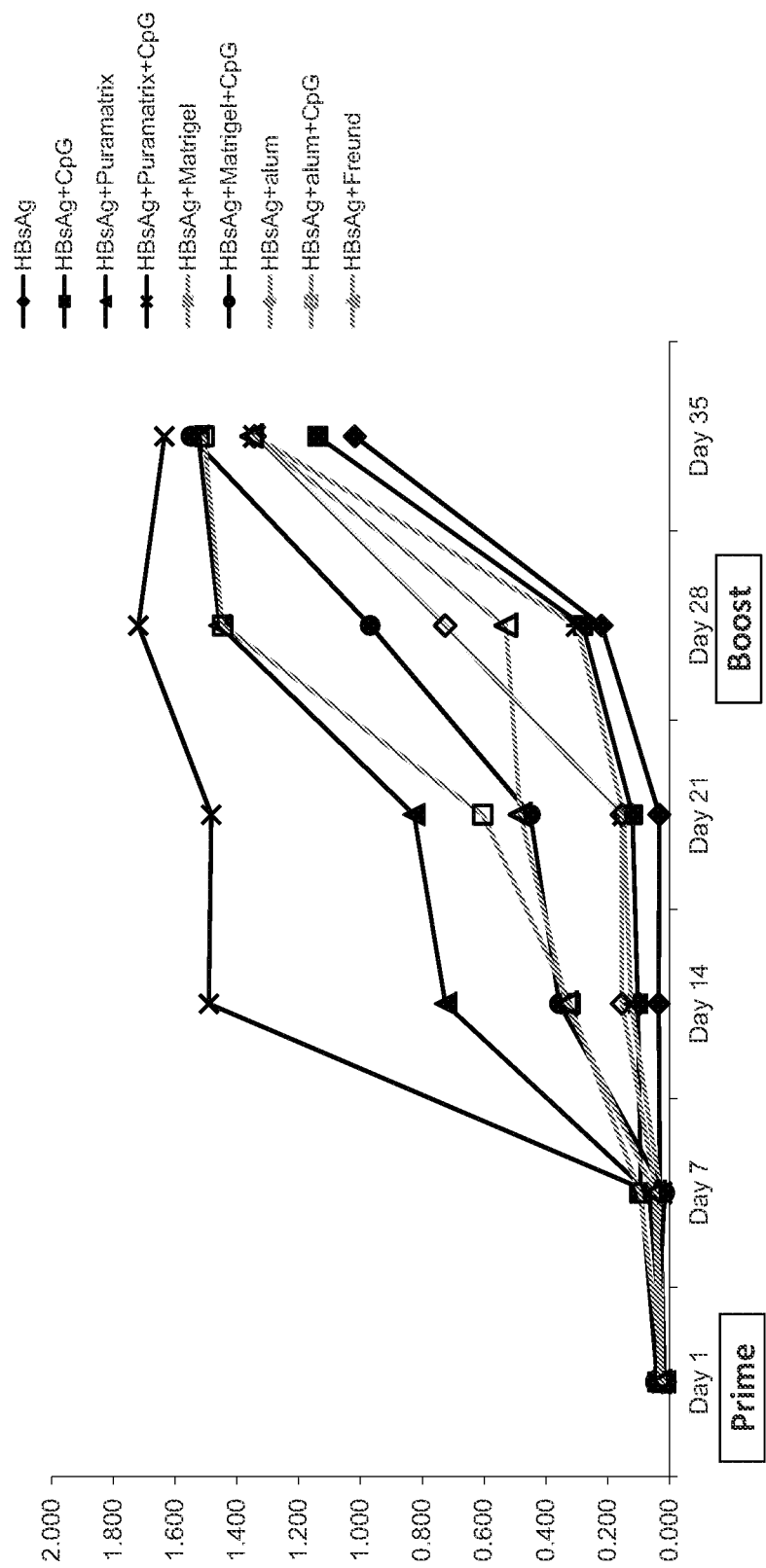
FIG. 3 shows the kinetics of IgG anti-HBsAg antibody titers. Data shown is pooled from two independent experiments for total n=10.

FIG. 3 shows the kinetics of IgG anti-HBsAg antibody titers. Data shown is pooled from two independent experiments for total n=10.

Figure 4:
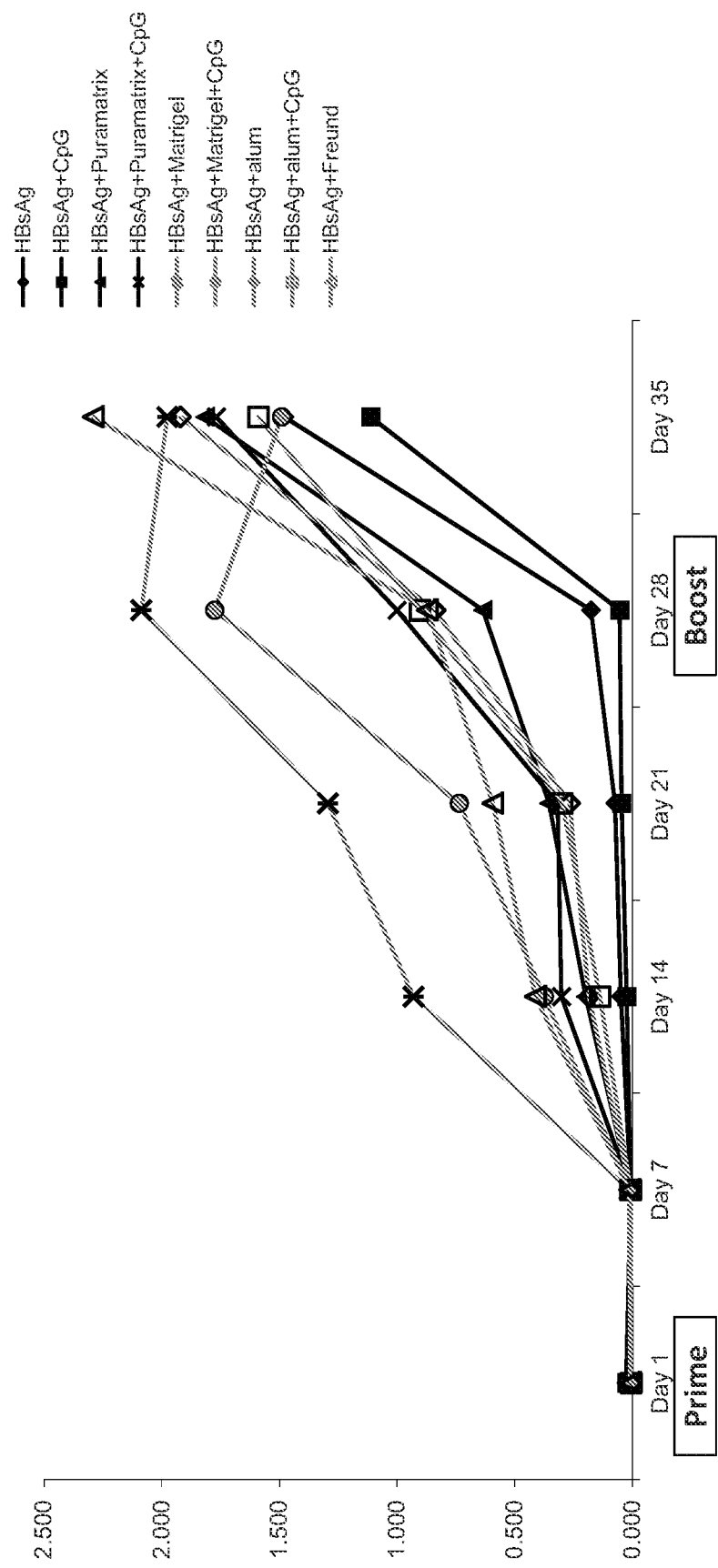
FIG. 4 shows the kinetics of $IgG_1$ anti-HBsAg antibody titers. Data shown is pooled from two independent experiments for total n=10.

FIG. 4 shows the kinetics of IgGi anti-HBsAg antibody titers. Data shown is pooled from two independent experiments for total n=10.

Figure 5:
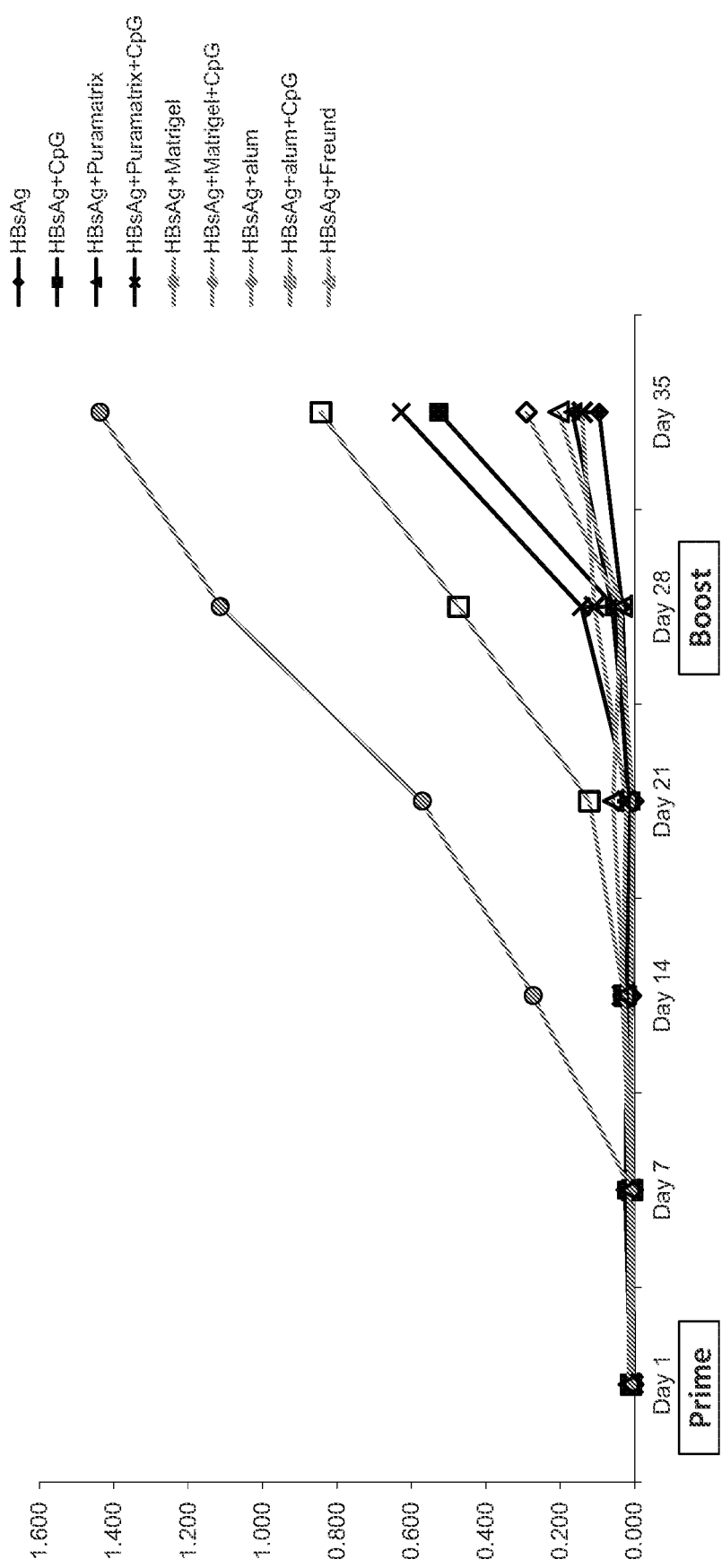
FIG. 5 shows the kinetics of IgG2a anti-HBsAg antibody titers. Data shown is pooled from two independent experiments for total n=10.

FIG. 5 shows the kinetics of IgG2a anti-HBsAg antibody titers. Data shown is pooled from two independent experiments for total n=10.

Figure 6:
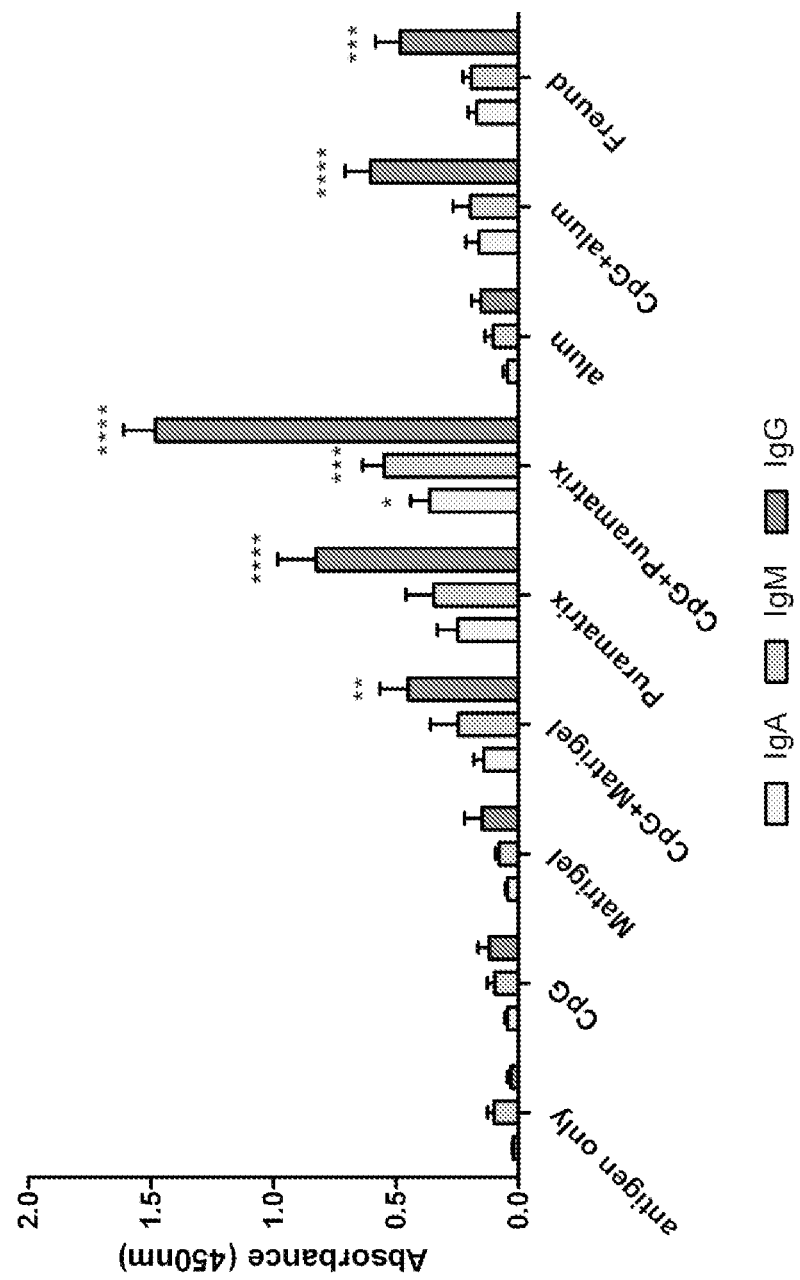
FIG. 6 shows higher anti-HBsAg antibody titers after single vaccination (21 days). Data shown is pooled from two independent experiments for total n=10; *$p<0.05$, $p<0.01$, $p<0.001$, ****$p<0.0001$ compared to antigen alone using two-way ANOVA with Bonferroni post-test.

FIG. 6 shows higher anti-HBsAg antibody titers after single vaccination (21 days). Data shown is pooled from two independent experiments for total n=10; *p<0.05, p<0.01, p<0.001, ****p<0.0001 compared to antigen alone using two-way ANOVA with Bonferroni post-test.

Figure 7:
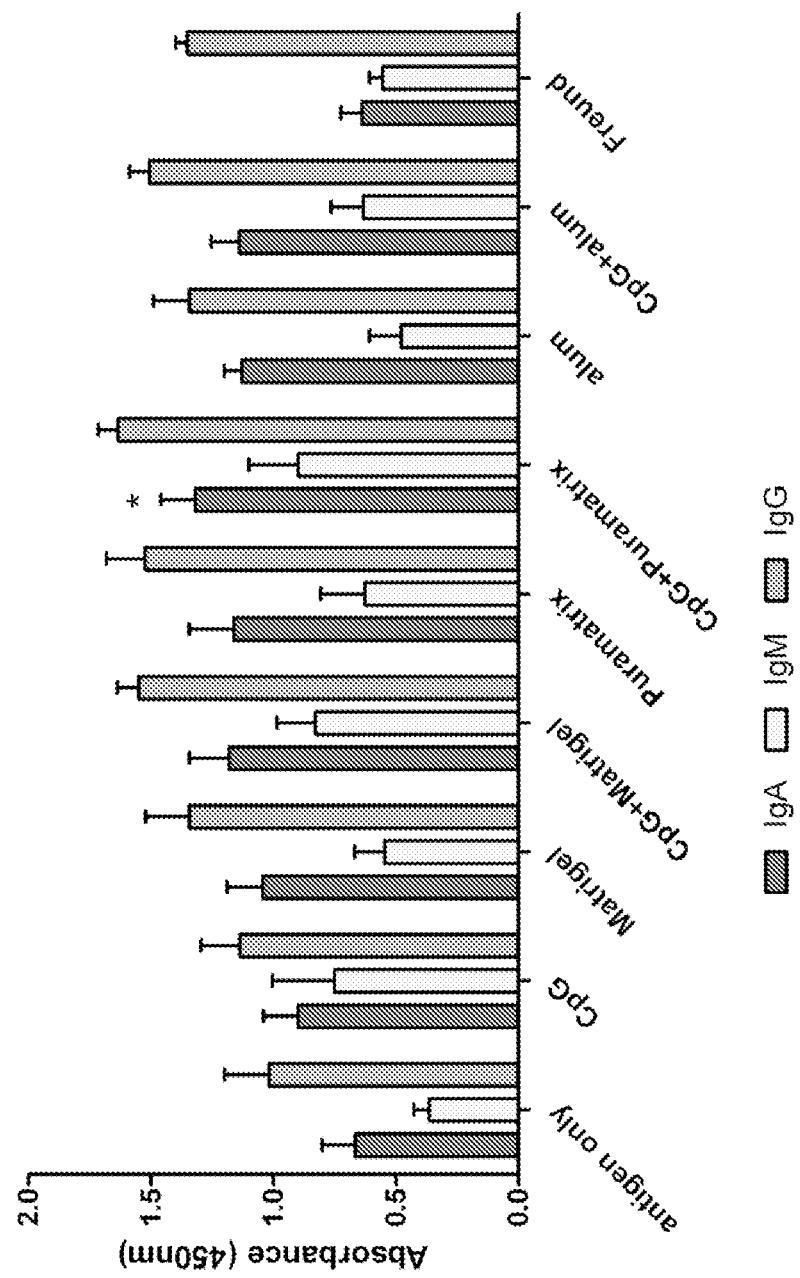
FIG. 7 shows higher anti-HBsAg antibody titers after single vaccination (35 days). Data shown is pooled from two independent experiments for total n=10; *$p<0.05$ compared to antigen alone using two-way ANOVA with Bonferroni post-test.

FIG. 7 shows higher anti-HBsAg antibody titers after single vaccination (35 days). Data shown is pooled from two independent experiments for total n=10; *p<0.05 compared to antigen alone using two-way ANOVA with Bonferroni post-test.

Figure 8:
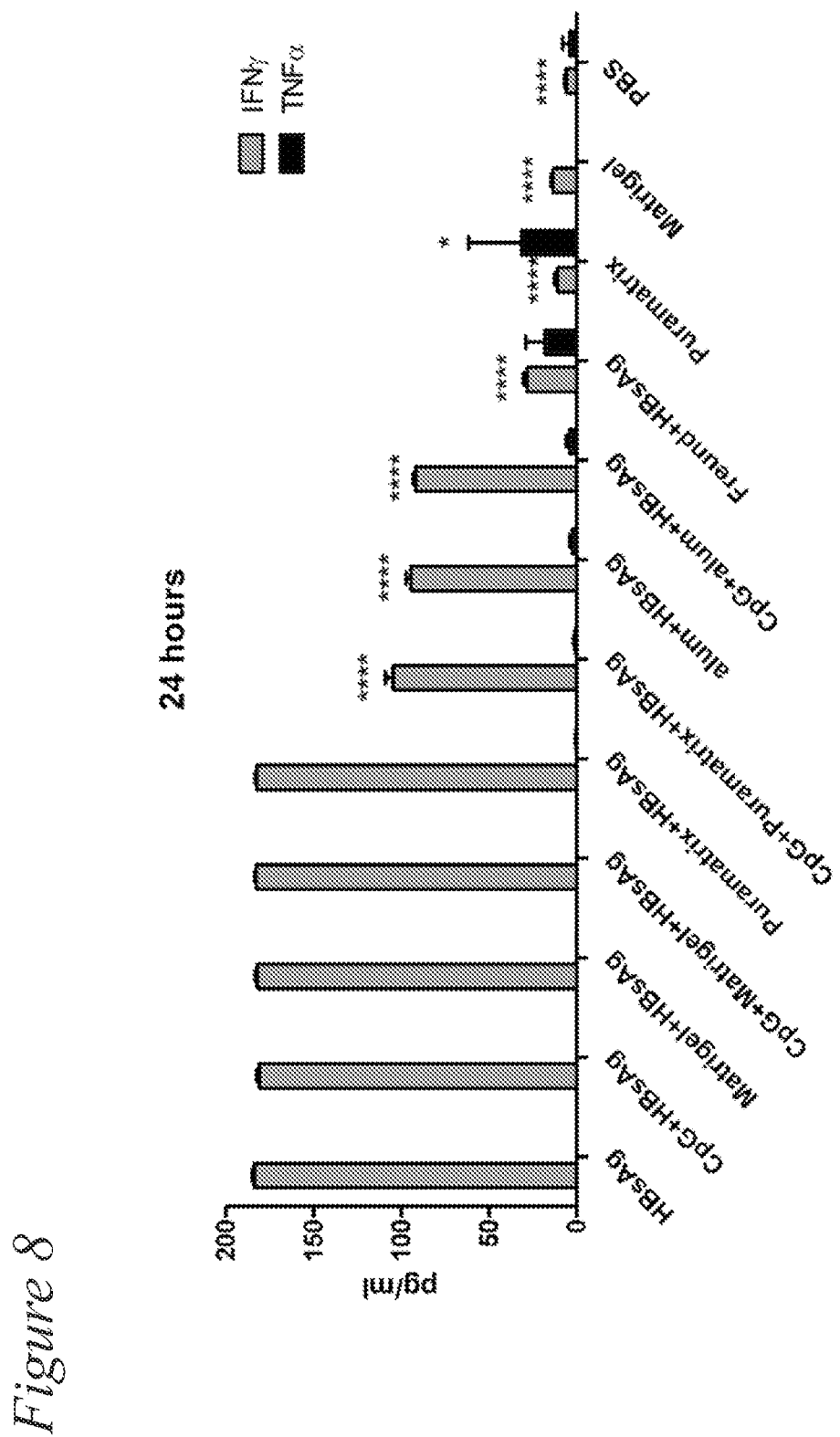
FIG. 8 shows cytokine profile twenty-four hours after HBsAg re-stimulation of splenocytes. Data shown is representative of one experiment, n=5; *$p<0.05$, ****$p<0.0001$ compared to antigen alone using two-way ANOVA with Bonferroni post-test.

FIG. 8 shows cytokine profile twenty-four hours after HBsAg re-stimulation of splenocytes. Data shown is representative of one experiment, n=5; *p<0.05, ****p<0.0001 compared to antigen alone using two-way ANOVA with Bonferroni post-test.

Figure 9:
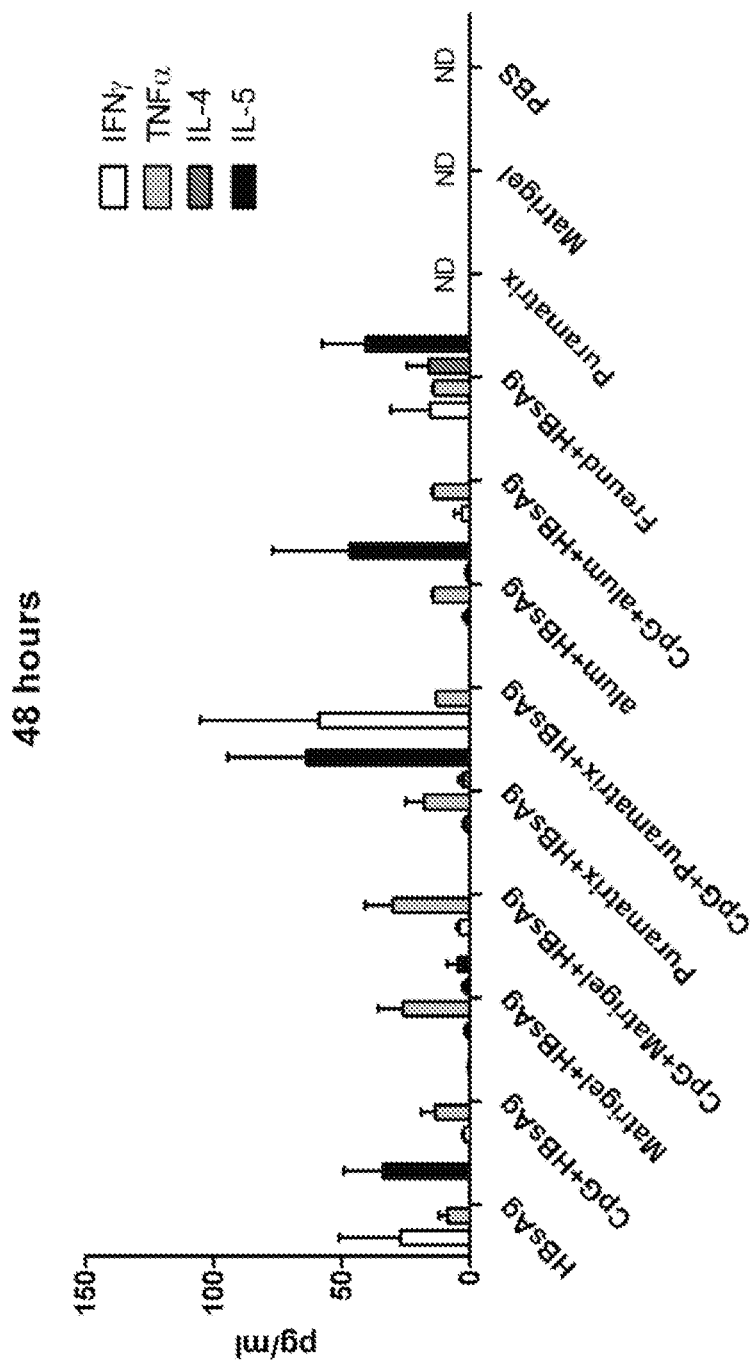
FIG. 9 shows cytokine profile forty-eight hours after HBsAg re-stimulation of splenocytes. Data shown is pooled from two independent experiments for total n=10 (n=5 for adjuvants only); no statistical differences seen ($p<0.05$) compared to antigen alone using two-way ANOVA with Bonferroni post-test.

FIG. 9 shows cytokine profile forty-eight hours after HBsAg re-stimulation of splenocytes. Data shown is pooled from two independent experiments for total n=10 (n=5 for adjuvants only); no statistical differences seen (p<0.05) compared to antigen alone using two-way ANOVA with Bonferroni post-test.

Figure 10:
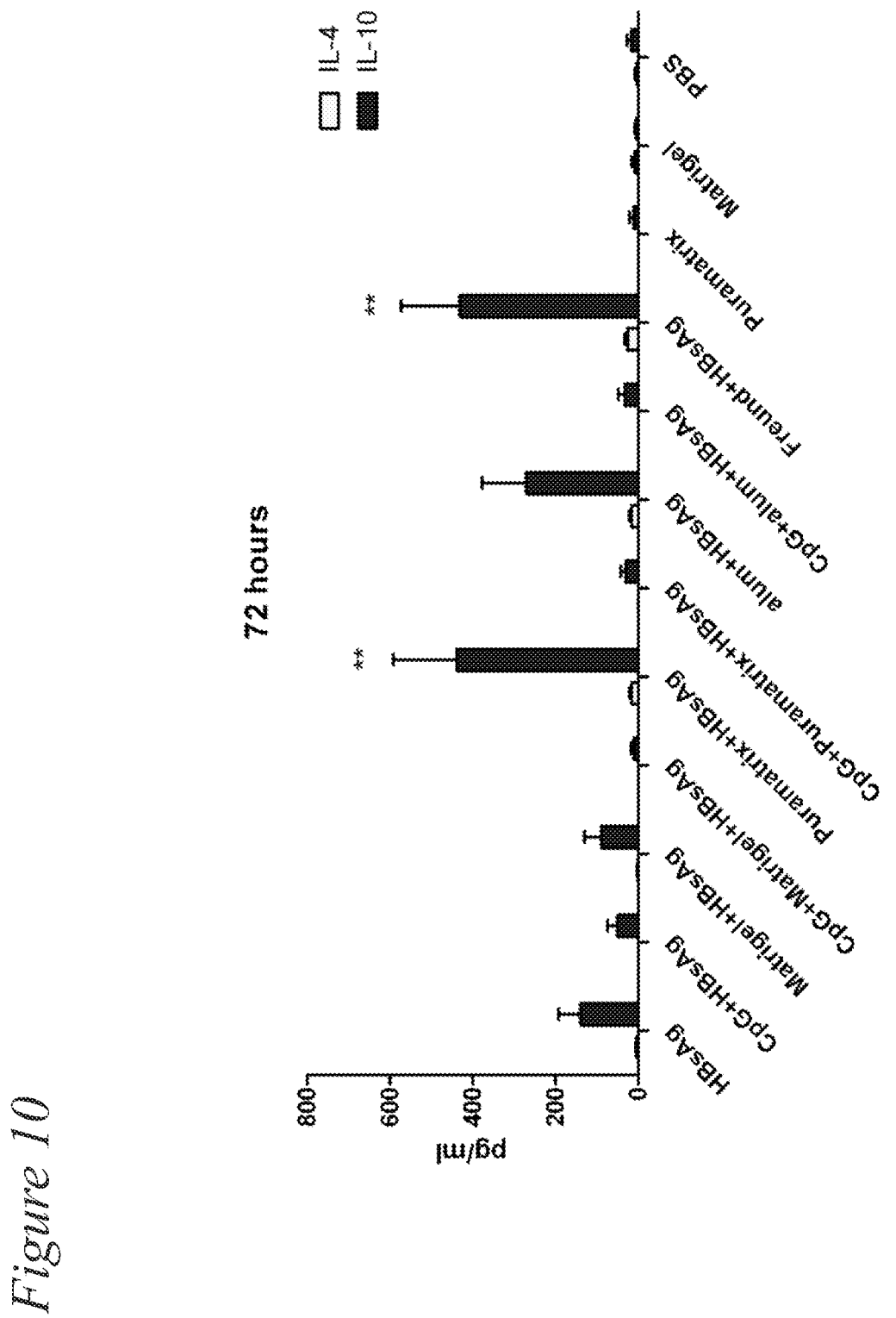
FIG. 10 shows cytokine profile seventy-two hours after HBsAg re-stimulation of splenocytes. Data shown is pooled from two independent experiments for total n=10 (n=5 for adjuvants only); **$p<0.01$ compared to antigen alone using two-way ANOVA with Bonferroni post-test.

FIG. 10 shows cytokine profile seventy-two hours after HBsAg re-stimulation of splenocytes. Data shown is pooled from two independent experiments for total n=10 (n=5 for adjuvants only); **p<0.01 compared to antigen alone using two-way ANOVA with Bonferroni post-test.

Figure 11:
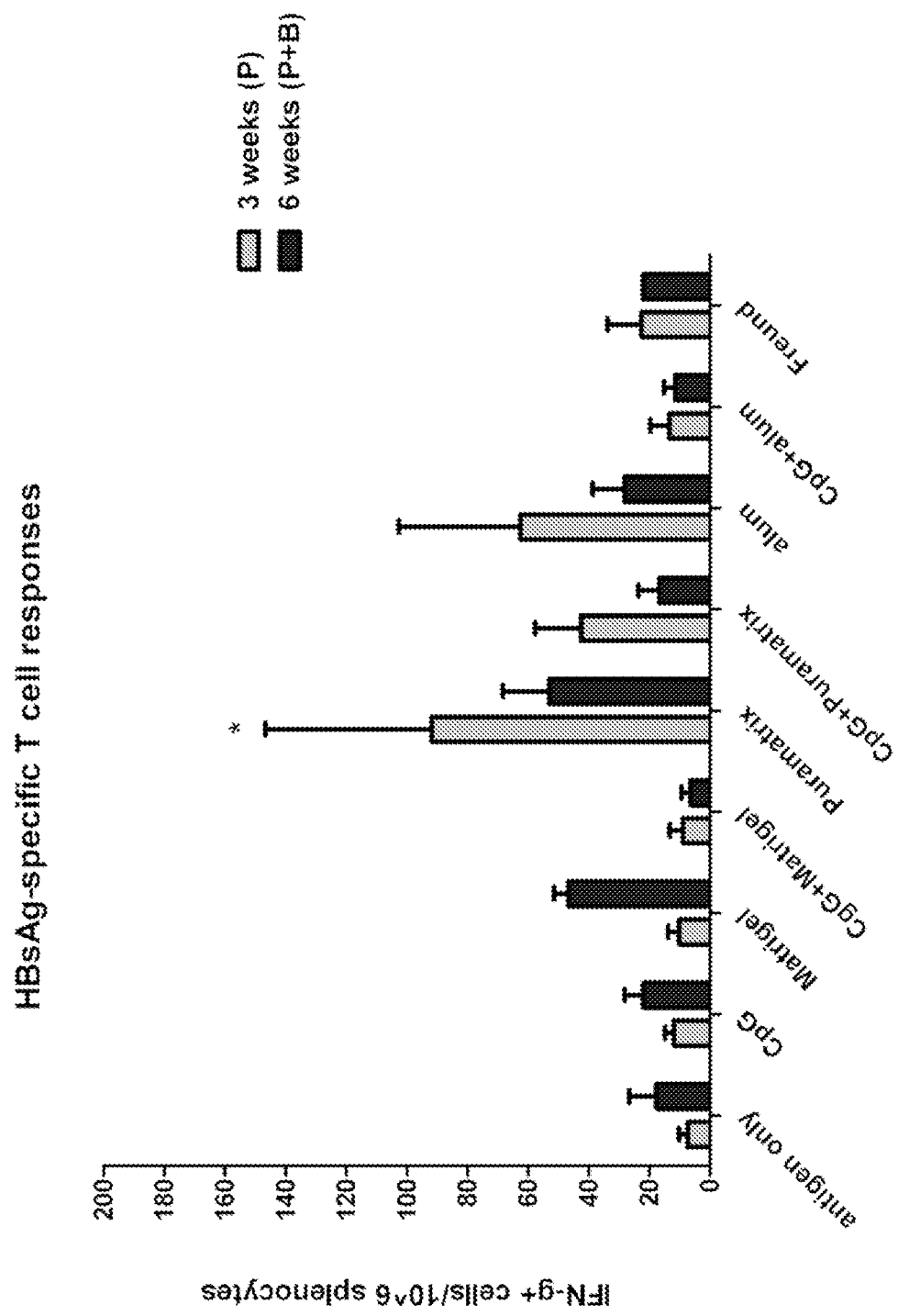
FIG. 11 shows increased HBsAg-specific cell-mediated immunity by ELISpot in HbsAg-specific T cell responses. Data shown is pooled from two independent experiments for total n=10; *$p<0.05$ compared to antigen alone using two-way ANOVA with Bonferroni post-test.

FIG. 11 shows increased HBsAg-specific cell-mediated immunity by ELISpot in HbsAg-specific T cell responses. Data shown is pooled from two independent experiments for total n=10; *p<0.05 compared to antigen alone using two-way ANOVA with Bonferroni post-test.

Figure 12:
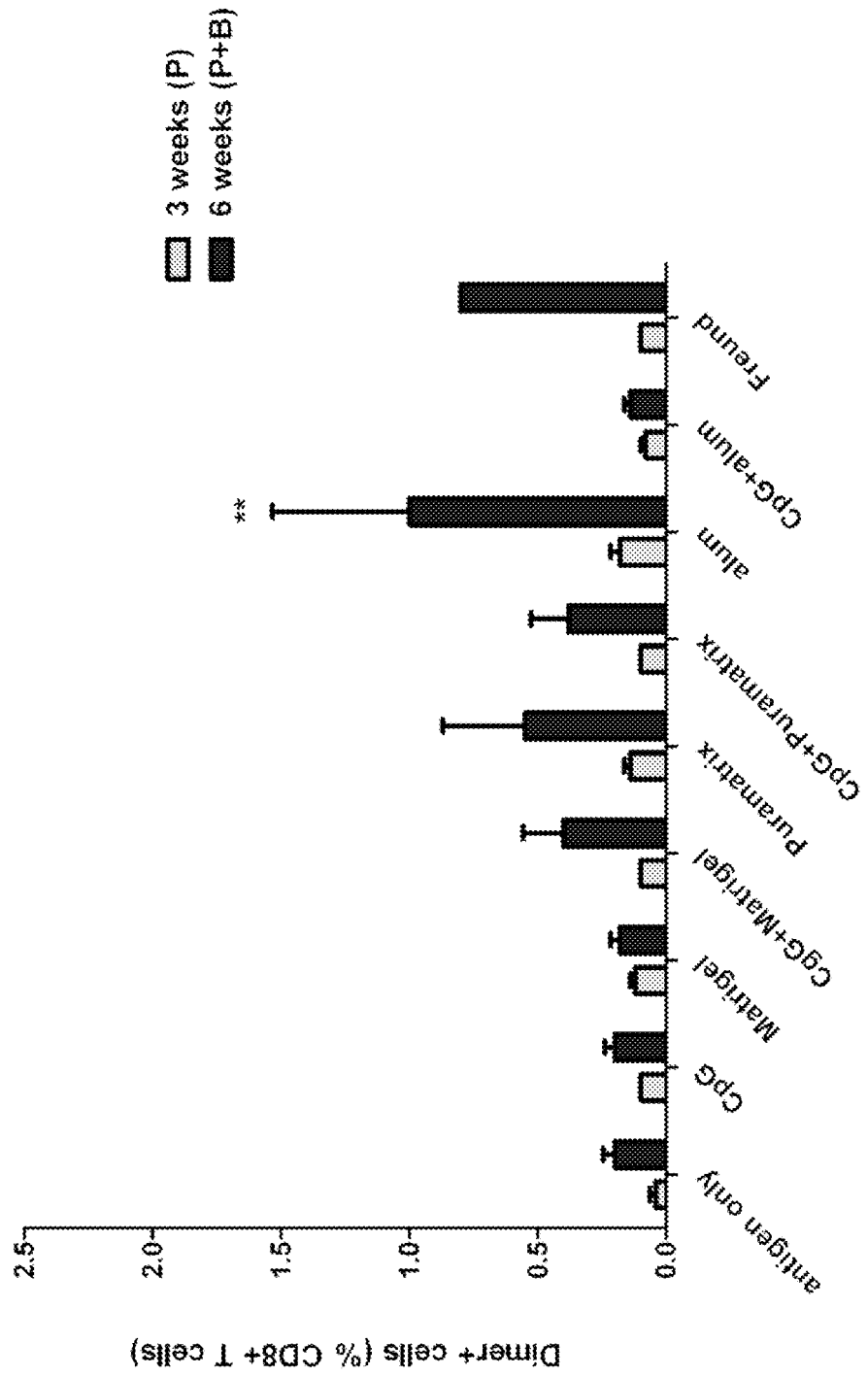
FIG. 12 shows increased HBsAg-specific T cell-mediated immunity by flow cytometry. Data shown is pooled from two independent experiments for total n=10; **$p<0.01$ compared to antigen alone using two-way ANOVA with Bonferroni post-test.

FIG. 12 shows increased HBsAg-specific T cell-mediated immunity by flow cytometry. Data shown is pooled from two independent experiments for total n=10; **p<0.01 compared to antigen alone using two-way ANOVA with Bonferroni post-test.

Increase of cytokines secretion by splenocytes with stimulation of rHepBag. In order to measure the cellular immune response induced by the vaccines, mice were sacrificed one week after boost and splenocytes were cultured with or without 5 µg/ml final concentration of rHepBag. Cytokines levels were measured by ELISA. The concept of low and high producers was applied to investigate a broader range of cytokines and assess ex vivo cytokine profiles of circulating leukocytes. For this purpose, the global median for each cytokine-positive cell subset was calculated, taking the whole range of values obtained for each group, as described elsewhere (Vitelli-Avelar et al., 2008, Scand J Immunol; 68(5):516-25). The global median percentage of each cytokine-positive cell population was used as the cut-off edge to segregate the individuals into two categories named 'low' and 'high'-cytokine producers, as shown in Table 1.

Figure 13:
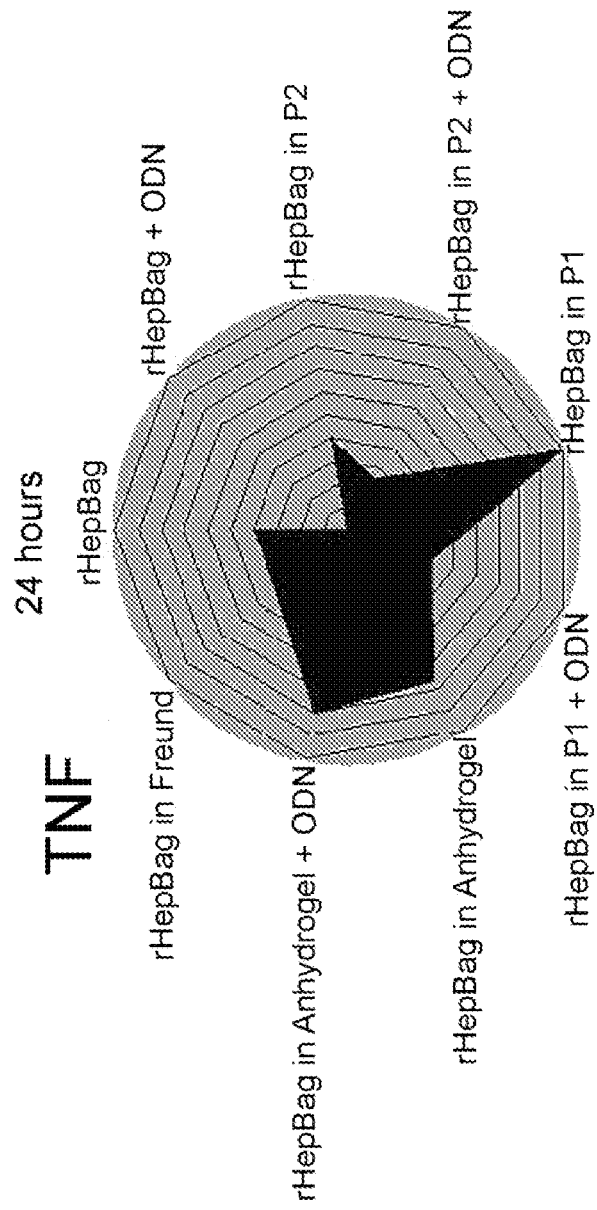
FIG. 13 is a radar graph representing the prevalence of ex vivo cytokine balance in a range of cell subsets from immunized mice (n=10/group) 24 hours post-primary inoculation. The values of the axis can be joined to form the central polygon area which represents the general cytokine balance. The analysis of the radar chart axes highlights the contribution of leukocyte for the overall cytokine balance.
Figure 14A:
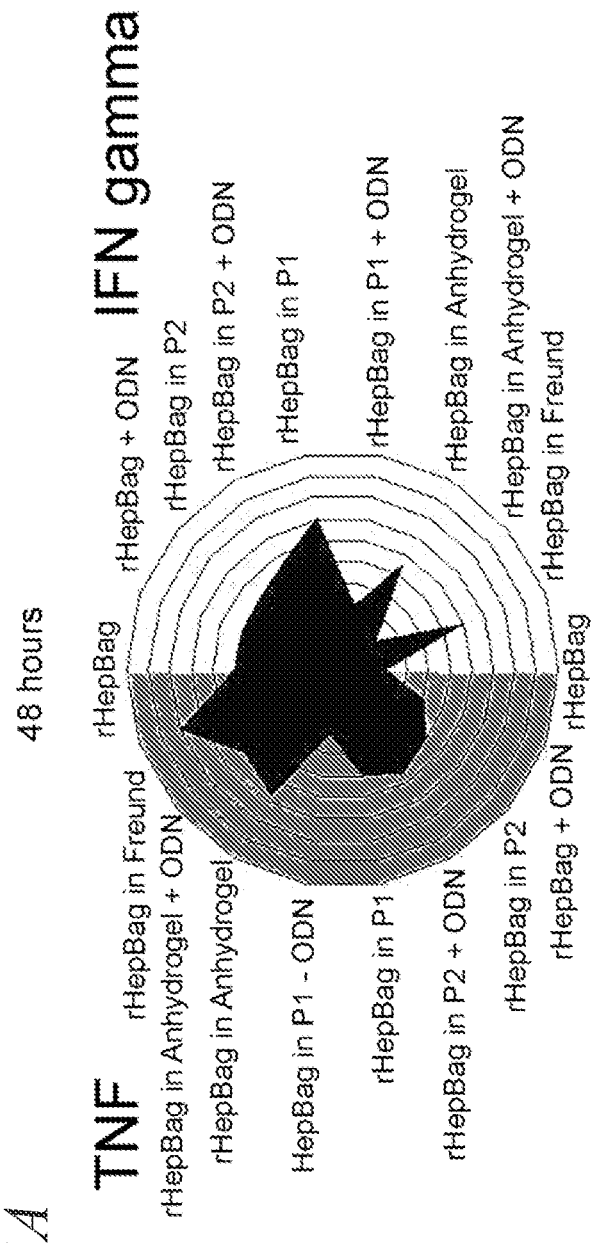
FIGS. 14A and 14B are radar graphs representing the prevalence of ex vivo cytokine balance in a range of cell subsets from immunized mice (n=10/group) 48 hours post-primary inoculation.
Figure 14B:
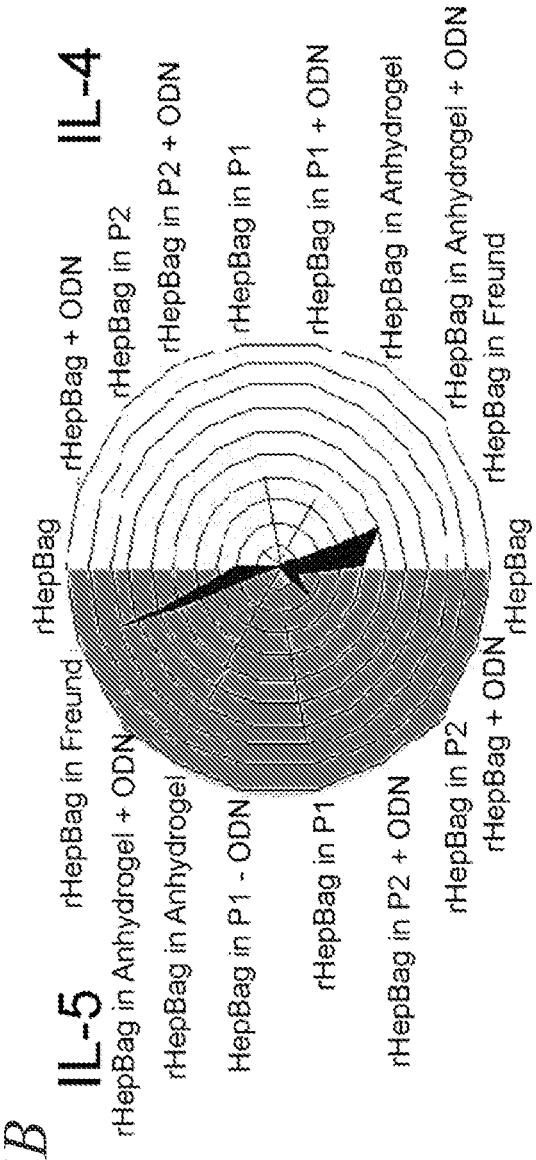

The data demonstrated that none of the mice inoculated with ODN 1826 showed TNF production in 24 hours, but when ODN 1826 was associated with adjuvants P1 or P2, a significant proportion of mice displayed values of TNF above the cut-off edge, as shown in FIG. 13 (P<0.011). Although ALHYDROGEL, when associated or not to ODN 1826, induced a significant amount of 'high'-TNF producers, all of the mice inoculated with adjuvant P1 without CpG displayed values above the cut-off, and this value was significantly higher than all Alhydrogel groups (P<0.001). This same result was not observed after 48 hours when adjuvants P1, P2, ALHYDROGEL and Freund showed a comparable number of 'high'-TNF producers (FIGS. 14A and 14B) (P<0.001).

Figure 15:
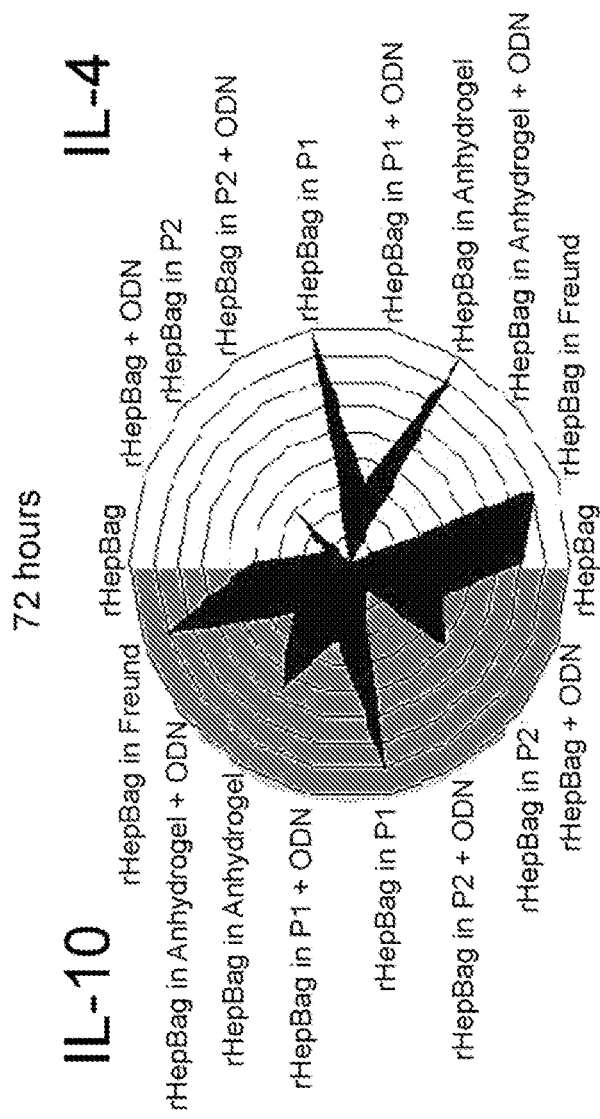
FIG. 15 is a radar graph representing the prevalence of ex vivo cytokine balance in a range of cell subsets from immunized mice (n=10/group) 72 hours post-primary inoculation. The values of the axis can be joined to form the central polygon area which represents the general cytokine balance. The analysis of the radar chart axes highlights the contribution of leukocyte for the overall cytokine balance.
Figure 16A:
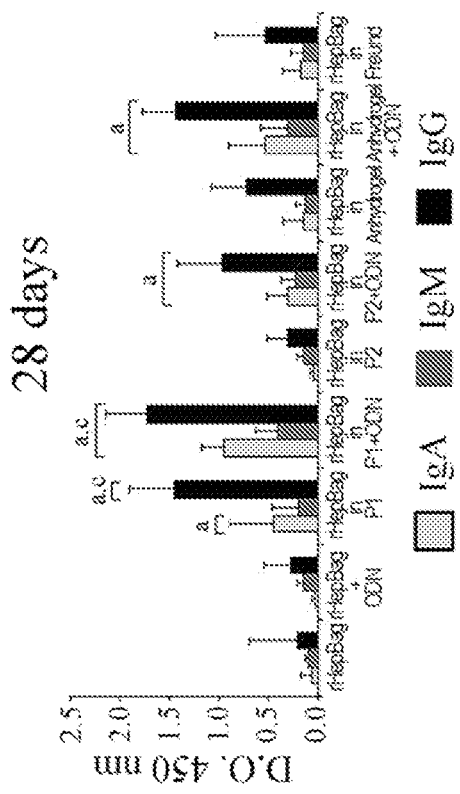
FIGS. 16A to 16D are comparisons of rHepBag-specific antibodies induced in immunized mice (n=10/group) between 14 and 35 days post-prime inoculation. The boost was performed 28 days after prime immunization and rHepBag-specific antibodies levels were determined by ELISA assay.
Figure 16B:
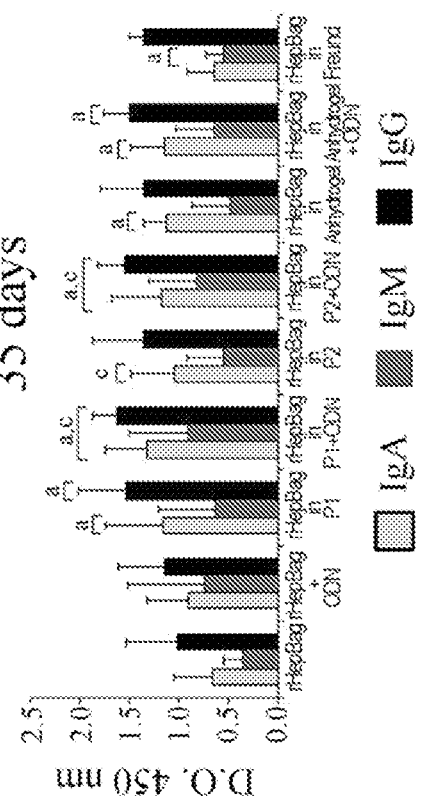
Figure 16C:
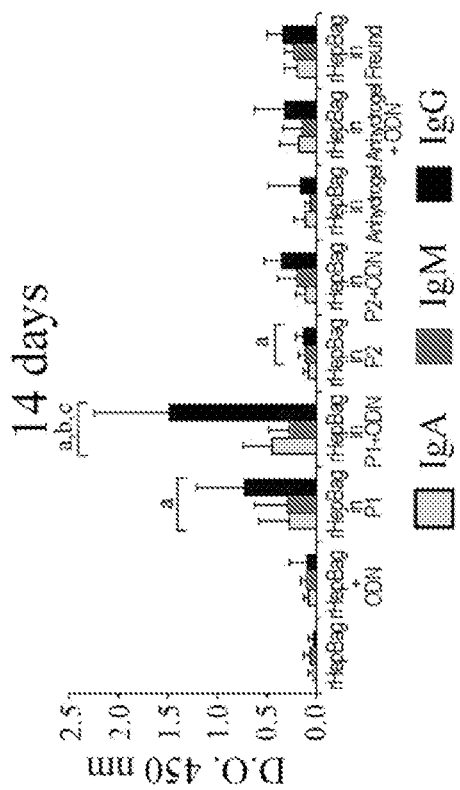
Figure 16D:
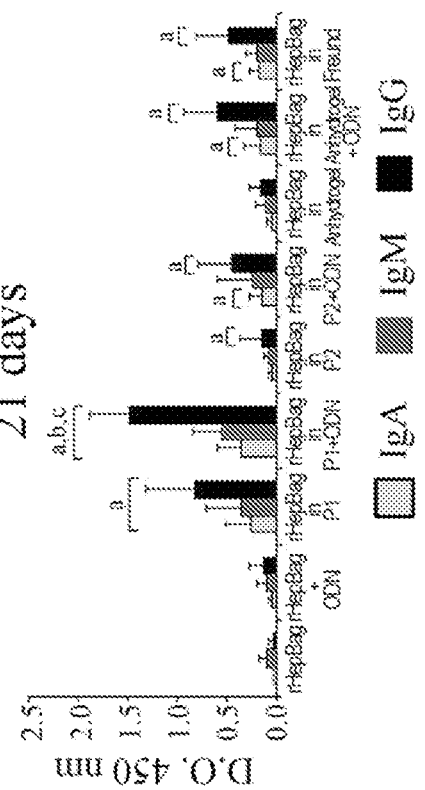
Figure 17A:
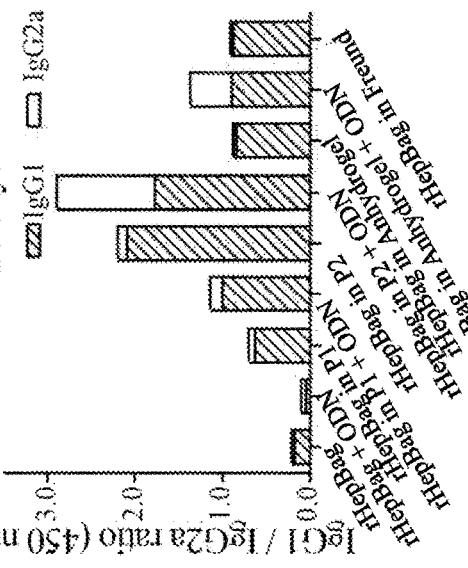
FIGS. 17A to 17D show IgG1:IgG2a ratio after immunization of mice (n=10/group) with rHepBag plus adjuvants between 14 and 35 days. The boost was performed 28 days after prime immunization and rHepBag-specific antibodies levels were determined by ELISA assay.
Figure 17B:
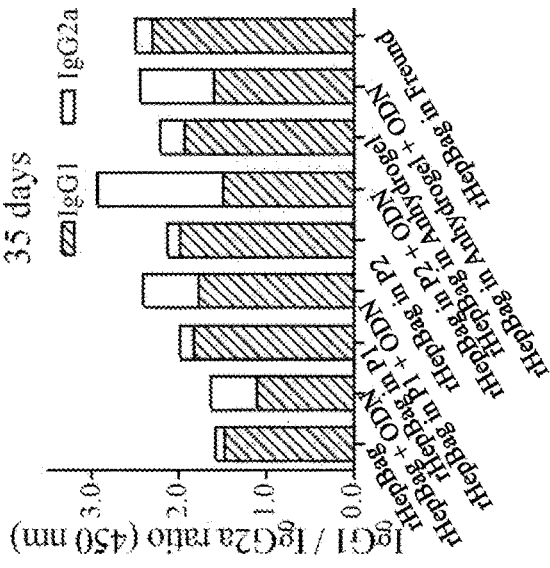
Figure 17C:
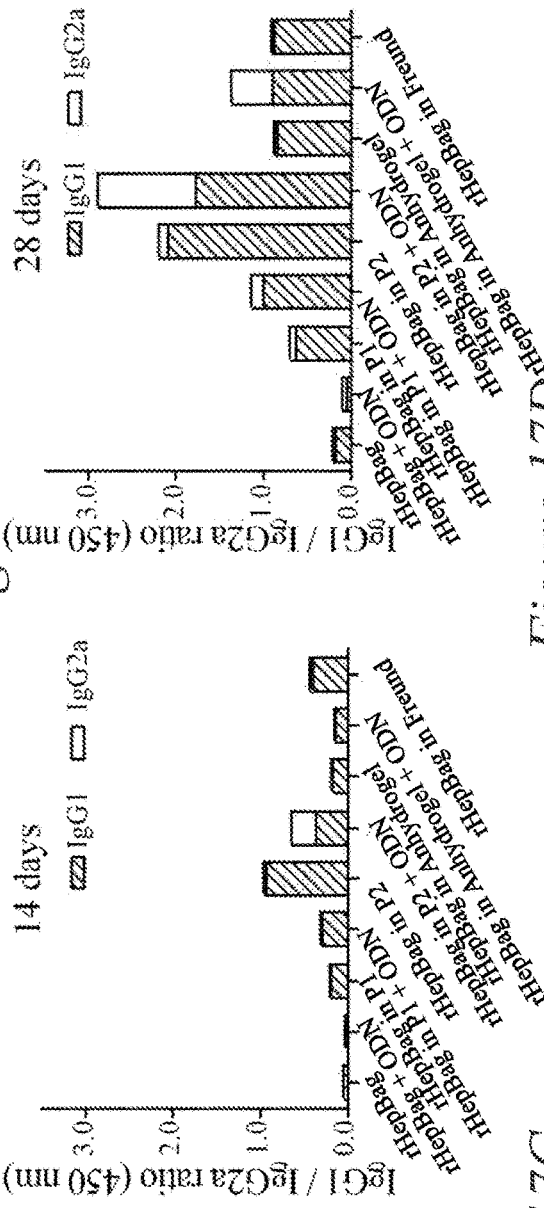
Figure 17D:
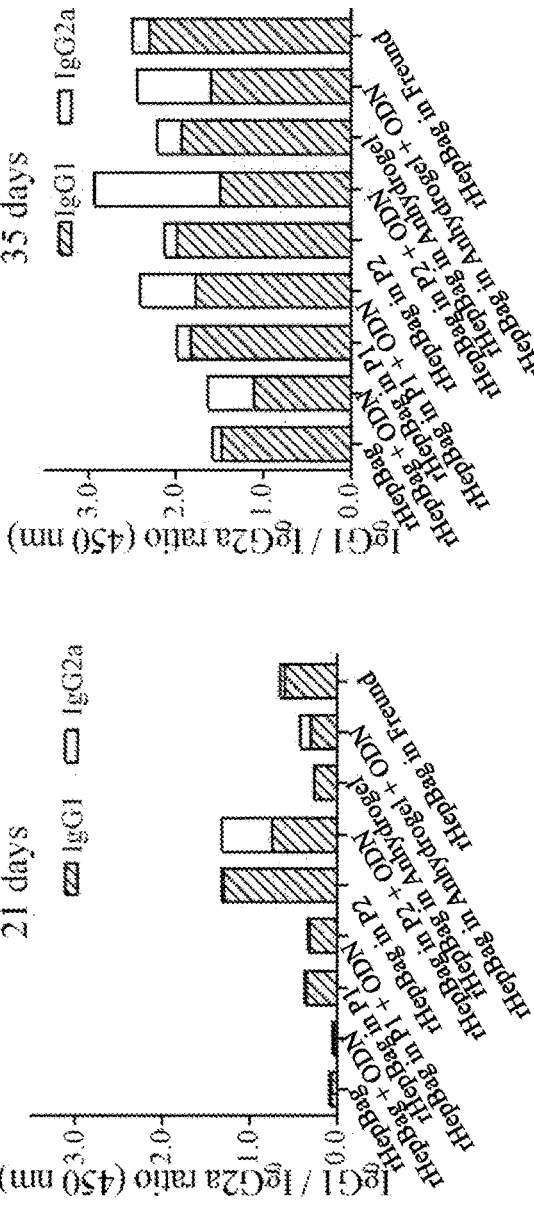

Moreover, interesting data was found for IL-4 and IL-5 production after 48 hours when most of the mice immunized with adjuvant P2 fell into a region of 'low'-IL-4 and IL-5 producers (P<0.05). Differently, most of the mice inoculated with adjuvant P1 presented a high production of both cytokines (P<0.002). As shown in FIG. 15, the adjuvant P1 continued to present 'high'-IL-4 producers after 72 hours, in association or not with ODN 1826 and this same result was found after ALHYDROGEL or Freund immunization (P<0.001). Also, the data demonstrated that most of the mice previously immunized with adjuvant P2 or adjuvant P2 plus ODN 1826 displayed values of IL-10 below the cut-off edge, significantly lower than mice immunized with rHepBag, associated or not to ODN 1826 (P<0.05).

Sustained humoral response in mice vaccinated with rHepBag and adjuvants P1 and P2. Sera were collected weekly before and after immunization to test specific isotypes antibody titer by ELISA. Mice vaccinated with both adjuvants P1 and P2 developed an anti-rHepBag IgG antibody in 2 weeks after prime inoculation (P<0.002). The highest anti-rHepBag antibody titers were reached in mice vaccinated with P1 associated or not to ODN, and these responses were significantly greater than immunization with ODN, Alum or Freund's adjuvants (P<0.001). The IgG1:IgG2a ratio elicited in vivo represents different patterns for both adjuvants. Adjuvant P1 drives to a Th2 response with high levels of IgG1 in 14 to 35 days post-prime inoculation.

Discussion

This example showed that mice vaccinated with either a P1 or P2 gel slurry plus ODN had significantly higher TNF production 24 to 48 hours after primary inoculation, while P1 was significantly superior to ALHYDROGEL at 24 hours. Adjuvant P2 presented a promising Th2 inhibition after 48 hours with the reduction of IL-4, IL-5 and IL-10 levels coincident with increased antigen-specific IgG2a production in serum.

The analysis of vaccine-specific antibodies showed that Pb drove high vaccine-specific IgA, IgM and IgG titers 14 days post-prime with or without using ODN and the high IgA and IgG titers was maintained for 35 days. As both of the gel slurry systems tested in this study were superior to the conventional adjuvants, this new gel slurry vaccine delivery system will have broad utility for enhancing responses to numerous current vaccines that are currently marginally functional. The use of this new vaccine delivery system will be further investigated in the development of vaccines for any kind of infectious diseases, from parasitic to viral infection.

TABLE 1

Frequency of cytokine high-producers subjects based on the global median cytokine cut-off detected in splenocytes culture stimulated with rHepBag*

| | | High cytokines producers (%) | | | | | | | |
|---|---|---|---|---|---|---|---|---|---|
| Cytokine | Global median cut off | rHepBag | rHepBag + ODN | rHepBag in P2 | rHepBag in P2 + ODN | rHepBag in P1 | rHepBag in P1 + ODN | rHepBag in Alhydrogel | rHepBag in Alhydrogel + ODN | rHepBag in Freund |
| 24 h | | | | | | | | | | |
| TNF | 0.009 (0.00-1.26) | 40 | 0 | 40 | 25$^b$ | 100$^{a,c,d}$ | 40$^b$ | 75$^a$ | 80$^b$ | 40 |
| 48 h | | | | | | | | | | |
| TNF | 12.96 (0.73-16.41) | 20 | 40 | 50$^a$ | 56$^b$ | 50$^a$ | 30 | 67$^a$ | 60$^b$ | 80$^a$ |
| IFN gamma | 0.00 (0.00-3.89) | 50 | 50 | 50 | 56 | 40 | 60 | 33 | 30 | 20 |
| IL-4 | 0.00 (0.00-0.00) | 20 | 0 | 10$^a$ | 0 | 40$^a$ | 0 | 33$^a$ | 0 | 50$^a$ |
| IL-5 | 0.00 (0.00-5.98) | 40 | 10 | 20$^a$ | 0 | 80$^a$ | 0 | 67$^a$ | 0 | 80$^a$ |
| 72 h | | | | | | | | | | |
| IL-4 | 0.00 (0.00-7.23) | 40 | 10 | 30 | 0 | 90$^{a,e}$ | 30$^b$ | 89$^a$ | 0 | 80$^a$ |
| IL-10 | 41.57 (0.00-179.00) | 70 | 40 | 50$^a$ | 11$^b$ | 80 | 30 | 56 | 30 | 80 |

*Data are expressed as percentage of mice displaying percentage of cytokine$^+$ cells higher or equal the global median cut-off calculated for each cell population within the adaptive immunity cells. Statistical significance at P ≤ 0.05 ($x^2$) are represented by superscript letters 'a', 'b', 'c', 'd' and 'e' for comparisons with rHepBag, rHepBag + ODN, rHepBag in Alhydrogel, rHepBag in Alhydrogel + ODN and rHepBag in Freund, respectively. PURAMATRIX (P1) and MATRIGEL (P2).

Whereas, the response elicited by P2 plus ODN is a mixed system rather than a pure Th1 or Th2 response, wherein the IgG1 and IgG2a levels were upregulated during all the timeline. See FIG. 17A-17D.

The combination of adjuvant P1+/−ODN induced the upregulation of IgA and IgM titers as soon as 14 days post-prime inoculation and this humoral response was maintained until 35 and 21 days, respectively (P<0.04). This adjuvant was superior to Freund's during 14 and 35 days and to ALHYDROGEL for the first 3 weeks for the production of IgA, IgM and IgG (P<0.02). Additionally, both adjuvants P1 and P2 demonstrated to be superior to Freund's adjuvant for the production of all Ig after boost (P<0.02). See FIGS. 16A-16D.

Example 2

Influenza Vaccination

Figure 18A:
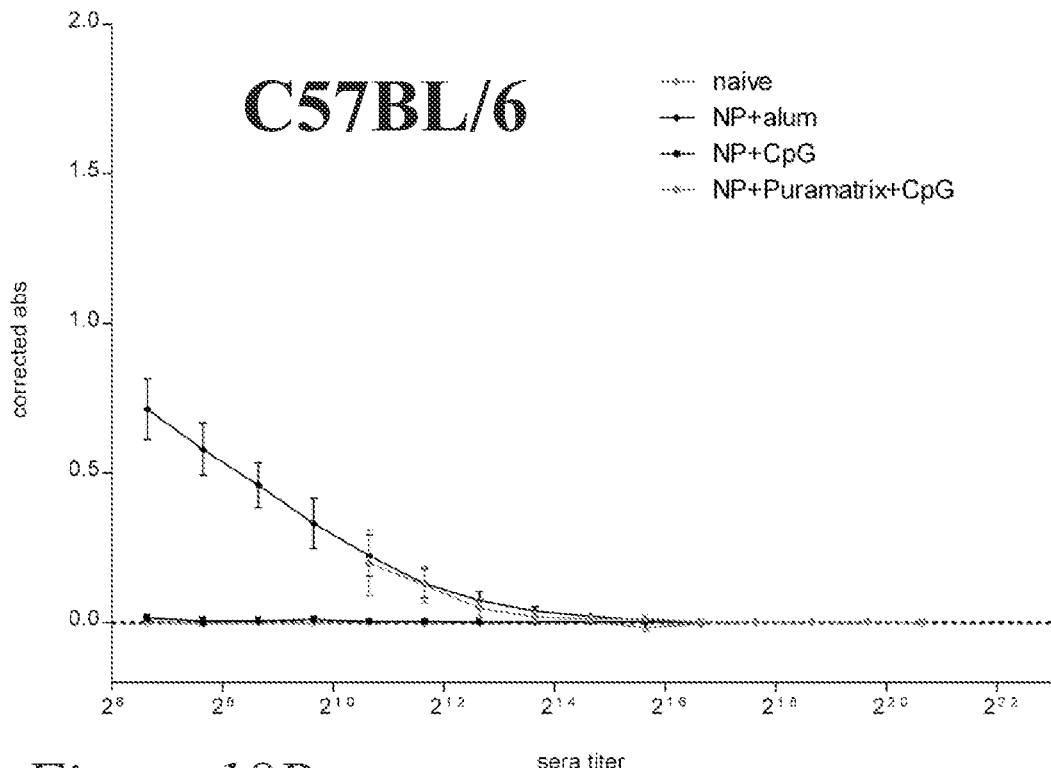
FIGS. 18A and 18B show increased anti-NP IgG titers in two strains of mice vaccinated with rNP.
Figure 18B:
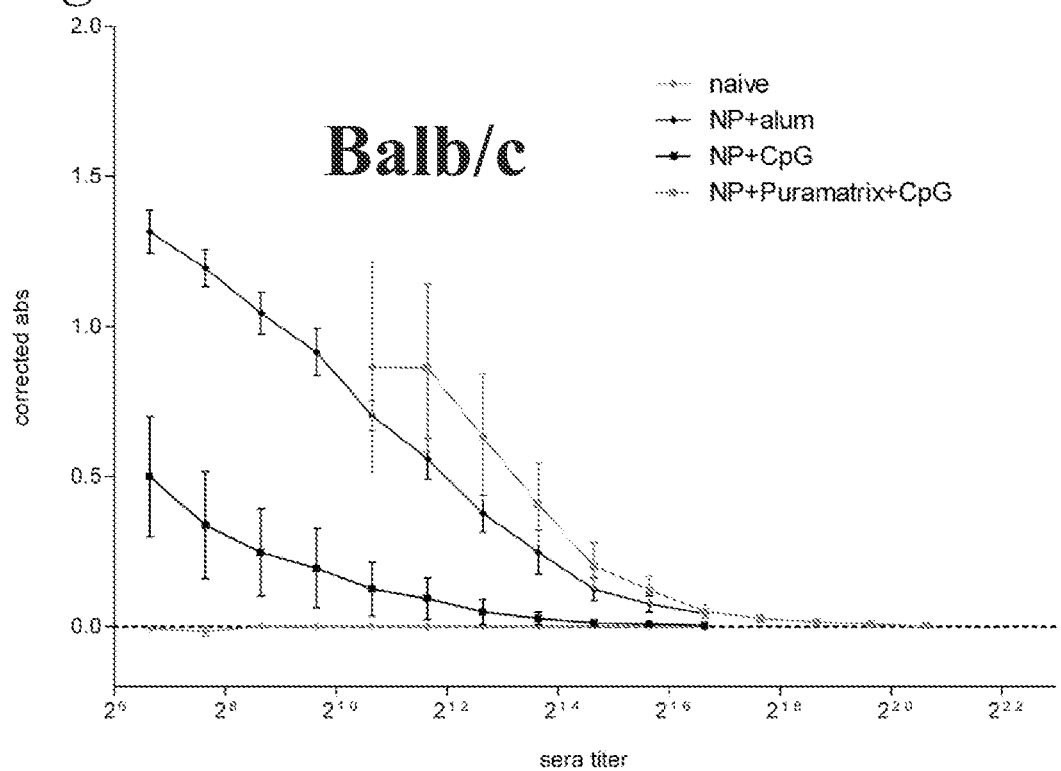

Following methods described in more detail in the previous examples, C57/BL and Balb/c mice were immunized with the recombinant nucleoprotein (rNP) influenza virus antigen administered with alum, CpG, or a slurry of PURAMATRIX and CpG. To prepare one dose of the slurry, 10 ug rNP antigen, with or without prior mixing with 50 ug CpG, was brought to a final volume of 200 ul with PURAMATRIX and mixed thoroughly before subcutaneous injection. Amounts were scaled up depending on the number of doses needed. As shown in FIG. 18B, anti-influenza IgG titers were increased Balb/c mice vaccinated with rNP administered as a slurry with PURAMATRIX and CpG, as compared to mice vaccinated with rNP administered with the adjuvant alum or CpG. FIG. 18A shows anti-influenza IgG titers in C57BL/6 mice. Anti-influenza IgG titers were determined four weeks post-last vaccination (wplv).

Again, following methods described in more detail in the previous examples, C57B$^1$/$_6$ mice were immunized with whole inactivated influenza A virus (H1N1) strain PR8 administered with alum, as a PURAMATRIX slurry, or as a slurry of PURAMATRIX and CpG. As a control, additional mice were immunized with PR8 whole inactivated virus (WIV) only. To prepare one dose of the slurry, 15 ug of PR8 antigen, with or without prior mixing with 50 ug CpG, was brought to a final volume of 200 ul with PURAMATRIX and mixed thoroughly before subcutaneous injection. Amounts were scaled up depending on the number of doses needed. PR8 (WIV) is formalin-inactivated influenza A/PR/8/34 (H1N1) from Charles River rNP is recombinant human Influenza A (A/PR/8/34/Mount Sinai (H1N1) segment 5) nuclear protein NP from Imgenex.

Figure 19A:
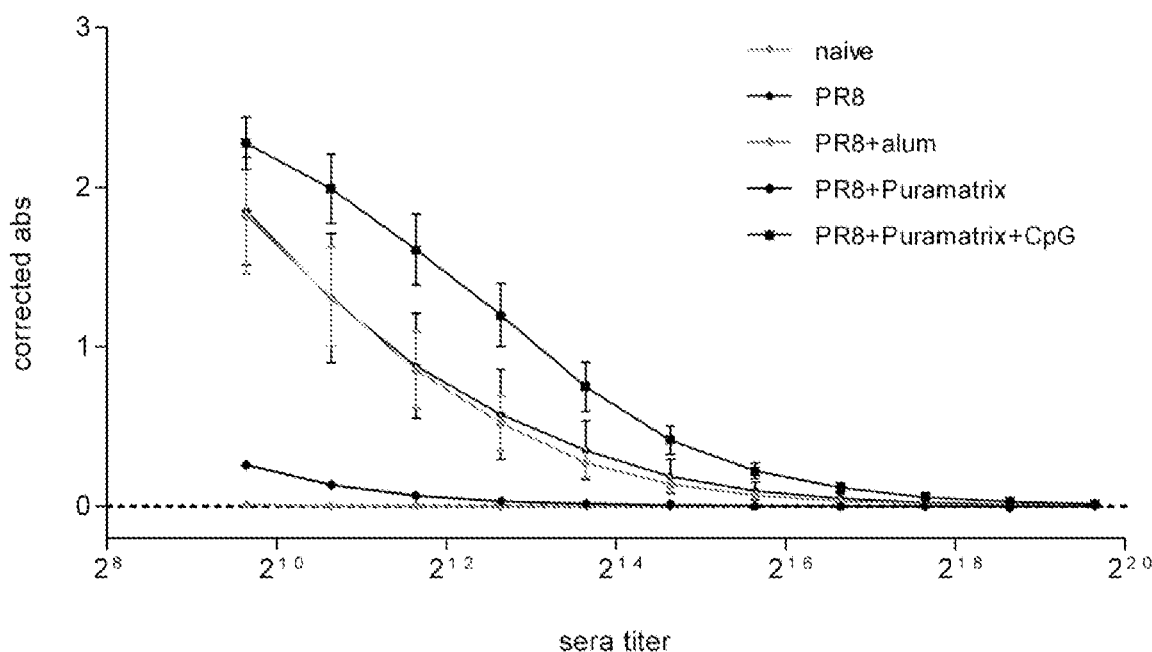
FIGS. 19A and 19B show increased anti-influenza IgG titers in in C57Bl/6 mice vaccinated with PR8 WIV.
Figure 19B:
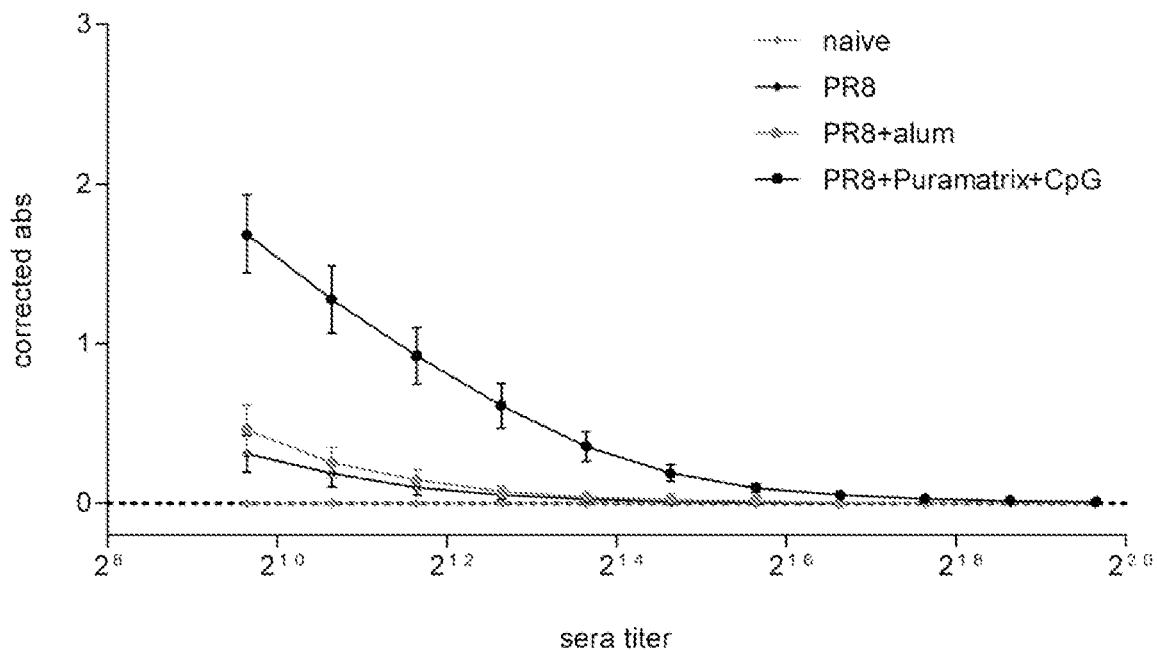

As shown in FIG. 19, serum anti-influenza IgG titers were increased in C57Bl/6 mice vaccinated with PR8 WIV administered as a slurry of PURAMATRIX and CpG, as compared to mice vaccinated with PR8 WIV administered with the adjuvant alum or as a slurry with PURAMATRIX alone, without CpG. Anti-influenza IgG titers were determined four weeks post-last vaccination (wplv). FIG. 19 shows results from two independent experiments.

Figure 20A:
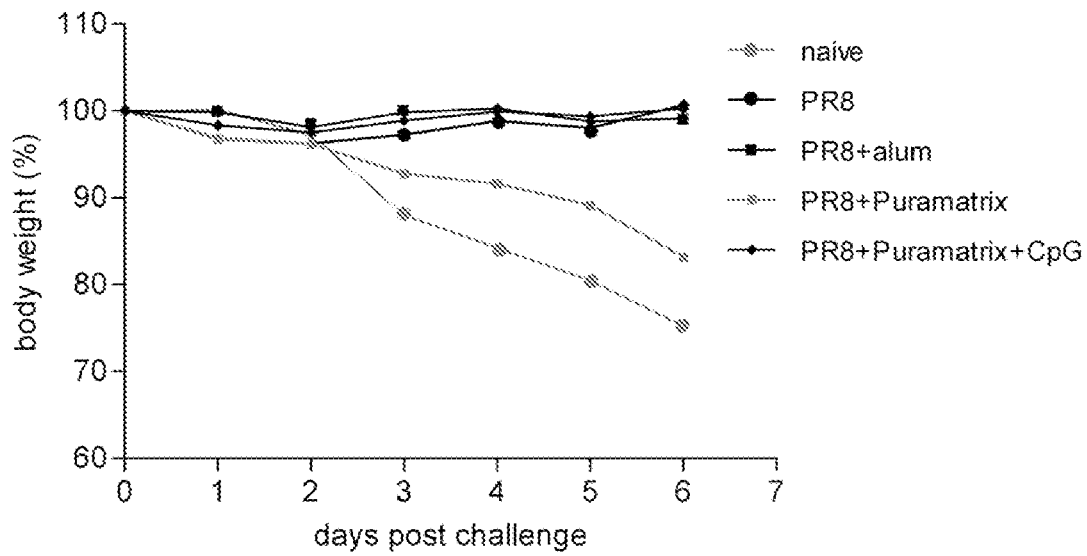
FIGS. 20A and 20B show increased protection from lethal challenge in C57Bl/6 mice vaccinated with PR8 WIV.
Figure 20B:
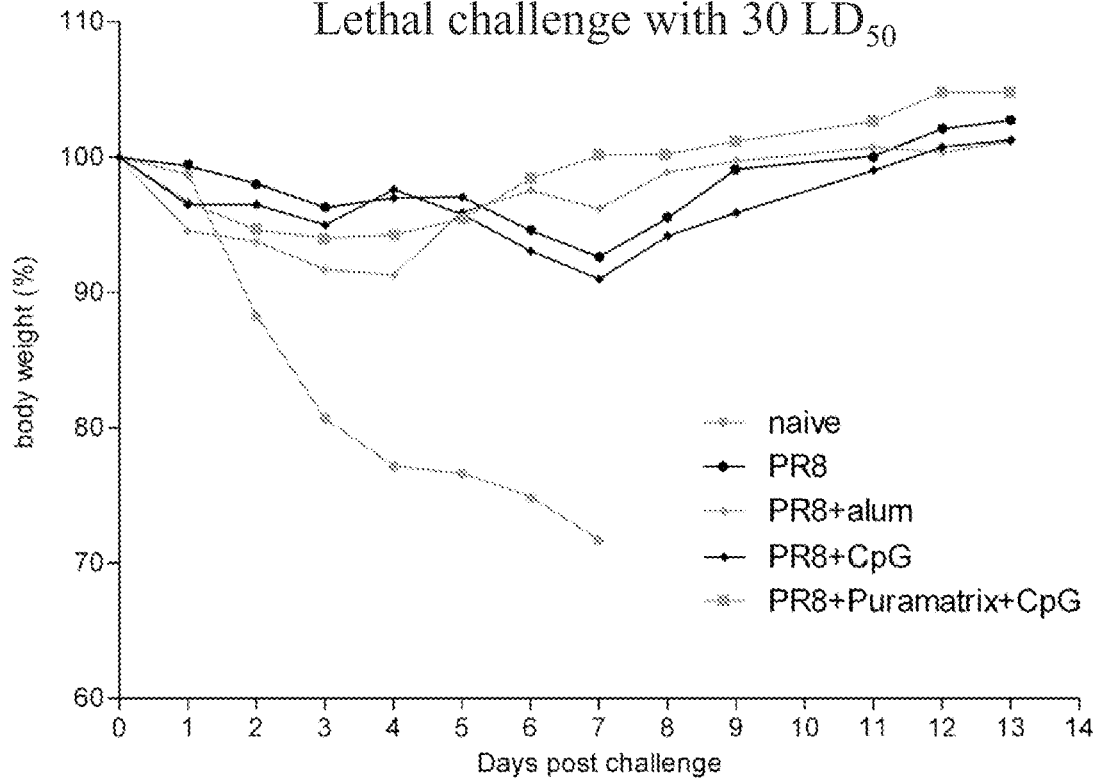
Figure 22A:
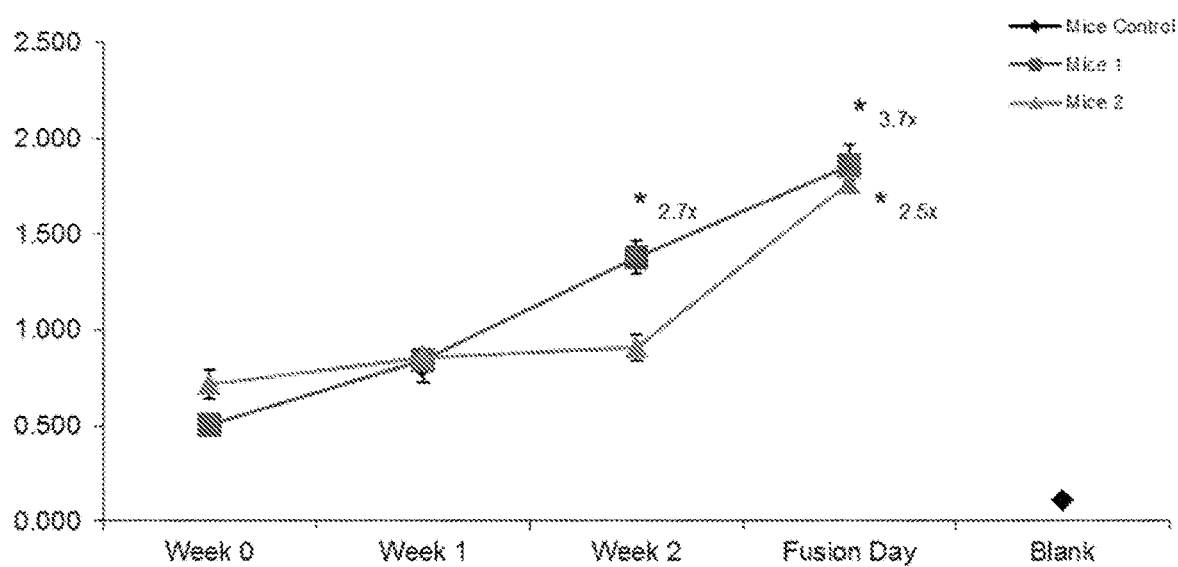
FIGS. 22A and 22B show IgG anti-schistosome CCA protein antibody titers in mice immunized with CCA in complete Freund's adjuvant (FIG. 22A) and CCA in MATRIGEL plus CpG (FIG. 22B).
Figure 22B:
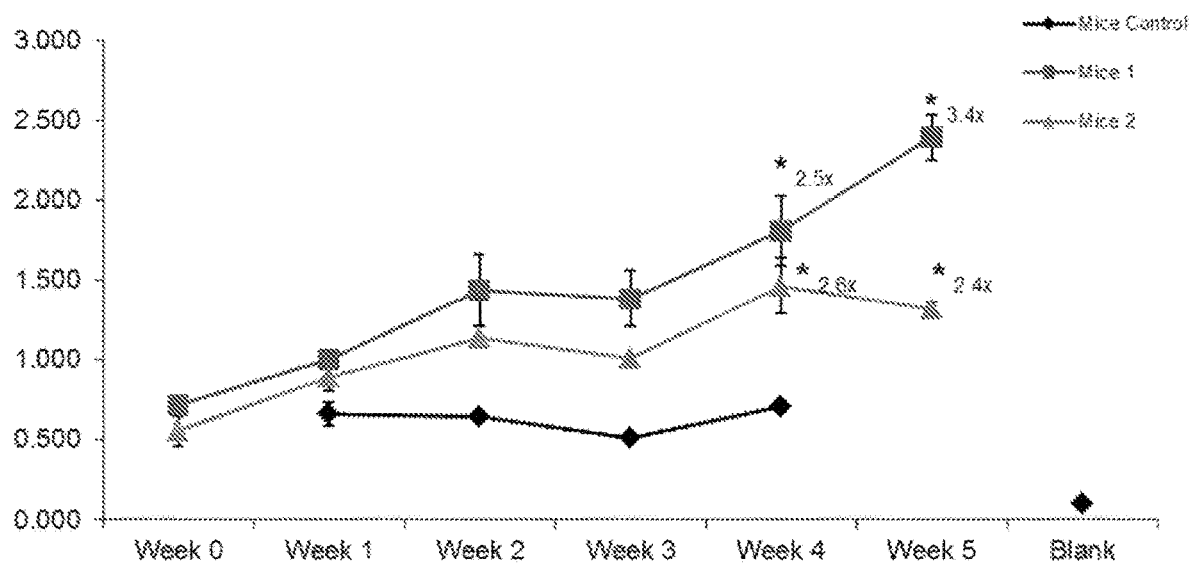

As show in FIG. 20, enhanced protection from lethal challenge was observed in C57Bl/6 mice vaccinated with PR8 WIV. FIG. 20A shows results from an independent experiment with lethal challenge at 30 LD$_{50}$ and FIG. 20B shows results from an independent experiment with lethal challenge at 1000 LD$_{50}$.

Example 3

Burkholderia Vaccination

Following methods described in more detail in the previous example, mice were immunized with a cocktail of three different burkholderia recombinant proteins (burkholderia 4-9 protein, the burkholderia 22-11 protein, and the burkholderia 42 protein) administered with one of three different adjuvants preparation, alum, Complete Freund's Adjuvant (CFA), or slurry of PURAMATRIX and CpG. To prepare one dose of the PURAMATRIX+CpG slurry, 75 ug of Burkholderia proteins antigen, with or without prior mixing with 50 ug CpG, was brought to a final volume of 200 ul PURAMATRIX and mixed thoroughly before subcutaneous injection. Amounts were scaled up depending on the number of doses needed. As controls, additional mice were immunized with alum only, CFA only, or PURAMATRIX+CpG slurry, without antigen.

The *Burkholderia* (previously part of *Pseudomonas*) genus name refers to a group of virtually ubiquitous gram-negative, motile, obligatory aerobic rod-shaped bacteria including both animal/human and plant pathogens as well as some environmentally important species. Burkholderia is best known for its pathogenic members. *Burkholderia mallei* is responsible for glanders, a disease that occurs mostly in horses and related animals. *Burkholderia pseudomallei* is the causative agent of melioidosis (also called Whitmore's disease), an infectious disease predominately of tropical climates that can infect humans or animals, especially in Southeast Asia and northern Australia. *Burkholderia cepacia* is an important pathogen of pulmonary infections in people with cystic fibrosis. Due to their antibiotic resistance and the high mortality rate from their associated diseases *Burkholderia mallei* and *Burkholderia pseudomallei* are considered to be potential biological warfare agents, targeting livestock and humans.

FIG. 21 shows anti-burkholderia IgG titers in mice immunized with a cocktail of three burkholderia recombinant proteins (burkholderia 4-9 protein, the burkholderia 22-11 protein, and the burkholderia 42 protein). FIG. 21B shows anti-burkholderia protein 4-9 IgG titers in immunized mice. FIG. 21A shows anti-burkholderia protein 22-11 IgG titers in immunized mice. FIG. 21C shows anti-burkholderia protein 42 IgG titers in immunized mice. Antibody titers after immunization with alum only, alum+protein cocktail, complete Freund's adjuvant (CFA) only, CFA+protein cocktail, PURAMATRIX+CpG slurry only, and PURAMATRIX gel+protein cocktail are shown. An increased immune response as measured by specific serum antibody levels were observed against two of the three proteins administered as a gel vaccine composition with puramatrix compared with vaccination with alum or CFA. Specifically, increased anti-burkholderia IgG titers were observed against the burkholderia 4-9 protein (FIG. 21B) and the burkholderia 22-11 protein (FIG. 21AB) when administered as a gel vaccine with PURAMATRIX, compared with vaccination with alum or CFA. Challenge data is being analyzed.

Example 4

Veterinary Vaccines

Following procedures described in more detail in the previous examples, the present invention may be used with any of a variety of veterinary vaccines. The vaccine compositions, delivery methods, and delivery system of the present invention will provide many advantages and better value for the commercial livestock industry, including, but not limited to, improved efficacy, delivery early in the production cycle, and efficacy with the administration of only a single dose to provide protection throughout the production cycle.

The compositions, delivery methods, and delivery systems of the present invention may be used in the immunization of swine. Vaccines that may be administered to swine using the compositions, methods and systems of the present invention include, but are not limited to, porcine circovirus type 2 (PCV2) vaccine, porcine reproductive and respiratory syndrome (PRRSV), respiratory mycoplasma vaccine, *Streptococcus suis* vaccine, porcine coronavirus vaccine, rotavirus vaccine, enterotoxigenic *Escherichia coli* (K88) vaccine, *Actinobacillus pleuropneumonia* (APP) vaccine, and swine influenza vaccine. See, for example, the world wide web at merck-animal-health.com/species/pigs/vaccines.aspx, "Vaccinations for the Swine Herd," Alabama Cooperative Extension System Publication ANR-902, Alabama A&M and Auburn Universities (available on the world wide web at aces.edu/pubs/docs/A/ANR-0902/ANR-0902.pdf), and "Pig vaccination programs," PRIME FACT publication 944, September 2009 (available on the world wide web at dpi.nsw.gov.au/_data/assets/pdf file/0009/301500/Pig-vaccination-programs.pdf) for more detailed information on available vaccines and the administration of such vaccines to swine.

The compositions, delivery methods, and delivery systems of the present invention may be used in the immunization of bovine, including, but not limited to, domestic cattle, water buffalo, African buffalo, bison, and yaks. Vaccines that may be administered to bovines, using the compositions, methods and systems of the present invention include, but are not limited to, bovine respiratory disease (BRD) vaccine, including, but not limited to BVDV types I and II, bovine herpes virus 1 (BHV-1) vaccine, including, but not limited to, subunit vaccines that would not result in latent virus, *Haemophilus somnus* vaccine, *Mannheimia haemolytica* vaccine, *Mycoplasma bovis* vaccine, bovine rotavirus vaccine, *Escherichia coli* K99 vaccine, bovine coronavirus (BCV) vaccine, *Clostridium chauvoei* (black leg) vaccine, *Clostridium septicum* vaccine, *Clostridium sordelli* (malignant edema) vaccine, *Clostridium novyi* (black disease) vaccine, *Clostridium perfringens* (enterotoxemia) vaccine, infectious bovine keratoconjunctivitis (pink eye) vaccine, including, but not limited to, *Moraxella bovis*, chlamydia, mycoplasma, acholeplasma, or infectious bovine rhinotracheitis (IBR) virus vaccines, mastitis vaccines, including, but not limited to, *Escherichia coli* J5 vaccine.

In some applications, the compositions, delivery methods, and delivery systems of the present invention may be used for the administration of one or more schistosomiasis antigens to a bovoid. Such a schistosome antigen may be derived from, for example, *Schistosoma japonicum*, *Schistosoma monsoni*, or *Schistosoma haematobium*. A schistosome antigen may be a schistosome triose phosphate isomerase (CTPI) protein, or antigenic fragment or derivative thereof, including, but not limited to a *S. japonicum*, *S. monsoni*, or *S. haematobium* CTPI protein, or antigenic fragment or derivative thereof. A schistosome antigen may be a schistosome tetraspin 23 kDa integral membrane protein (C23), or antigenic fragment or derivative thereof, including, but not limited to a *S. japonicum*, *S. monsoni*, or *S. haematobium* C23 protein, or antigenic fragment or derivative thereof. Such a schistosome antigen may be a chimeric polypeptide, fused to one or more additional antigenic determinants, such as for example, a heat shock protein, or antigenic fragment or derivative thereof, including, but not limited to, bovine heat shock protein 70 (Hsp70).

See, for example, "Beef Cattle Herd Health Vaccination Schedule" Powell et al., University of Arkansas, Division of Agriculture, Agriculture and Natural Resources publication FSA3009 (available on the world wide web at uaex.edu/Other Areas/publications/PDF/FSA-3009.pdf), "How to Vaccinate," Oklahoma Cooperative Extension Service, Division of Agricultural Sciences and Natural Resources, Publication No. 350 (available on the world wide web at ansci.colostate.edu/pdf_files/YLE/Dairy7_vaccinate.pdf), and "Cattle Vaccines and Their Use," Beef Cattle Handbook publication BCH-3015 (available on the world wide web at iowabeefcenter.org/Beef%20Cattle%20Handbook/Vaccines_Cattle.pdf) for more detailed information on available vaccines and the administration of such vaccines to cattle.

The vaccine compositions, delivery methods, and delivery system of the present invention may also be used in the vaccination of companion animals, including, but not limited to cats and dogs, such as, for example, for the immunization of dogs with parvovirus vaccine for transfer of maternal immunity.

Routes of administration include, but are not limited to, subcutaneous (sc) or intramuscular (im) injection. Vaccination with the composition, methods, and delivery systems of the present invention will yield rapid, longer lasting protection after administration of a single dose.

Example 5

Poultry Vaccines

Following procedures described in more detail in the previous examples, the present invention may be used as a delivery system for any of a variety of poultry vaccines, including, but not limited to, vaccines for infectious bronchitis (TB), Newcastle disease (ND), Marek's diseases, infectious bursal disease (IBD) virus, infectious laryngotracheitis (ILT), avian reovirus, cholera, fowl pox, mycoplasmosis, turkey and chicken Coryza, avian influenza, avian encephalomyelitis (AE), avian rhinotracheitis (ART), duck virus hepatitis, haemorrhagic enteritis, goose parvovirus, Paramyxovirus 3, chicken anaemia virus (CAV), *E. coli*, Erysipelas, *Reimerella, Mycoplasma gallisepticum, Pasteurella multocida, Salmonella enteritidis, Salmonella typhimurium*, and coccidiosis.

Routes of administration include, but are not limited to, subcutaneous (sc) or intramuscular (im) injection. With subcutaneous injection, vaccine is injected into the space between the skin and underlying tissues. Typically the site of application used in poultry in the loose skin at the back of the neck. With intramuscular injection, the vaccine preparation is deposited within a mass of muscle. Typically, either the breast muscle or the thigh muscle is used for this purpose. Vaccination may include the vaccination of day old hatchlings, pullets, layers, breeders, broilers, and/or show birds. Typically layers and breeders get vaccinated prior to the laying period, and then every 6 to 8 weeks with inactivated vaccines during the laying period. This not only protects them from disease but passes on maternal antibodies to the progeny. Poultry that may be vaccinated include, but are not limited to, chickens, turkeys, and waterfowl, such as, for example, ducks and geese.

Example 6

Schistosomiasis Immunization

Mice were immunized with the schistosome protein antigen CCA in either complete Freund's adjuvant or in MATRIGEL plus CpGs. Anti-CCA IgG antibody titers were determined by ELISA The data is shown in FIG. 22A (CCA in complete Freund's adjuvant) and FIG. 22B (CCA in MATRIGEL plus CpGs). Two mice were immunized for each antigen preparation. Sera samples were collected at 0, 8, 16, and 19 days post immunization for mice immunized with CCA in complete Freund's adjuvant and at 0, 8, 16, 24, 32, and 40 days post immunization for mice immunized with CCA in MATRIGEL plus CpGs. The ELISA data clearly shows higher titers of CCA specific antibodies in mice immunized with MATRIGEL plus CpGs.

Example 7

Schistosomiasis Vaccination of Water Buffalo

Schistosomiasis is a parasitic disease affecting more than 200 million people worldwide. Reassessment of schistosomiasis-related disability, combined with recent information on the global prevalence of schistosome infection indicates that the true burden of schistosomiasis is substantially greater than previously appreciated. In Asia, particularly China, the causative agent is *Schistosoma japonicum*. Unlike the African species, *S. mansoni* and *S. haematobium, S. japonicum* is a zoonotic parasite, with bovines, particularly water buffaloes accounting for about 75% of schistosome transmission to humans in China. Interventions that reduce schistosome infection in water buffaloes will enhance their health simultaneously reducing disease transmission to humans. Current control programs in many areas of China include simultaneous praziquantel (PZQ) treatment of humans and water buffaloes; while this has shown a reduction in the overall prevalence, it requires continued mass treatments that are both time consuming and expensive. A more sustainable option would be development of a vaccine which reduces transmission of S. japonicum from bovines to replace bovine chemotherapy. Indeed mathematical modeling (Williams et al., 2002, Acta Trop; 82(2):253-262) has demonstrated that reducing S. japonicum infection in bovine reservoirs using prophylactic vaccines with 45% efficacy alone or in combination with PZQ should over time reduce the equilibrium prevalence and potentially lead to long-term sustainable control of schistosomiasis. This two-pronged base intervention would significantly reduce transmission of schistosomiasis for the long term, increase bovine health and growth and would likely reduce overall morbidity in village populations. See Da'Dara et al., 2008, Vaccine; 26(29-30): 3617-3625, which is herein incorporated by reference in its entirety.

Antigen-PURAMATRIX compositions as described herein will be used to immunize livestock with S. japonicum antigens. For these trials, all animals will be given a primary vaccination with a SjCTPI-Hsp70 plasmid DNA vaccine (as described in more detail in Da'Dara et al., 2008, Vaccine; 26(29-30):3617-3625). Water buffalo will be boosted with a composition of recombinant SjCTPI protein, PURAMATRIX and bovine CpG. Specifically, 100 ug of recombinant SjCTPI plus bovine CpG will be mixed in PURAMATRIX for a total injection volume of approximately 0.50 ml/animal. This will be injected into the shoulder of buffalo/and cattle. Only a single booster vaccination will be administered to an animal.

The elicitation of a humoral and cellular immune responses, including anti-SjCTPI IgG antibody response, will be determined. After boosting, animals will be challenged were challenged with cercariae and vaccine efficacy determined by measuring the reduction in the number of eggs per gram feces, reduction in eggs in liver tissues, reduction in miracidial hatching, and reduction in worm burden. Methods for these determinations are described in more detail in Da'Dara et al., 2008, Vaccine; 26(29-30): 3617-3625.

A first trial in the Philippines is already in Year 2 in the Philippines, with 400 water buffalo or cattle having been boosted, as described above. A second trial in Samar, Philippines, will include 1500 water buffalo or cattle. A third trail in China will include 600 water buffalo or cattle.

Immunization of water buffalo and cattle with compositions of schistosome polypeptides, such as for example, SjCTPI, SjCTPI-Hsp70, SjC23, or SjC23-Hsp70 polypeptides, in a puramatrix composition, with or without adjuvants, such as for example, CpG or IL-12, may serve as the basis for new control programs for schistosomiasis in Asia. Such a program, in addition to treatment with praziquantel (PZQ), would include vaccination of water buffaloes with partially protective vaccines such SjC23-Hsp70 and SjCTPI-Hsp70 as a means to reduce numbers of egg-laying parasites in livestock, leading to measurable declines in prevalence, intensity and transmission of S. japonicum.

Example 8

Figure 23A:
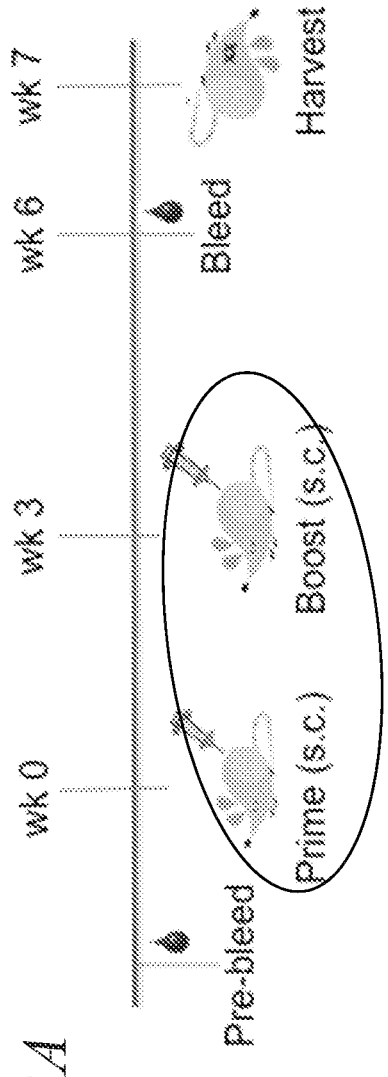
FIGS. 23A to 23C show increased anti-NP influenza antibody titers using standard vaccination methodologies.

New Vaccination Delivery System Provides Increased Influenza-Specific Antibody Response After Primary Immunization and Boost The preparation of vaccine compositions is described in more detail in the previous examples. BALB/C mice and C57BL/6 mice were immunized by sub-cutaneous injection with recombinant nucleoprotein (rNP) influenza virus antigen administered with alum, CpG, or a slurry of PURAMATRIX ("X") and CpG. As a control, additional mice were given a naïve (mock) injection. A schematic of the method is shown in FIG. 23A. A blood sample from mice was collected the day prior to immunization. A sub-cutaneous boost was given at week 3, another blood sample from mice was collected at 6 weeks, and mice were harvested at week 7.

Figure 23C:
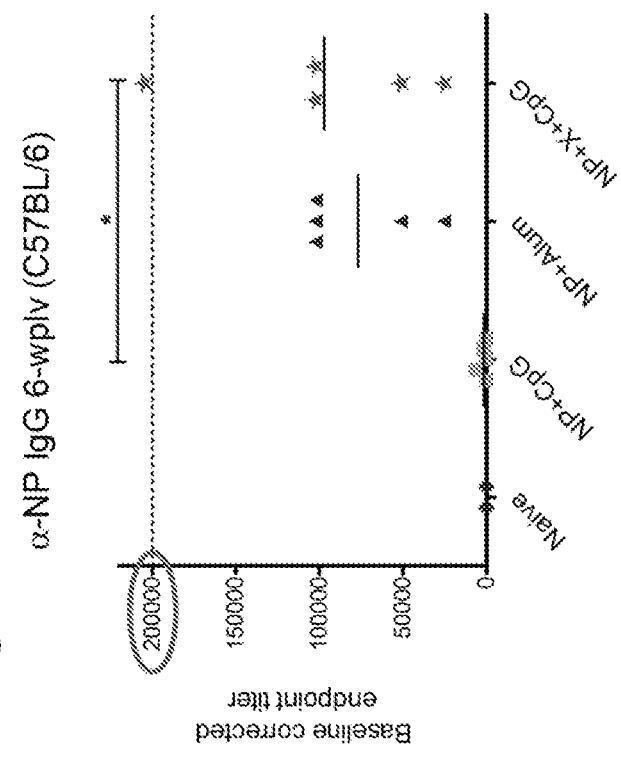
Figure 23B:
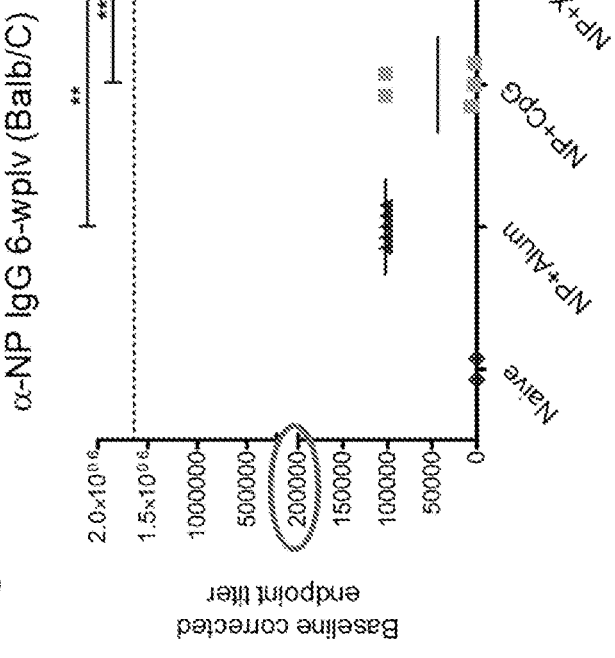

As shown in FIG. 23, serum anti-influenza IgG titers were increased in BALB/C mice (FIG. 23B) vaccinated with a-NP administered with as a slurry of PURAMATRIX and CpG, as compared to mice vaccinated with a-NP administered with the adjuvant alum or as a slurry with PURAMATRIX alone, without CpG. Similarly, anti-influenza IgG titers were slightly increased in C57BL/6 mice (FIG. 23C) vaccinated with a-NP administered with as a slurry of PURAMATRIX and CpG, as compared to mice vaccinated with a-NP administered with the adjuvant alum and were significantly increased as compared to mice vaccination with a slurry with PURAMATRIX alone, without CpG. Anti-influenza IgG titers were determined six weeks post-vaccination (wpv).

An increased humoral response was observed in C57BL/6 mice vaccinated with rNP via the new delivery method and further studies with the Influenza model were pursued as described in the following examples.

Example 9

New Vaccination Delivery System Provides Increased Influenza-Specific Antibody Response and Increased Protection from Challenge After Single Immunization The preparation of vaccine compositions is described in more detail in the previous examples. In an effort to mimic the seasonal vaccine received by the high-risk groups, a single vaccination of inactivated virus was used. A whole-inactivated influenza A virus (WIV) strain Puerto Rico/08/34 (PR8) is considered the most immunogenic and was used in this study. The humoral response to the vaccine is often considered the most important element for protection and is therefore the focus of this study.

Figure 24A:
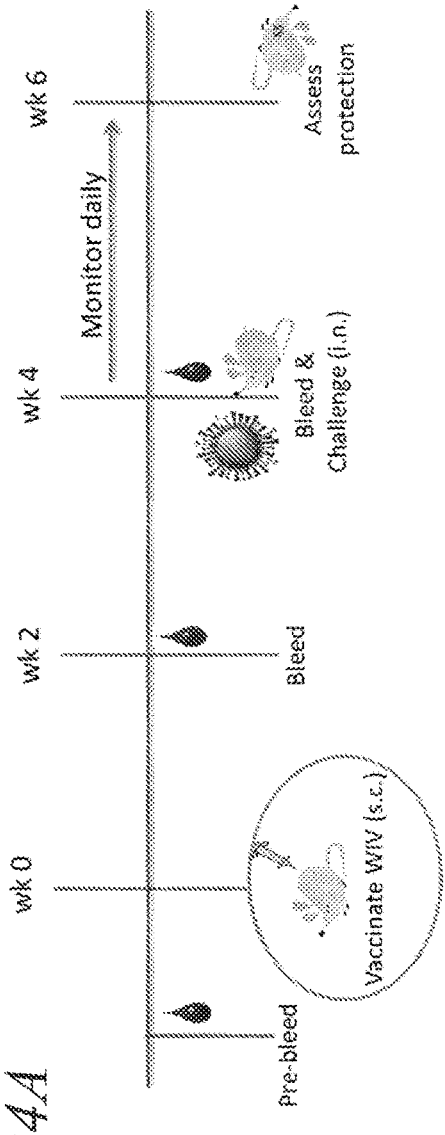
FIGS. 24A to 24C show greatly increased anti-PR8 influenza antibody titers after single vaccination.

C57BL/6 mice were immunized with PR8 WIV administered with alum, with CpG, as a PURAMATRIX slurry, or as a slurry of PURAMATRIX and CpG. As controls, additional mice were immunized with PR8 whole inactivated virus (WIV) only or were given a naïve (mock) injection. A schematic of the method is shown in FIG. 24A. Blood samples from mice were collected the day prior to immunization and at weeks 2 and 4. A lethal influenza challenge of live homologous PR8 at 1,000 $LD_{50}$ was given by intra-nasal (i.n.) administration at week 4, and mice were harvested at week 6. Mice were monitored daily from challenge until harvest and were analyzed for both specific antibody titers and morbidity and mortality results.

Figure 24C:
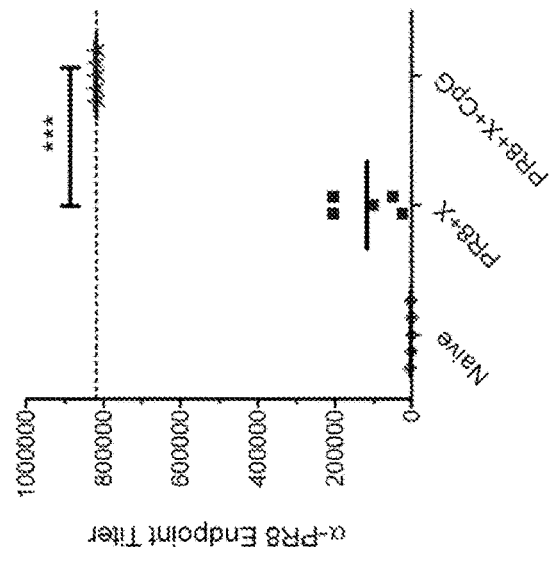
Figure 24B:
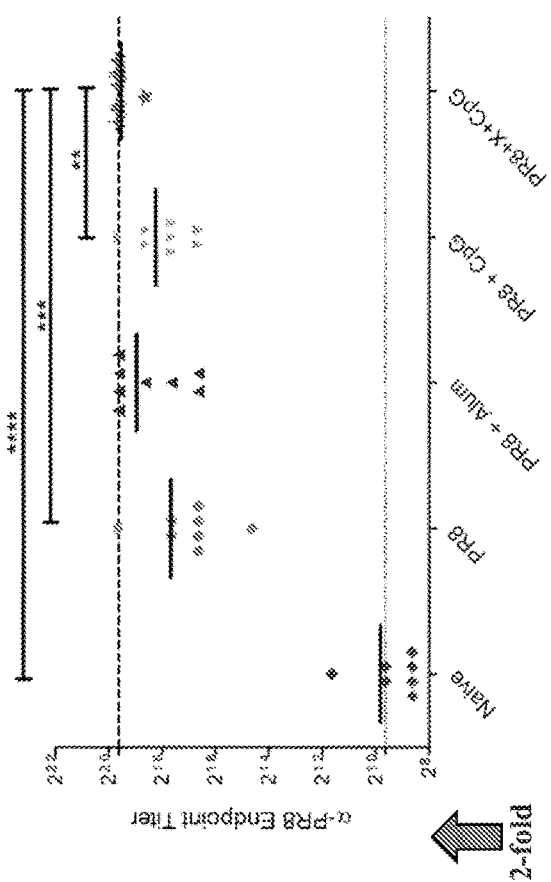
Figure 25A:
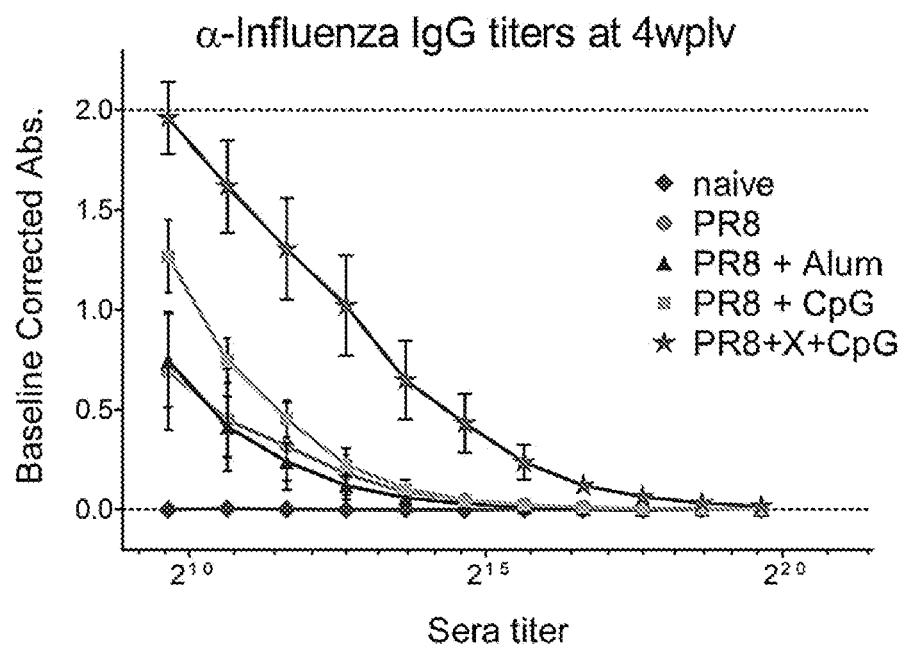
FIGS. 25A and 25B show anti-influenza IgG titers.
Figure 25B:
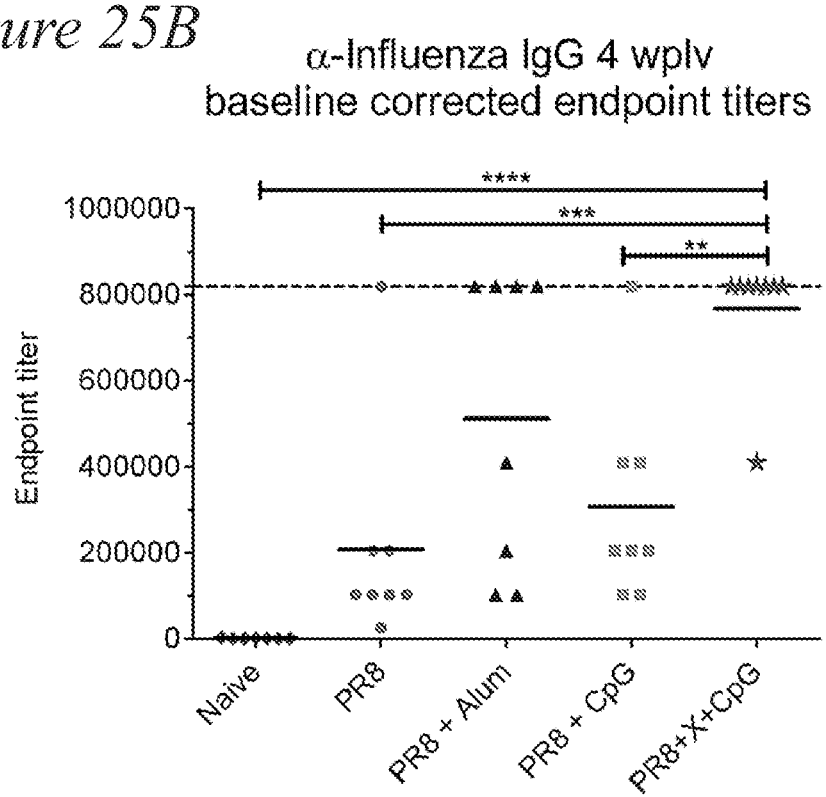

Influenza-specific IgG endpoint titers were determined from sera samples collected 4 weeks post single vaccination and immediately prior to challenge. As shown in FIG. 24, a 2-fold increase in a-PR8 influenza-specific antibody induction is seen in mice after a single vaccination with PR8 administered with as a slurry of PURAMATRIX and CpG, as compared to mice vaccinated with PR8 administered with CpG, mice vaccinated with PR8 administered with the adjuvant alum, or mice vaccinated with PR8 alone (FIG. 24B). In addition, a significant increase in influenza-specific antibody induction is seen in mice after a single vaccination with PR8 administered with as a slurry of PURAMATRIX and CpG, as compared to mice vaccinated with PR8 administered as a slurry of PURAMATRIX alone, without CpG. FIGS. 24B and 24C are representative of one triplicate experiment (n=5-9). FIG. 25 shows additional analysis of influenza-specific IgG endpoint titers determined from sera samples collected 4 weeks post last vaccination. As shown in each of FIGS. 25A and 25B, an increase in α-PR8 influenza-specific antibody induction is seen in mice after a single vaccination with PR8 administered with as a slurry of PURAMATRIX and CpG, as compared to mice vaccinated with PR8 administered with CpG, mice vaccinated with PR8 administered with the adjuvant alum, mice vaccinated with PR8 alone, or mice given a control (naïve) injection. FIGS. 25A and 25B are representative of one triplicate experiment (n=5-9).

Figure 26B:
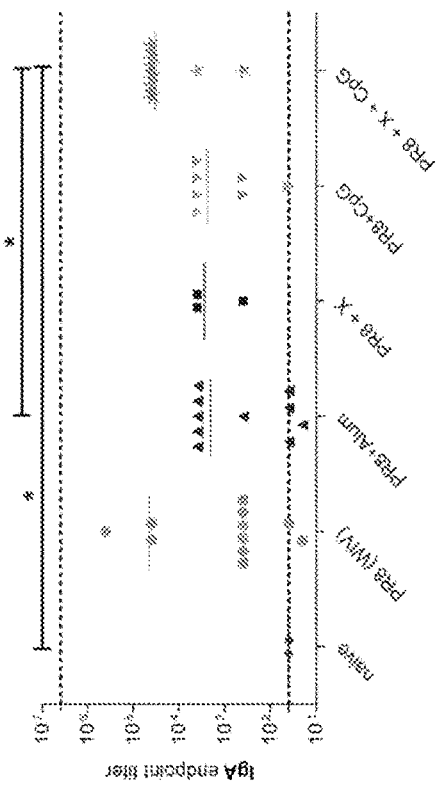
FIGS. 26A to 26D show an anti-PR8 influenza-specific antibody class analysis of pre-challenge sera at 4 weeks post vaccination.
Figure 26D:
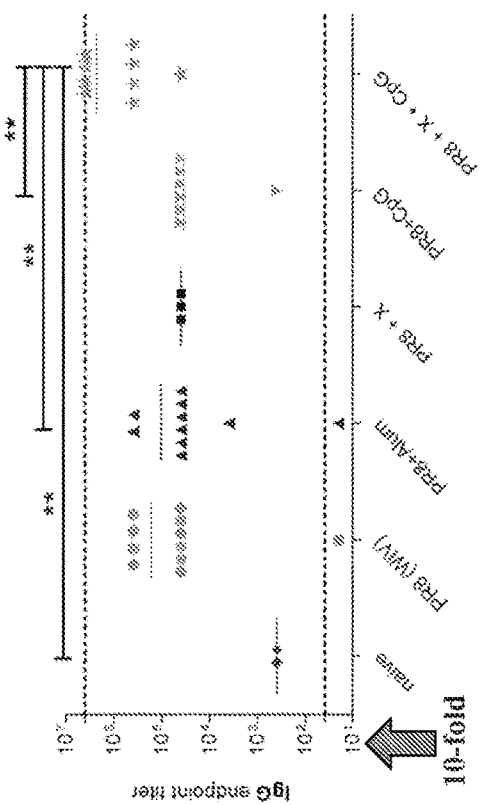
Figure 26A:
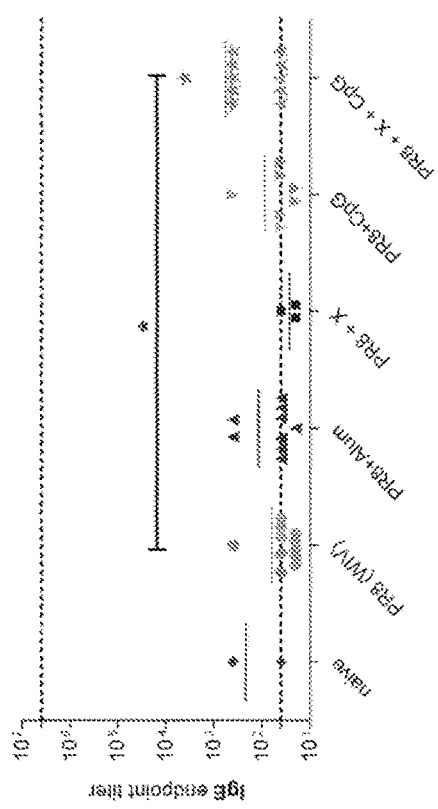
Figure 26C:
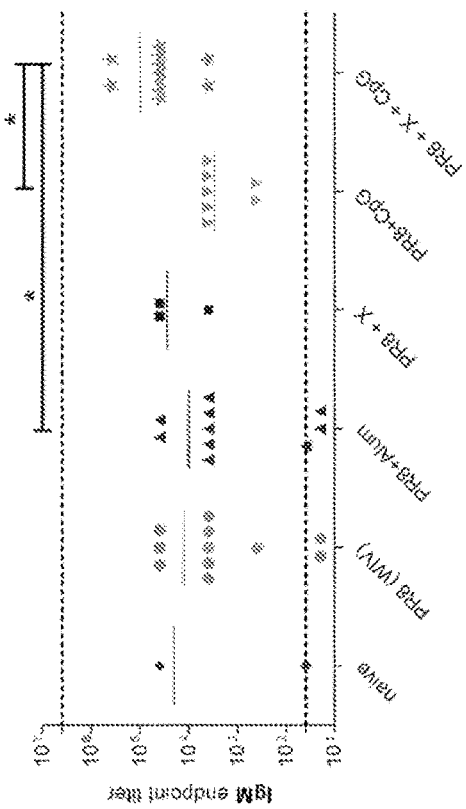
Figure 27A:
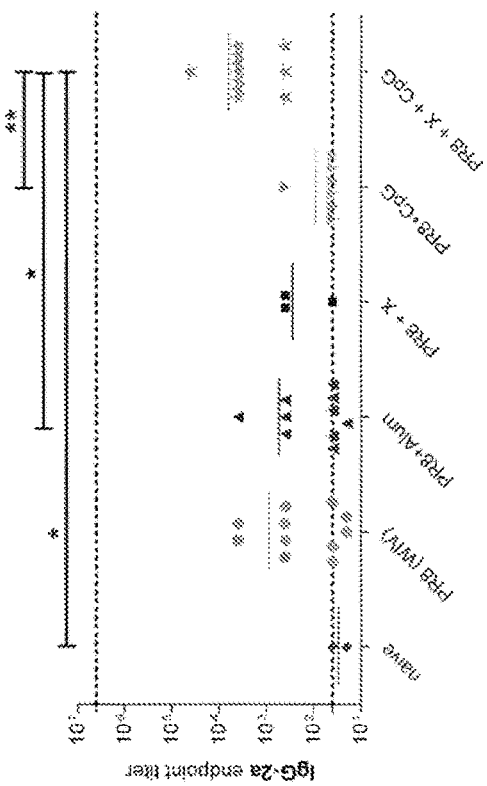
FIGS. 27A to 27D show an anti-PR8 influenza-specific antibody IgG subtype analysis of pre-challenge sera at 4 weeks post vaccination.
Figure 27B:
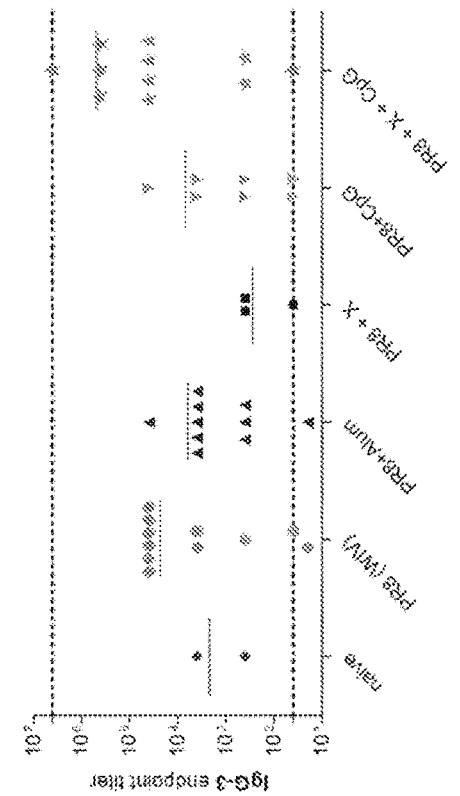
Figure 27C:
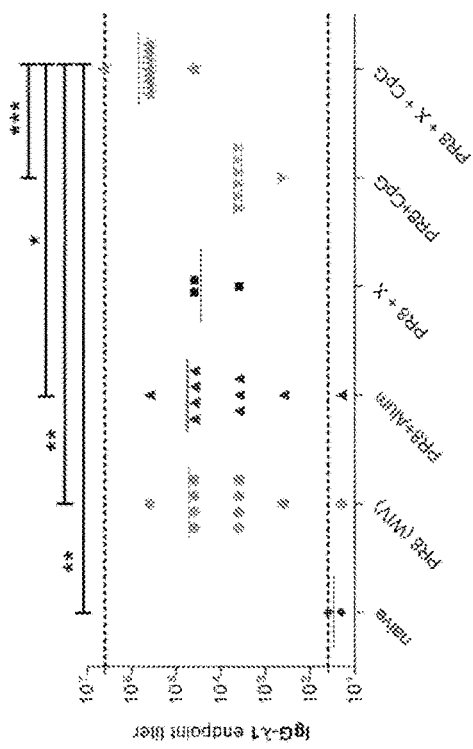
Figure 27D:
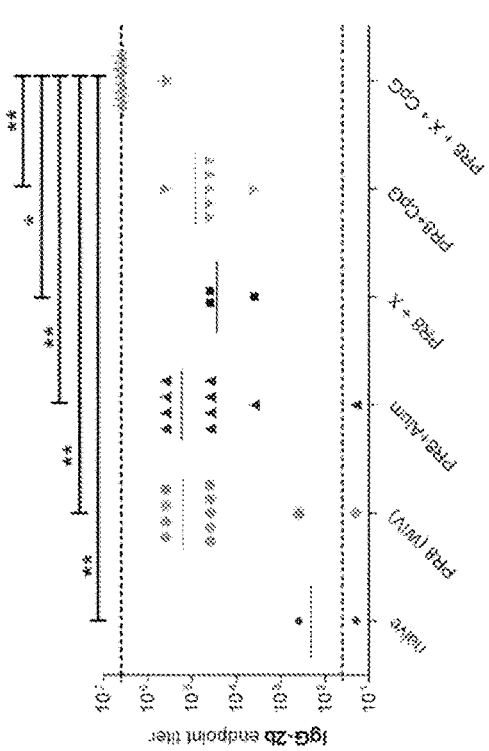

To further characterize this increase in influenza-specific antibodies, isotype and subtype analyses were performed. Influenza-specific IgE, IgA, IgM and IgG antibodies for different vaccine groups were analyzed. As shown in FIG. 26, an a-PR8 antibody class analysis of pre-challenge sera (at 4 weeks post vaccination) demonstrated increased endpoint titers of IgE (FIG. 26A), IgA (FIG. 26B), IgM (FIG. 26C), and IgG (10-fold; FIG. 26D) in mice after a single vaccination with PR8 administered with as a slurry of PURAMATRIX and CpG.

IgG-subtypes were further examined to determine the type of response (Th1 or Th2). Influenza-specific IgG (λ1), IgG(2a), IgG(2b) and IgG(3) levels for the same 6 vaccine groups were analyzed. As shown in FIG. 27, an IgG antibody subtype analysis of pre-challenge sera (at 4 weeks post vaccination) demonstrated increased endpoint titers of IgG-λ-1 (FIG. 27A), IgG-2a (FIG. 27B), IgG-2b (FIG. 27C), and IgG-3 (FIG. 27D) in mice after a single vaccination with PR8 administered with as a slurry of PURAMATRIX and CpG. The high endpoint titers & significant increases in the new method, over the other vaccine groups, in IgG(1) and IgG(2b) suggests a mixed Th1/Th2 response.

Morbidity and mortality were examined to determine whether this enhanced humoral response would correlation to protection. Following same vaccination schedule and groups described previously, mice were challenged a 4 weeks post vaccination with 1000LD$_{50}$PR8.

Figure 28A:
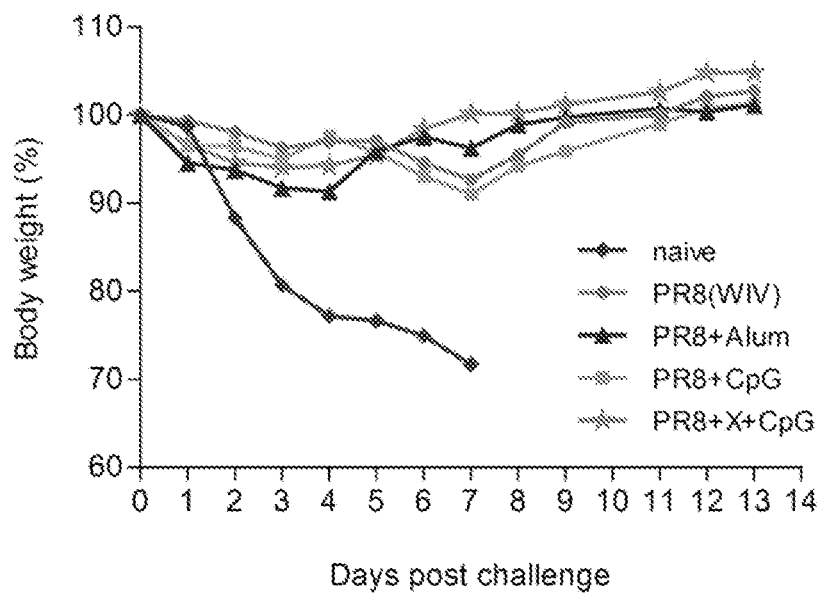
FIGS. 28A to 28C show decreased morbidity following lethal, homologous flu challenge.
Figure 28B:
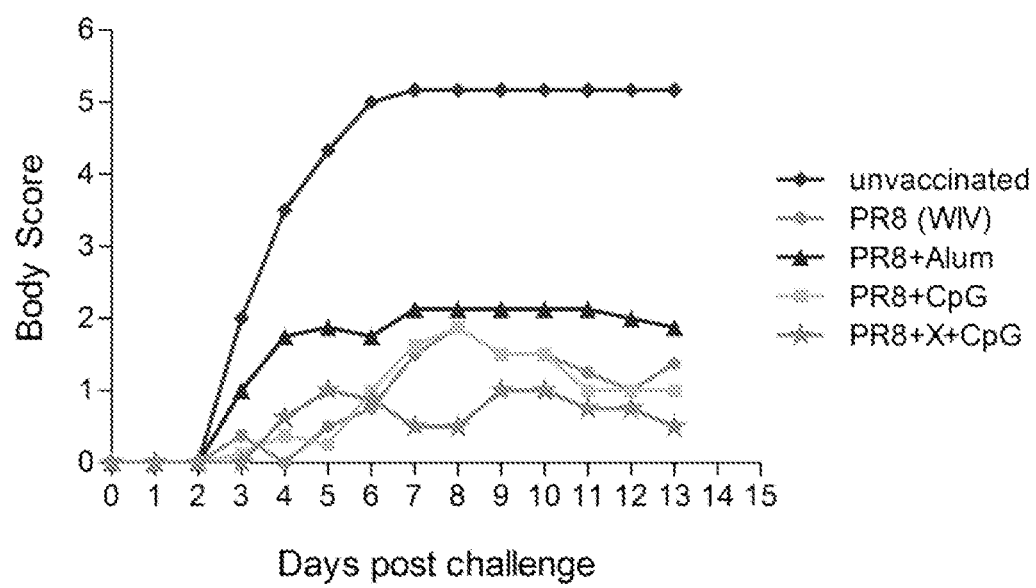
Figure 28C:
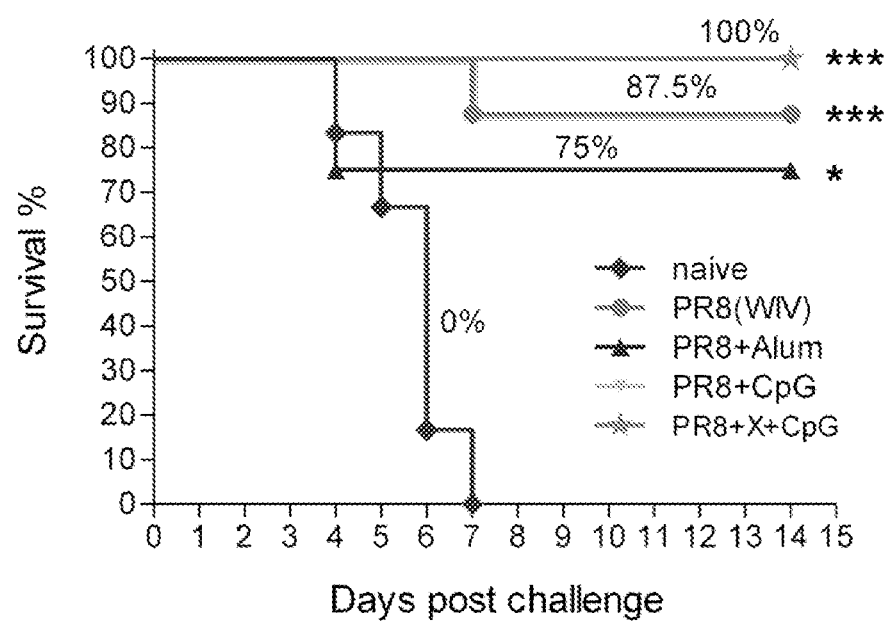

Morbidity was determined by daily monitoring and is expressed as the mean percent weight (FIG. 28A) change and the mean body score (FIG. 28B), for each group, over time post challenge. Body scores are comprised of several factors including weight loss, behavior and physical appearance. Thus, body score is a quantitative measure of symptom severity. As shown in FIG. 28, morbidity and mortality are decreased following lethal, homologous flu challenge at 1,000 LD$_{50}$. Mice that received a single vaccination of PR8 administered with as a slurry of PURAMATRIX and CpG, PR8 administered with CpG, PR8 administered with the adjuvant alum, or PR8 WIV maintained body weight (FIG. 28A) and body score (FIG. 28B). The PR8+X group was not included in this challenge; however, the PR8+X group was compared to these groups in another experiment and had a similar trend as the naive group. These results indicate that the new method, has a decreasing effect on morbidity Mortality was determined by looking at the percent survival over time post challenge, for each group. We observed that the new method is the only group able to provide 100% protection against a 1,000LD$_{50}$PR8 challenge (FIG. 28C). Multiple repeats show the new delivery method consistently decreasing morbidity and mortality rates following lethal PR8 challenge.

Example 10

Enhanced Viral Clearance Following Vaccination

Figure 29A:
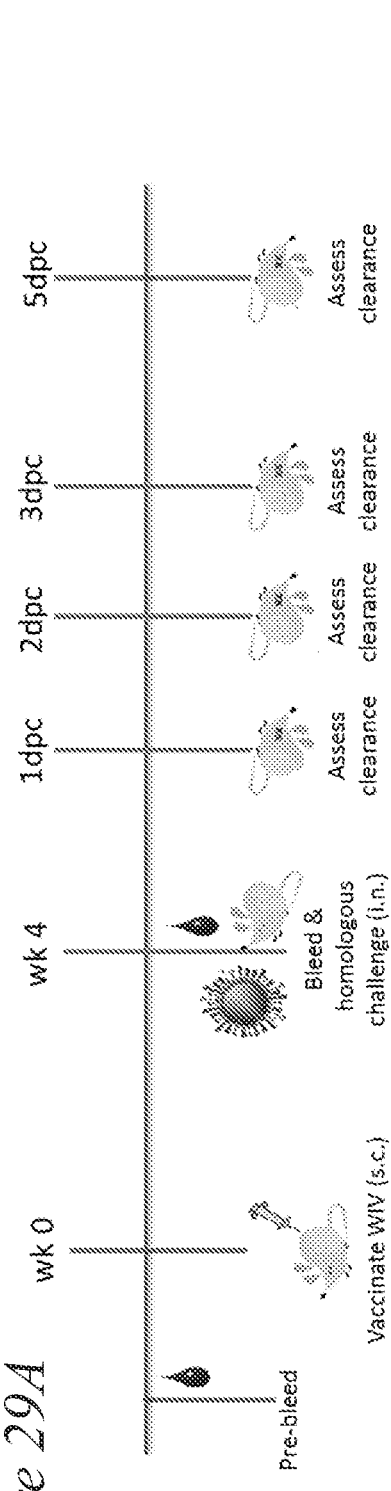
FIGS. 29A and 29B show viral clearance following homologous lethal challenge.

The preparation of vaccine compositions is described in more detail in the previous examples. Mice were immunized with whole inactivated influenza A virus (H1N1) strain Puerto Rico/08/34 (PR8) whole inactivated virus (WIV) or were immunized with PR8 administered as a slurry of PURAMATRIX and CpG. As a control, additional mice were immunized given a naive (mock) injection. A schematic of the method is shown in FIG. 29A. Blood samples from mice were collected the day prior to immunization and at week 4. A lethal influenza challenge of live homologous PR8 at 1,000 LD$_{50}$ was given by intra-nasal (in) administration at week 4. A sample of mice from each group was sacrificed at various time points post challenge (e.g., at 1, 2, 3, and 5 days post challenge) and the lungs were analyzed for viral clearance. Plaque assays were used to determine the amount of virus present in the lungs.

Figure 29B:
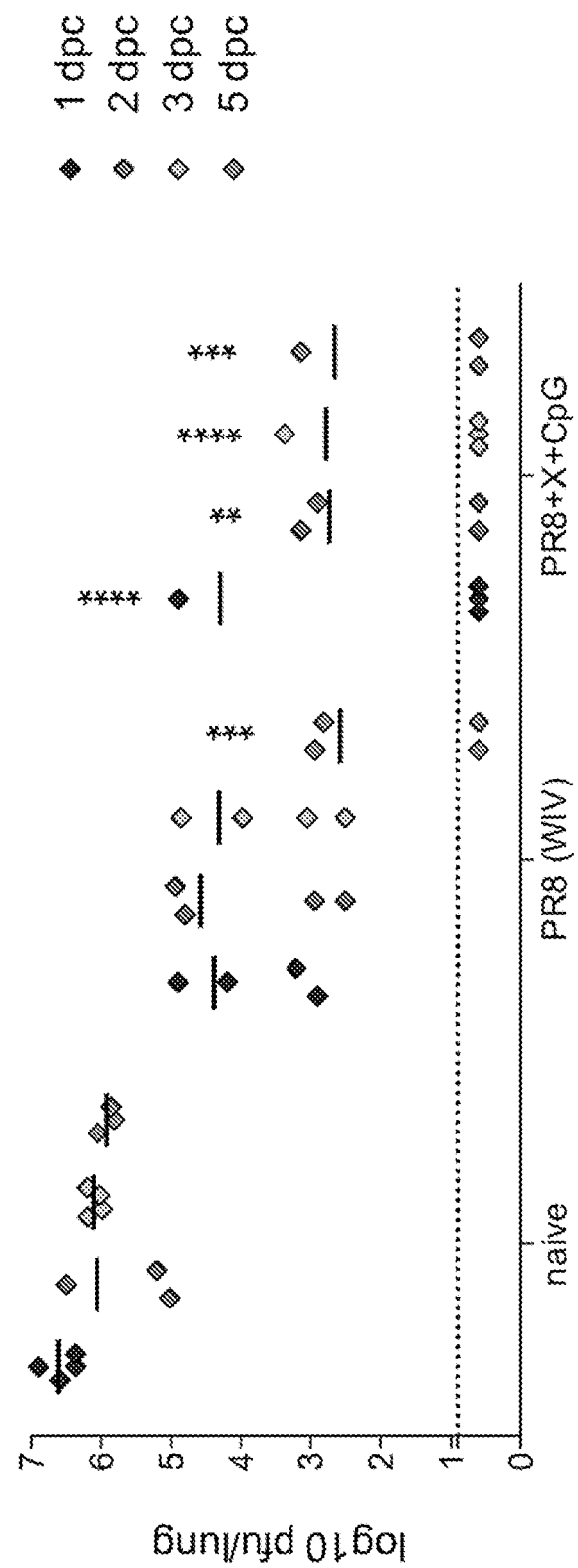

As shown in FIG. 29B, the amount of plaque forming units per lung of vaccinated mice decreased in the later time points as they were able to clear virus. Mice given a naive injection received replicating virus and had high levels of plaque forming units across all time points. Mice immunized with PR8 WIV show day 1 and day 2 virus levels approximately 2 logs lower than mice in the naive group and were clearing virus by day 5 post challenge. Mice immunized with PR8 administered as a slurry of PURAMATRIX and CpG had significantly lower viral burdens across all time points. At 1 day post challenge plaque forming units were almost 2 logs lower than the naive group. At 2 days post challenge plaque forming units were almost 4 logs lower than the naïve group and at approximately 2 logs lower than the mice vaccinated with PR8 WIV.

Figure 30A:
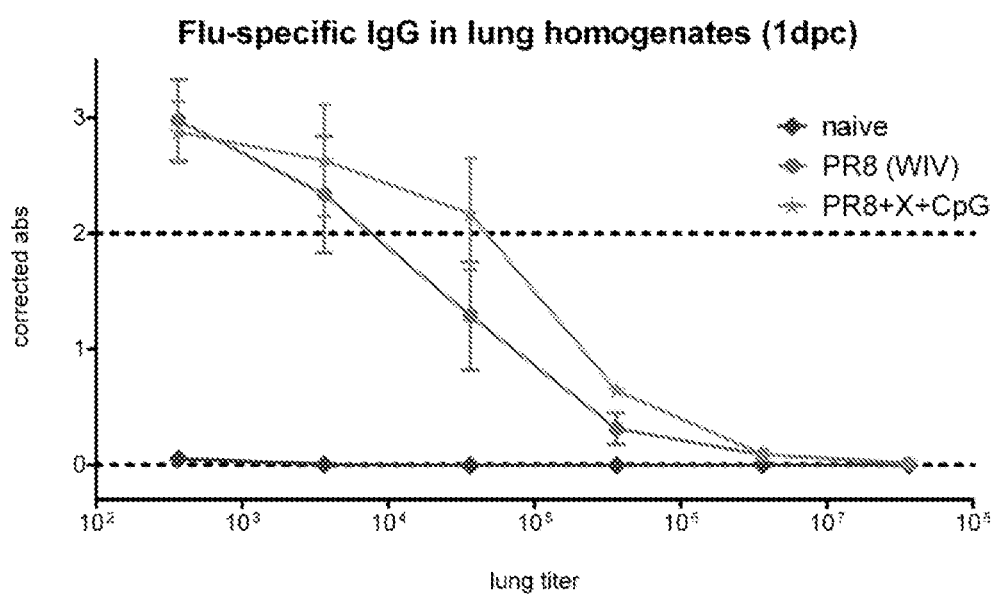
FIGS. 30A and 30B show mucosal IgG antibody titers in lung homogenates following challenge.
Figure 30B:
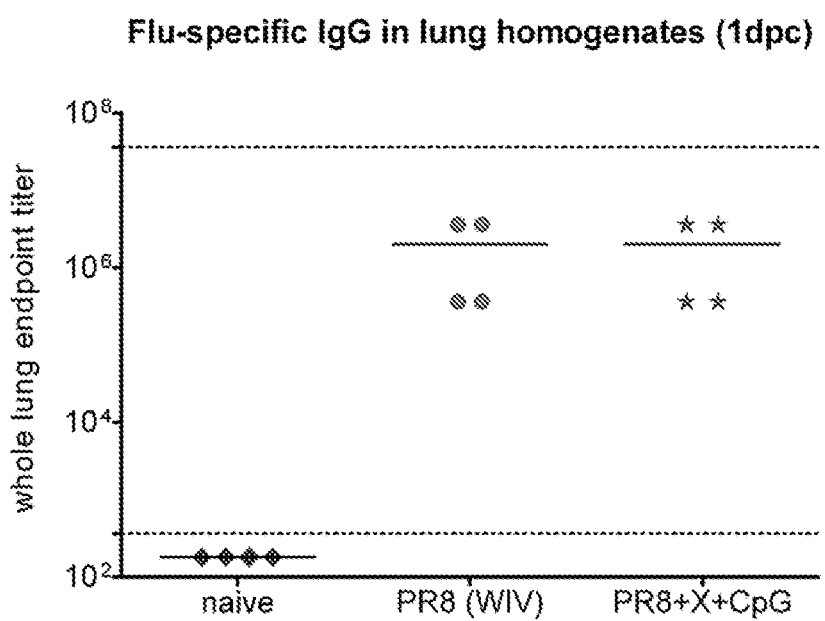

FIG. 30 shows additional analysis of influenza-specific IgG endpoint titers determined from sera samples collected 1 day post challenge. As shown in each of FIGS. 30A and 30B, an increase in α-PR8 influenza-specific antibody induction is seen at 1 day post challenge in mice vaccinated with PR8 alone and in mice vaccinated with PR8 administered with as a slurry of PURAMATRIX and CpG, as compared to mice given a control (naive) injection.

Figure 31A:
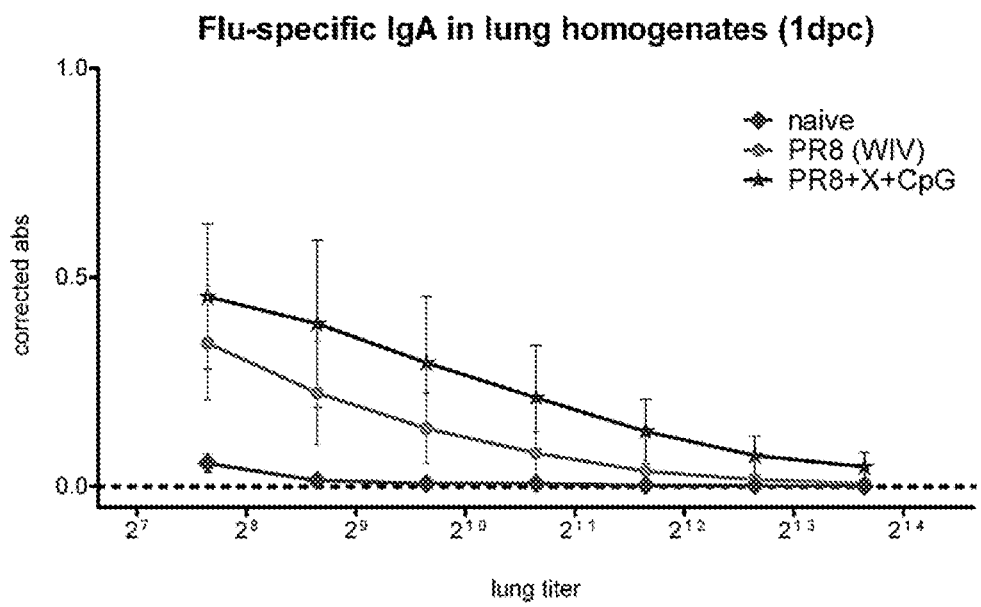
FIGS. 31A and 31B show mucosal IgA antibody titers in lung homogenates following challenge.
Figure 31B:
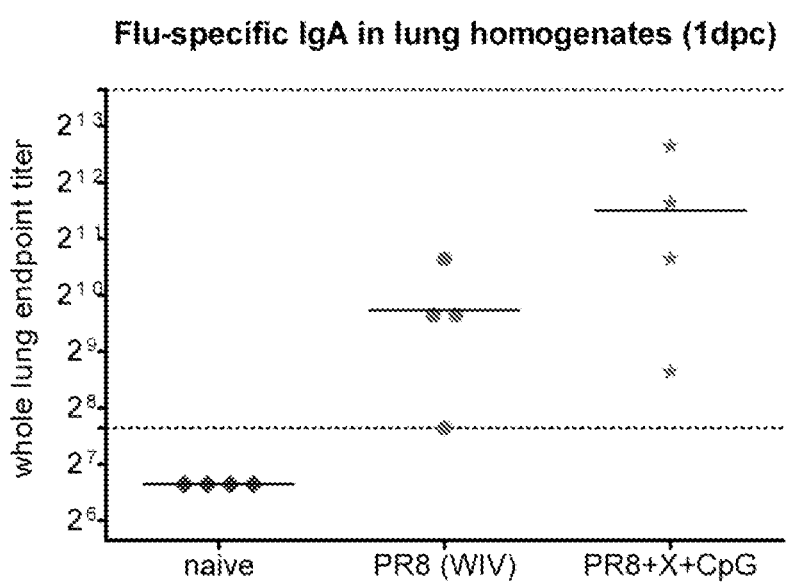

FIG. 31 shows additional analysis of influenza-specific IgA endpoint titers determined from sera samples collected 1 day post challenge. As shown in each of FIGS. 31A and 31B, an increase in a-PR8 influenza-specific antibody induction is seen at 1 day post challenge in mice vaccinated with PR8 administered with as a slurry of PURAMATRIX and CpG, as compared to mice vaccinated with PR8 alone. An increase in a-PR8 influenza-specific antibody induction is seen at 1 day post challenge in mice vaccinated with PR8 alone when compared to mice given a control (naïve) injection.

Example 11

Inter-Strain Reactivity

Figure 32A:
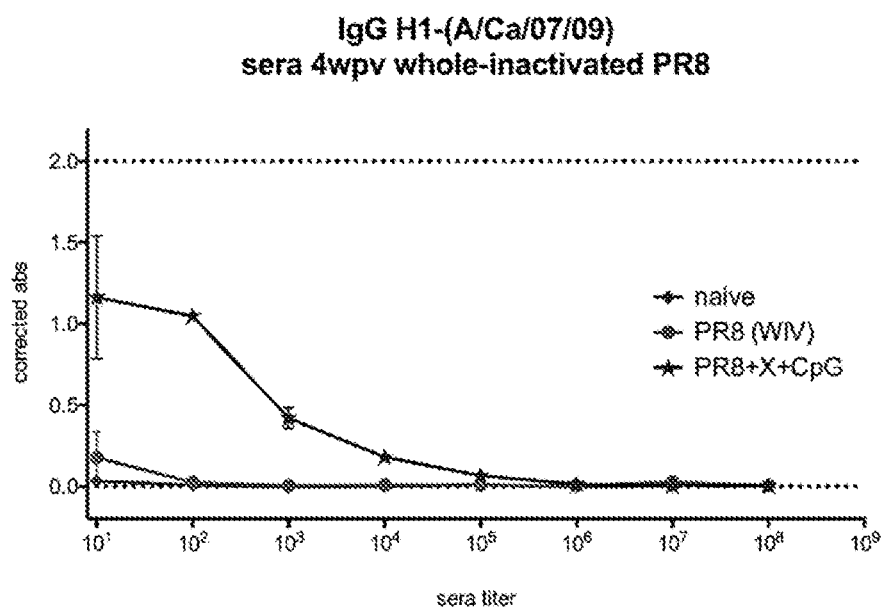
FIGS. 32A and 32B show inter-strain reactivity of anti-HA IgG antibodies in sera.
Figure 32B:
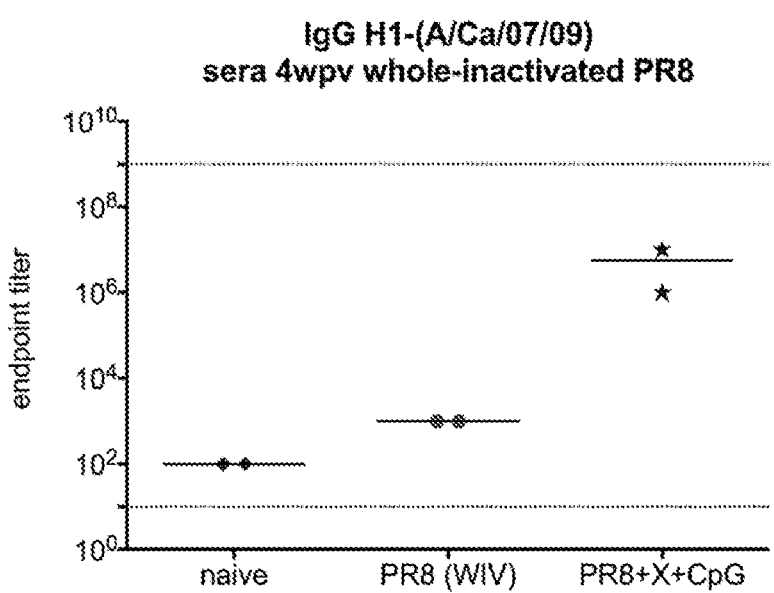
Figure 33A:
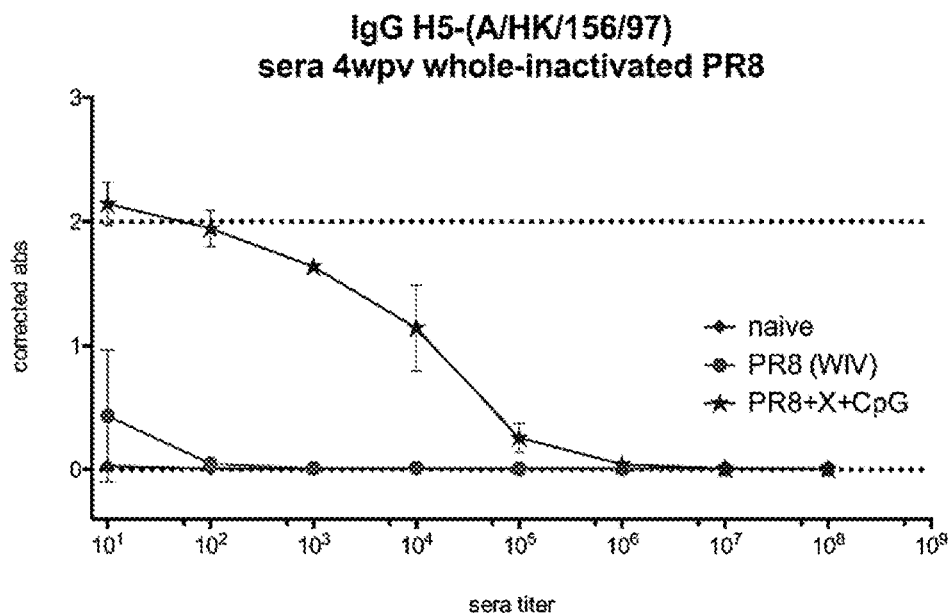
FIGS. 33A and 33B show inter-strain reactivity of anti-HA IgG antibodies in sera.
Figure 33B:
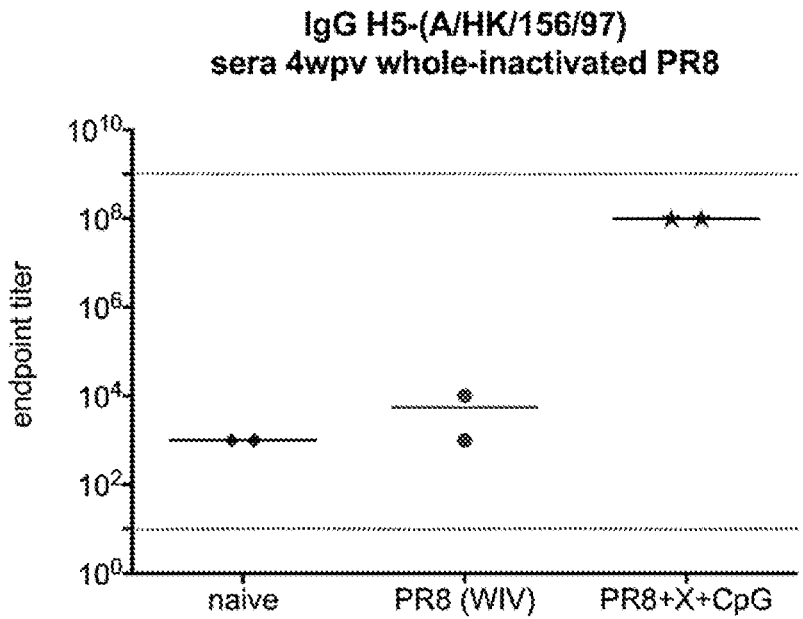

The preparation of vaccine compositions is described in more detail in the previous examples. Mice were vaccinated with A/PR/8/34 (PR8; NCBI accession no. ABO21709; SEQ ID NO:7) whole inactivated virus (WIV). Sera was collected pre-challenge and at 4 weeks post-vaccination. Sera samples were titered in ELISA coated with 2 µg/ml hemagglutinin (HA) from either A/CA/07/09 (H1N1) or A/HK/156/97 (H5N1). FIGS. 32A, 32B, 33A and 33B show development of broadly reactive a-HA IgG antibodies in sera. The amino acid sequence of the HA of A/PR/8/34 (PR8) is NCBI accession no. ABO21709 (SEQ ID NO:7). The amino acid sequence of the HA of A/CA/07/09 (H1N1; NCBI accession no. AFM72832; SEQ ID NO:8) has 81.3% identity with HA PR8. FIG. 32 shows the inter-strain reactivity between PR8 and H1N1. The amino acid sequence of the HA of A/HK/156/97 (H5N1; NCBI accession no. AAC34263; SEQ ID NO:8) has 81.3% identity with HA of PR8. FIG. 33 shows the inter-strain reactivity between PR8 and H5N1.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified.

What is claimed is:

1. A vaccine composition comprising a peptide hydrogel of the peptide scaffold RADARADARADARADA (SEQ ID NO:2), an influenza antigen, and a TLR9 agonist, wherein the vaccine composition is a liquid at room temperature, non-physiological pH, and/or non-physiological salt concentrations and a gel at physiological pH, physiological salt concentrations and/or physiological temperatures, and wherein the vaccine composition gels after administration to a subject.

2. The vaccine composition of claim 1, wherein the TLR9 agonist comprises a CpG oligodeoxynucleotide (ODN).

3. The vaccine composition of claim 1, wherein the influenza antigen comprises an influenza A, influenza B, or influenza C antigen.

4. The vaccine composition of claim 1, wherein the influenza antigen comprises a recombinant nucleoprotein (rNP) influenza virus antigen.

5. The vaccine composition of claim 1, wherein the influenza antigen comprises a whole-inactivated influenza virus.

6. The vaccine composition of claim 1, wherein the vaccine composition is lyopholized.

7. A method of producing an immune response in a subject, the method comprising administering a vaccine composition of claim 1 to the subject.

8. A method of vaccinating a subject to influenza, the method comprising administering a vaccine composition of claim 1 to the subject.

9. The method of claim 7, wherein the subject is human.

10. The method of claim 7, wherein administration of the composition comprises subcutaneous (sc) delivery, intramuscular (im) delivery, intradermal delivery, transdermal delivery, mucosal delivery, intravaginal delivery, intrarectal delivery, intraperitoneal delivery, inhalation delivery, and/or aerosol delivery.

* * * * *

SEQUENCE LISTING

```
<160> NUMBER OF SEQ ID NOS: 9

<210> SEQ ID NO 1
<211> LENGTH: 4
<212> TYPE: PRT
<213> ORGANISM: artificial
<220> FEATURE:
<223> OTHER INFORMATION: building block of synthetic self-assembling
      peptide scaffold

<400> SEQUENCE: 1

Arg Ala Asp Ala
1

<210> SEQ ID NO 2
<211> LENGTH: 16
<212> TYPE: PRT
<213> ORGANISM: artificial
<220> FEATURE:
<223> OTHER INFORMATION: synthetic self-assembling RAD16-I peptide
      scaffold

<400> SEQUENCE: 2

Arg Ala Asp Ala Arg Ala Asp Ala Arg Ala Asp Ala Arg Ala Asp Ala
1               5                   10                  15

<210> SEQ ID NO 3
<211> LENGTH: 16
<212> TYPE: PRT
<213> ORGANISM: artificial
<220> FEATURE:
<223> OTHER INFORMATION: synthetic self-assembling RAD16-II peptide
      scaffold

<400> SEQUENCE: 3

Arg Ala Arg Ala Asp Ala Asp Ala Arg Ala Arg Ala Asp Ala Asp Ala
1               5                   10                  15

<210> SEQ ID NO 4
<211> LENGTH: 8
<212> TYPE: PRT
<213> ORGANISM: artificial
<220> FEATURE:
<223> OTHER INFORMATION: synthetic self-assembling KFE-8 peptide
      scaffold
```

```
<400> SEQUENCE: 4

Phe Lys Phe Glu Phe Lys Phe Glu
1               5

<210> SEQ ID NO 5
<211> LENGTH: 12
<212> TYPE: PRT
<213> ORGANISM: artificial
<220> FEATURE:
<223> OTHER INFORMATION: synthetic self-assembling KLD-12 peptide
      scaffold

<400> SEQUENCE: 5

Lys Leu Asp Leu Lys Leu Asp Leu Lys Leu Asp Leu
1               5                   10

<210> SEQ ID NO 6
<211> LENGTH: 12
<212> TYPE: PRT
<213> ORGANISM: artificial
<220> FEATURE:
<223> OTHER INFORMATION: synthetic S 228-39 peptide for T-cell analysis
      for flow cytometry

<400> SEQUENCE: 6

Ile Pro Gln Ser Leu Asp Ser Trp Trp Thr Ser Leu
1               5                   10

<210> SEQ ID NO 7
<211> LENGTH: 565
<212> TYPE: PRT
<213> ORGANISM: Influenza A virus

<400> SEQUENCE: 7

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
```

```
                195                 200                 205
Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
        290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 8
<211> LENGTH: 566
<212> TYPE: PRT
<213> ORGANISM: Influenza A virus

<400> SEQUENCE: 8
```

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
            210                 215                 220

Lys Lys Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
```

```
                420                 425                 430
Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 9
<211> LENGTH: 552
<212> TYPE: PRT
<213> ORGANISM: Influenza A virus

<400> SEQUENCE: 9

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asn His Asp Ala Ser
        115                 120                 125

Ser Gly Val Ser Ser Ala Cys Pro Tyr Leu Gly Arg Ser Ser Phe Phe
    130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Glu Ile Ala Thr Arg Pro Lys Val Asn Gly Gln Ser Gly
    210                 215                 220
```

```
Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
            245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Thr
305                 310                 315                 320

Pro Gln Arg Glu Arg Arg Lys Lys Arg Gly Leu Phe Gly Ala Ile
            325                 330                 335

Ala Gly Phe Ile Glu Gly Gly Trp Gln Gly Met Val Asp Gly Trp Tyr
                340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Lys Asn Gly Thr Tyr Asp Tyr Pro Gln Tyr Ser Glu Glu Ala
            485                 490                 495

Arg Leu Asn Arg Glu Glu Ile Ser Gly Val Lys Leu Glu Ser Met Gly
            500                 505                 510

Thr Tyr Gln Ile Leu Ser Ile Tyr Ser Thr Val Ala Ser Ser Leu Ala
            515                 520                 525

Leu Ala Ile Met Val Ala Gly Leu Ser Leu Trp Met Cys Ser Asn Gly
            530                 535                 540

Ser Leu Gln Cys Arg Ile Cys Ile
545                 550
```